United States Patent
Khleif et al.

(10) Patent No.: US 12,048,745 B2
(45) Date of Patent: Jul. 30, 2024

(54) METHODS FOR DETECTING AND REVERSING IMMUNE THERAPY RESISTANCE

(71) Applicant: Augusta University Research Institute, Inc., Augusta, GA (US)

(72) Inventors: Samir N. Khleif, Silver Spring, MD (US); Vivek Verma, Augusta, GA (US); Seema Gupta, Bethesda, MD (US)

(73) Assignee: AUGUSTA UNIVERSITY RESEARCH INSTITUTE, INC., Augusta, GA (US)

( * ) Notice: Subject to any disclaimer, the term of this patent is extended or adjusted under 35 U.S.C. 154(b) by 207 days.

(21) Appl. No.: 16/400,595

(22) Filed: May 1, 2019

(65) Prior Publication Data

US 2019/0336600 A1 Nov. 7, 2019

Related U.S. Application Data

(60) Provisional application No. 62/775,573, filed on Dec. 5, 2018, provisional application No. 62/665,052, filed on May 1, 2018.

(51) Int. Cl.
| | |
|---|---|
| *A61K 39/395* | (2006.01) |
| *A61K 9/00* | (2006.01) |
| *A61K 38/19* | (2006.01) |
| *A61P 35/00* | (2006.01) |
| *G01N 33/49* | (2006.01) |
| *A61K 39/00* | (2006.01) |
| *A61K 45/06* | (2006.01) |
| *G01N 15/01* | (2024.01) |
| *G01N 15/10* | (2006.01) |

(52) U.S. Cl.
CPC ...... *A61K 39/39558* (2013.01); *A61K 9/0019* (2013.01); *A61K 38/195* (2013.01); *A61P 35/00* (2018.01); *G01N 33/4915* (2013.01); *A61K 2039/80* (2018.08); *A61K 45/06* (2013.01); *G01N 15/01* (2024.01); *G01N 2015/1006* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 5,620,956 A | 4/1997 | Clayberger | |
| 6,005,079 A | 12/1999 | Casterman | |
| 7,052,694 B2 | 5/2006 | Pease | |
| 7,226,592 B2 | 6/2007 | Kreysch | |
| 7,332,582 B2 | 2/2008 | Hardy | |
| 7,390,888 B2 | 6/2008 | Pease | |
| 7,411,051 B2 | 8/2008 | Rosen | |
| 7,488,802 B2 | 2/2009 | Collins | |
| 7,521,051 B2 | 4/2009 | Collins | |
| 7,524,498 B2 | 4/2009 | Hardy | |
| 7,563,869 B2 | 7/2009 | Honjo | |
| 7,981,416 B2 | 7/2011 | Hardy | |
| 8,088,896 B2 | 1/2012 | Tesar | |
| 8,088,905 B2 | 1/2012 | Collins | |
| 8,153,765 B2 | 4/2012 | Park | |
| 8,188,238 B2 | 5/2012 | Pease | |
| 8,263,746 B2 | 9/2012 | Tesar | |
| 8,268,314 B2 | 9/2012 | Baehner | |
| 8,287,856 B2 | 10/2012 | Li | |
| 8,362,211 B2 | 1/2013 | Elias | |
| 8,383,796 B2 | 2/2013 | Korman | |
| 8,728,474 B2 | 5/2014 | Honjo | |
| 8,779,105 B2 | 7/2014 | Korman | |

(Continued)

FOREIGN PATENT DOCUMENTS

| | | |
|---|---|---|
| WO | 94/04678 | 3/1994 |
| WO | 94/25591 | 11/1994 |

OTHER PUBLICATIONS

Krejcik, Jakub, et al. "Daratumumab depletes CD38+ immune regulatory cells, promotes T-cell expansion, and skews T-cell repertoire in multiple myeloma." Blood 128.3 (2016): 384-394. (Year: 2016).*
Beyranvand Nejad, Elham, et al. "The importance of correctly timing cancer immunotherapy." Expert opinion on biological therapy 17.1 (2017): 87-103. (Year: 2017).*
Yang, Fa, Weihong Wen, and Weijun Qin. "Bispecific antibodies as a development platform for new concepts and treatment strategies." International journal of molecular sciences 18.1 (2017): 48. (Year: 2017).*
Chen, Limo, et al. "CD38 as a novel immune checkpoint and a mechanism of resistance to the blockade of the PD-1/PD-L1 axis." (2017): 79-79. (Year: 2017).*
Tinhofer, Inge, et al. Blood 108.9 (2006): 2950-2956 (Year: 2006).*
Schnell, see entire document, in particular, Section 5) (Schnell, Annette, et al. Biomedicines 6.1 (2018): 25 (Year: 2018).*

(Continued)

*Primary Examiner* — Michael Szperka
*Assistant Examiner* — Lia E Taylor
(74) *Attorney, Agent, or Firm* — PABST PATENT GROUP LLP

(57) ABSTRACT

Compositions and methods of their use to detect and treat anti-PD1 therapy resistance are provided herein. Compositions that immunospecifically bind and deplete dysfunctional T cells are provided. The dysfunctional T cells that are depleted include $CD38^+PD-1^+$ T cells, $CD38^+CD8^+$ T-cells, or both. The dysfunctional T cells can be depleted, for example, by administering an antibody or fusion protein that specifically binds to dysfunctional T cells and promotes their depletion. In one embodiment the antibody is a bispecific antibody that can be specific for CD38 and CD8, or it can be specific for CD38 and PD-1. Also disclosed is a method of detecting and treating anti-PD1 therapy resistance by measuring the amount of CD38+PD1+CD8 T cells in blood or tissue samples obtained from a subject prior to anti-PD1 therapy and administering an anti-CD38/CD8 or anti-CD38/PD-1 depleting/blocking antibody to the subject prior to anti-PD1 therapy.

23 Claims, 18 Drawing Sheets

Specification includes a Sequence Listing.

(56) References Cited

U.S. PATENT DOCUMENTS

| | | | |
|---|---|---|---|
| 9,067,999 B1 | 6/2015 | Honjo | |
| 9,073,994 B2 | 7/2015 | Honjo | |
| 9,079,965 B2 | 7/2015 | Zhou | |
| 9,084,776 B2 | 7/2015 | Korman | |
| 9,102,725 B2 | 8/2015 | Korman | |
| 9,205,148 B2 | 12/2015 | Langermann | |
| 9,255,147 B2 | 2/2016 | Pease | |
| 9,273,135 B2 | 3/2016 | Korman | |
| 9,315,567 B2 | 4/2016 | Chang | |
| 9,358,289 B2 | 6/2016 | Korman | |
| 9,387,247 B2 | 7/2016 | Korman | |
| 9,393,301 B2 | 7/2016 | Honjo | |
| 9,492,539 B2 | 11/2016 | Korman | |
| 9,492,540 B2 | 11/2016 | Korman | |
| 9,580,507 B2 | 2/2017 | Korman | |
| 2016/0339090 A1* | 11/2016 | Hacohen | C07K 16/2818 |

OTHER PUBLICATIONS

Adan, Aysun, et al., "Flow Cytometry: Basic Principles and Applications", Crit Rev Biotech, 37:163-176 (2017).

Angal, S., et al., "A Single Amino acid Substitution Abolishes the Heterogeneity of Chimeric Mouse/Human (IgG4) Antibody", Mol Immunol. 30:105-108 (1993). (Abstract Only).

Berger, Raanan et al., "Phase I Safety and Pharmacokinetic Study of CT-011, a Humanized Antibody Interacting with PD-1, in Patients with Advanced Hematologic Malignancies", Clin Cancer Res., 14:3044-3051 (2008).

Boussiotis, Vassiliki A., "Molecular and Biochemical Aspects of the PD-1 Checkpoint Pathway", N Eng J Med, 375:1767-1778 (2016).

Butte, Manish J. et al., "PD-L1 Interacts Specifically with B7-1 to Inhibit T Cell Proliferation", Immunity, 27:111-122 (2007).

Chapoval, Andrei I. et al., "Immunoglobulin Fusion Proteins as a Tool for Evaluation of T-Cell Costimulatory Molecules", Methods Mol Med, 45:247-255 (2000).

Chen, Lieping et al., "Molecular Mechanisms of T Cell Co-Stimulation and Co-Inhibition", Nat Rev Immunol, 13:227-242 (2013).

Chini, Eduardo N. et al., "The Pharmacology of CD38/NADase: An Emerging Target for Cancer and Aging Diseases", Trends Pharmacol Sci, 39(4):424-436 (2018).

Chiu, M.L. et al., "Engineering Antibody Therapeutics," Curr Opi Structural Biol, 38:163-173 (2016). (Abstract Only).

Chothia, Cyrus et al., "Canonical Structures for the Hypervariable Regions of Immunoglobulins", J Mol Biol, 196:901-917 (1987).

Cubillos-Ruiz, Juan R. et al., "Polyethylenimine-Based siRNA Nanocomplexes Reprogram Tumor-associated Dendritic Cells via TLR5 to Elicit Therapeutic Antitumor Immunity", J Clin Invest, 119(8): 2231-2244 (2009).

Day, C.L. et al., "PD-1 Expression on HIV-Specific T Cells is Associated with T-Cell Exhaustion and Disease Progression", Nature, 443:350-354 (2006). (Abstract Only).

Dondi, Elisabetta et al., "A Dual Role of IFN-α in the Balance between Proliferation and Death of Human CD4+ T Lymphocytes during Primary Response", J Immunol, 173:3740-3747 (2004).

Eisenhauer, E.A. et al., New Response Evaluation Criteria in Solid Tumours: Revised RECIST Guideline (Version 1.1), Eur J Cancer, 45:228-247 (2009). (Abstract Only).

Freeman, Gordon J., "Structures of PD-1 with its Ligands: Sideways and Dancing Cheek to Cheek", Proc Natl Acad Sci U. S. A, 105:10275-10276 (2008).

Guatelli, John C. et al., "Isothermal, in vitro Amplification of Nucleic Acids by a Multienzyme Reaction Modeled After Retroviral Replication", Proc Natl Acad Sci USA 87:1874-1878 (1990).

Hamanishi, Junzo et al., "PD-1/PD-L1 Blockage in Cancer Treatment: Perspectives and Issues", Int J Clin Oncol, 21:462-473 (2016).

Huang, Alexander C. et al., "T-Cell Invigoration to tumour Burden Ration Associated with Anti-PD-1 Response", Nature, 545:60-65 (2017).

Hyrup, Birgitte et al. "Peptide Nucleic Acids (PNA): Synthesis, Properties and Potential Applications", Bioorgan Med Chem, 4:5-23 (1996).

Jiang, Y. et al., "T-Cell Exhaustion in the Tumor Microenvironment", Cell Death Dis, 6:e1792 (2015).

Katz, Zachary B. et al., "A Cycle of Zap70 Kinase Activation and Release from the TCR Amplifies and Disperses Antigenic Stimuli", Nat Immunol, 18:86-95 (2017).

Kleponis, Jennifer et al., "Fueling the Engine and Releasing the Break: Combinational Therapy of Cancer Vaccines and Immune Checkpoint Inhibitors", Cancer Biol Med, 12:201-208 (2015).

Atchman, Yvette et al., PD-L2 is a Second Ligand for PD-1 and Inhibits T Cell Activation, Nat Immunol, 2:261-268 (2001).

Lázár-Molnár, Eszter et al., "Crystal Structure of the Complex between Programmed Death-1 (PD-1) and its Ligand PD-L2", PNAS, 105:10483-10488 (2008).

Lin, Ken-Yu et al., "Treatment of Established tumors with a Novel Vaccine That Enhances Major Histocompatibility Class II Presentation of Tumor Antigen1", Cancer Res, 56:21-26 (1996).

Lohman, Barbara L. et al., "Apoptotic Regulation of T Cells and Absence of Immune Deficiency in Virus-Infected Gamma Interferon Receptor Knockout Mice", J Virol, 72:7815-7821 (1998).

Muyldermans, Serge et al., "Recognition of Antigens by Single-Domain Antibody Fragments: The Superfluous Luxury of Paired Domains", Trends Biochem Sci, 26:230 (2001).

Nuttall, S.D. et al., "Immunoglobulin V11 Domains and Beyond: Design and Selection of Single-Domain Binding and Targeting Reagents", Cur Pharm Biotech, 1:253 (2000).

Overwijk, Willem W. et al., "gp100/pmel 17 Is a Murine Tumor Rejection Antigen: Induction of "Self"-Reactive, Tumoricidal T Cells Using High-Affinity, Altered Peptide Ligand", J Exp Med, 188:277-286 (1998).

Page, David B. et al., "Immune Modulation in Cancer with Antibodies", Annu Rev Med, 65:185-202 (2014).

Patsoukis, Nikolaos et al., "Immunometabolic Regulations Mediated by Coinhibitory Receptors and Their Impact on T Cell Immune Responses", Front Immunol, 8:330 (2017).

Refaeli, Yosef et al., "Interferon γ Is Required for Activation-Induced Death of T Lymphocytes", J Exp Med, 196:999-1005 (2002).

Riechmann, Lutz et al., "Single Domain Antibodies: Comparison of Camel VH and Camelised Human VH Domains", J Immunol Meth, 231:25 (1999). (Abstract Only).

Saeed, Abdullah F.U.H. et al., "Antibody Engineering for Pursuing a Healthier Future," Frontiers in Microbiology, 8:495 (2017).

Summerton, J. et al., "Morpholino Antisense Oligomers: Design, Preparation, and Properties", Antisense Nucleic Acid Drug Dev, 7:187-195 (1997). (Abstract Only).

Topalian, Suzanne L., et al., "Immune Checkpoint Blockade: A Common Denominator Approach to Cancer Therapy", Cancer Cell, 27:450-461 (2015).

Trautmann, Lydie et al., "Upregulation of PD-1 Expression on HIV-Specific CD8+ T Cells Leads to Reversible Immune Dysfunction", Nat Med, 12:1198-1202 (2006).

Villani, Alexandra-Chloé et al., "Single-Cell RNA-Seq Reveals New Types of Human Blood Dendritic Cells, Monocytes and Progenitors", Science, 356:6335 (2017).

Wang, Haopeng et al., "ZAP-70: An Essential Kinase in T-Cell Signaling", Cold Spring Harb Perspect Biol, 2: a002279 (2010).

Weiss, R., "Hot Prospect for New Gene Amplifier", Science, 254:1292-1293 (1991).

Yang, Fa et al., "Bispecific Antibodies as a Development Platform for New Concepts and Treatment Strategies", Int J Mol Sci, 18:48 (2016).

Yokosuka, Tadashi et al., "Programmed Cell Death 1 Forms Negative Costimulatory Microclusters that Directly Inhibit T Cell Receptor Signaling by Recruiting Phosphatase SHP2", J Exp Med, 209:1201-1217 (2012).

Zou, Weiping et al., "PD-L1 (B7-H1) and PD-1 Pathway Blockade for Cancer Therapy: Mechanisms, Response Biomarkers and Combinations", Sci Transl Med, 8:328rv4 (2016).

* cited by examiner

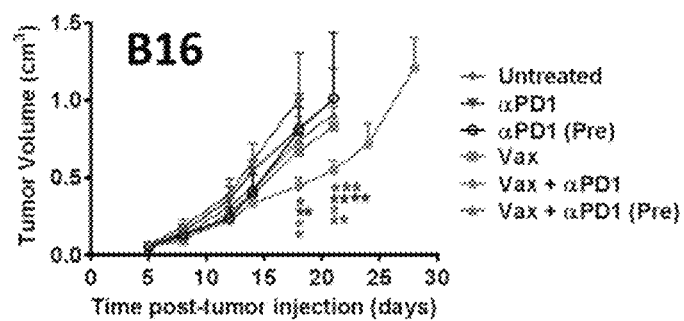
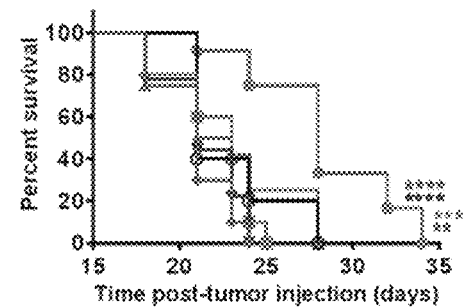
FIGURE 1E
FIGURE 1F
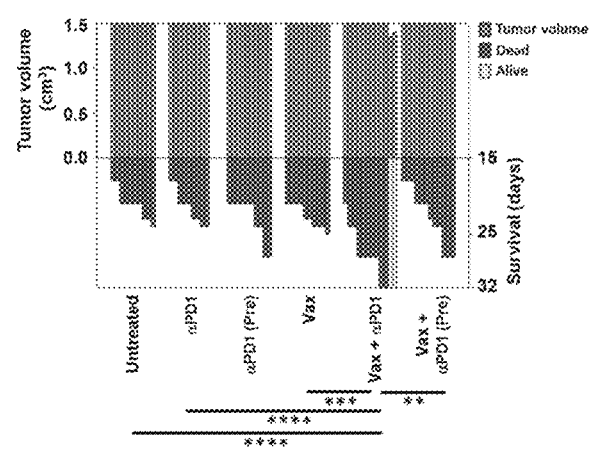
FIGURE 1G

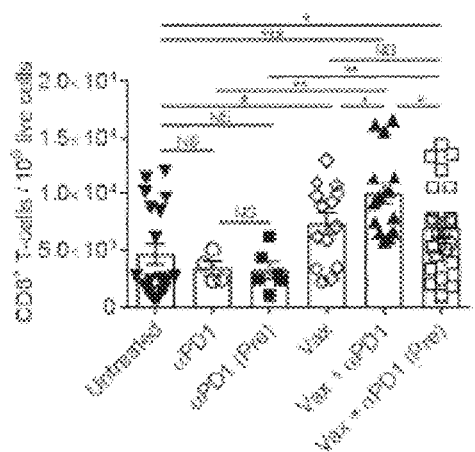
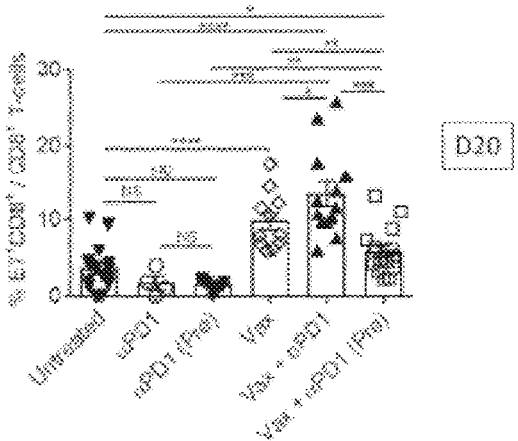
FIGURE 1H          FIGURE 1I
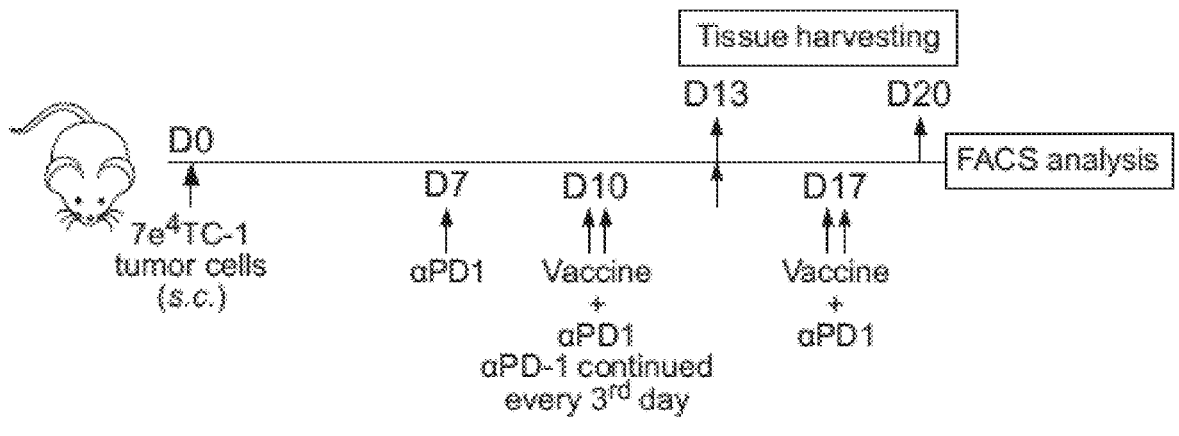
FIGURE 2A
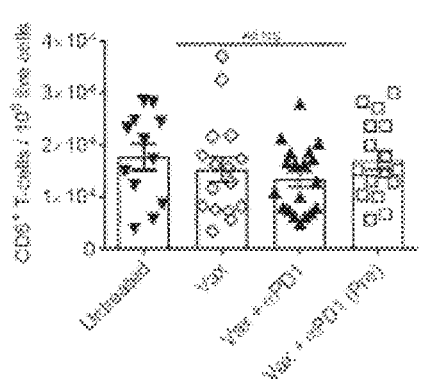
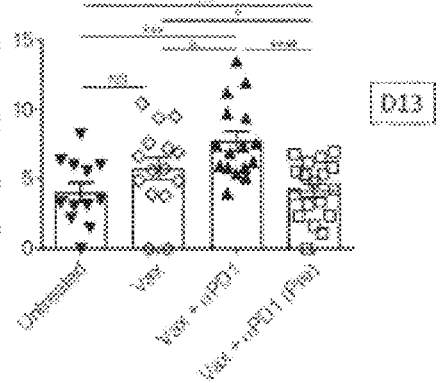
FIGURE 2B          FIGURE 2C

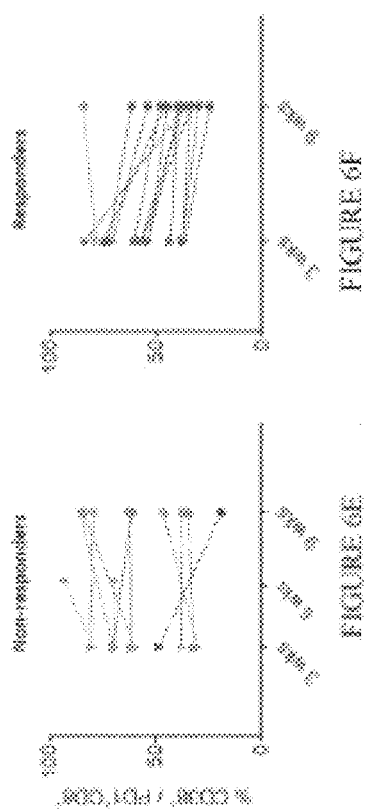
FIGURE 6E
FIGURE 6F
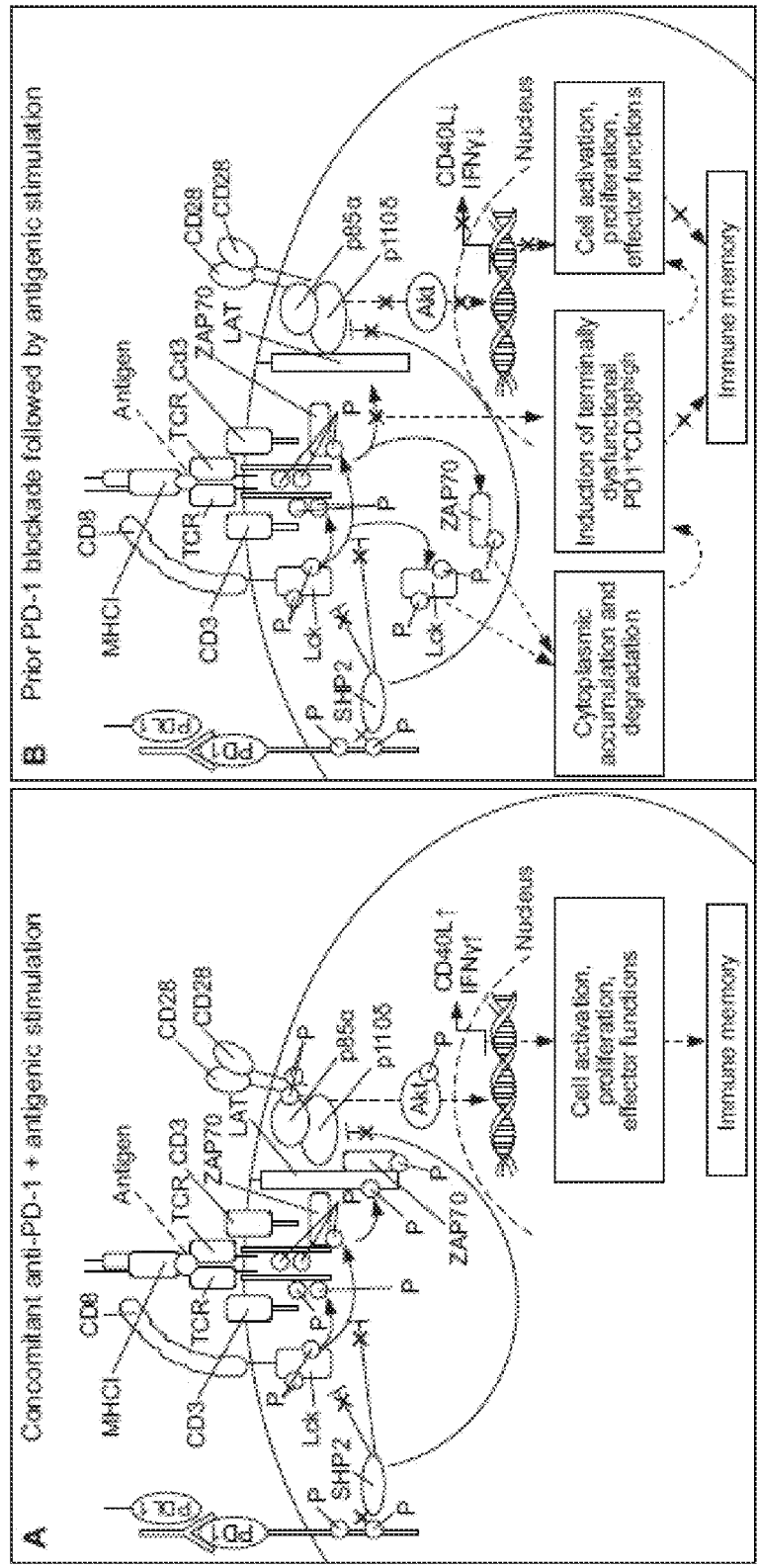
FIGURE 7A
FIGURE 7B

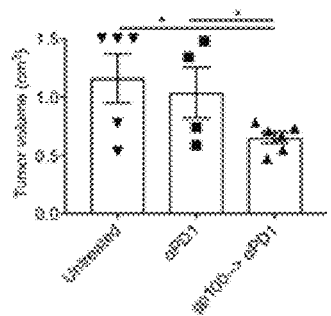
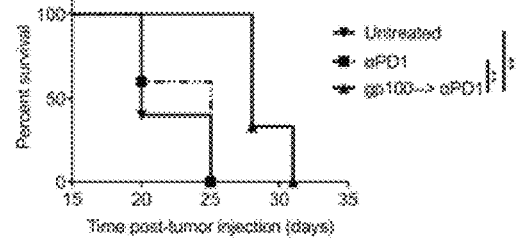
FIGURE 9B  FIGURE 9C
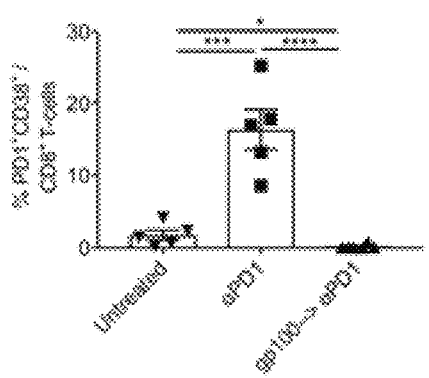
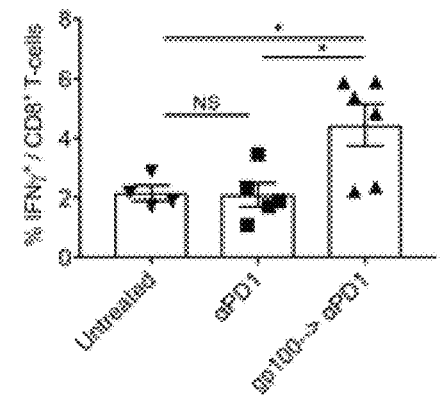
FIGURE 9D  FIGURE 9E
FIGURE 10A
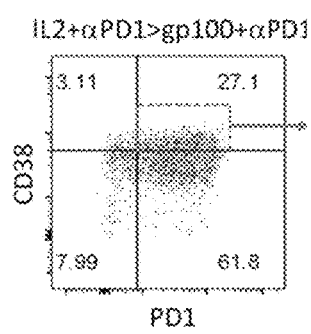
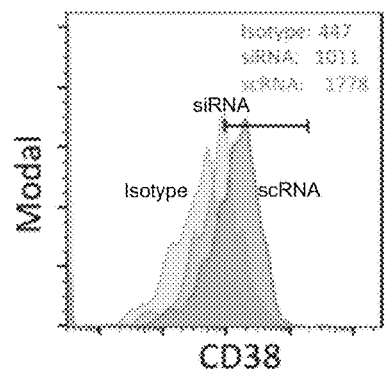
FIGURE 10B  FIGURE 10C

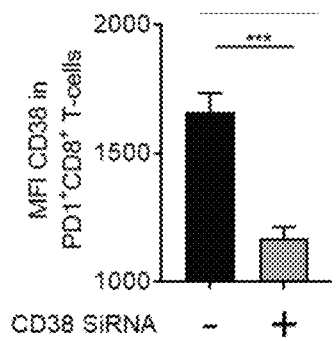
FIGURE 10D • FIGURE 10E
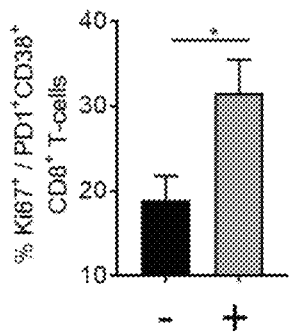 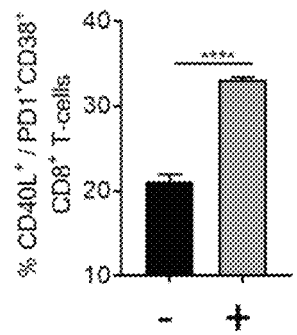 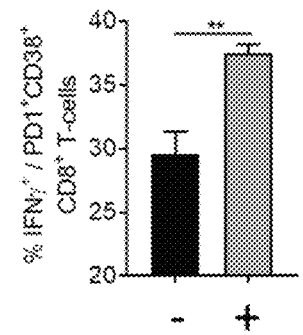
FIGURE 10F • FIGURE 10G • FIGURE 10H
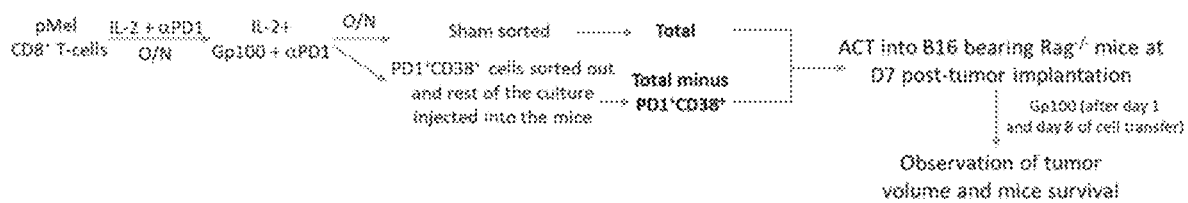
FIGURE 11A
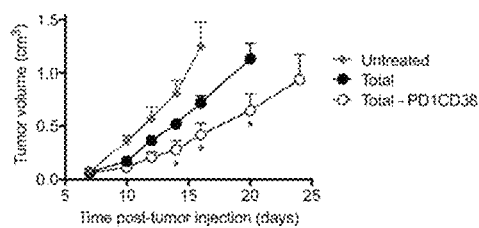 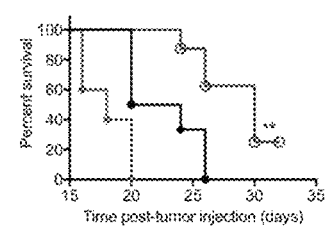
FIGURE 11B • FIGURE 11C

METHODS FOR DETECTING AND REVERSING IMMUNE THERAPY RESISTANCE

CROSS-REFERENCE TO RELATED APPLICATIONS

This invention claims benefit of and priority to U.S. Provisional Patent Application Nos. 62/665,052 filed on May 1, 2018, and 62/775,573 filed on Dec. 5, 2018, both of which are incorporated by reference in their entirety.

REFERENCE TO SEQUENCE LISTING

The Sequence Listing submitted on May 1, 2019, as a text file named "064466_095_seqlisting" created on Apr. 9, 2019, and having a size of 737 MB is hereby incorporated by reference pursuant to 37 C.F.R. § 1.52(e)(5).

TECHNICAL FIELD OF THE INVENTION

This invention is generally related to compositions and methods for detecting and treating anti-PD1 therapy resistance.

BACKGROUND OF THE INVENTION

Immune surveillance provides a balance between immune response and immune tolerance (Corthay, A., *Front Immunol,* 5:197 (2014)). This balance is regulated by a number of costimulatory and immune inhibitory receptor/ligand pairs known collectively as immune checkpoints. Immune checkpoint proteins such as cytotoxic T-lymphocyte antigen-4 (CTLA-4) and programmed death protein 1 (PD-1) play an important role in avoiding self-tissue destruction and consequent autoimmunity (Topalian, S. L., et al., *Cancer Cell,* 27:450-461 (2015)). These immune checkpoint proteins are able to put the brakes on autoimmunity by directly suppressing autoreactive T cells or indirectly enabling various immune suppressive cells like T-regulatory cells. Many of the immune inhibitors are upregulated on infiltrating immune cells during inflammatory conditions, including during tumor development and progression. The ligands for the immune checkpoint proteins, for example programmed death-ligand 1(PD-L1), are also upregulated on a number of cancer cells and immune cells present in the tumor microenvironment. Bolstering the immune attack on tumor cells by suppressing immune checkpoint pathways is the goal of cancer immunotherapy.

The PD-1/PD-L1 pathway has shown promising clinical success as a cancer immunotherapy target. PD-1 signaling is known to mitigate T-cell receptor (TCR)-mediated T-cell activation thereby dampening the effector functions of T cells (Jiang, Y., et al., *Cell Death Dis,* 6:e1792 (2015)). Immune checkpoint inhibitor therapy of cancer patients using anti-PD-1 antibody (Ab) has shown significant clinical response (Page, D B., et al., *Annu Rev Med,* 65:185-202 (2014); Zou, W., et al., *Sci Transl Med,* 8:328rv4 (2016); Hamanishi, J., et al., *Int J Clin Oncol,* 21:462-473 (2016)) albeit only in 10-50% of cancer patients (Kleponis, J., et al., *Cancer Biol Med,* 12:201-208 (2015)). Therefore, to improve the therapeutic outcome, combination strategies using checkpoint Abs and other immune modulatory agents such as vaccines that activate the effector arm of the immune system are currently being widely explored as well as predictive biomarkers.

Therefore, it is an object of the invention to provide compositions that promote or enhance the efficacy of immune checkpoint inhibitor therapy.

It is also an object of the invention to provide compositions and methods for evaluating resistance in patients.

SUMMARY OF THE INVENTION

Compositions and methods for promoting an immune response in a subject in need thereof are provided. One embodiment provides a method of promoting an immune response in a subject in need thereof by depleting dysfunctional T cells in the subject. The dysfunctional T cells that are depleted include, but are not limited to $CD38^+PD-1^+$ T cells, $CD38^+CD8^+$ T-cells, or both. The dysfunctional T cells can be depleted, for example, by administering an antibody or fusion protein that specifically binds to dysfunctional T cells and promotes depletion of the dysfunctional T cells. In one embodiment the antibody is a bispecific antibody. The bispecific antibody can be specific for CD38 and CD8, or it can be specific for CD38 and PD-1. The dysfunctional T cells can be depleted prior to, after, or contemporaneously with the administration of immune checkpoint inhibitor therapy. Typically the immune checkpoint inhibitor therapy is an antibody or fusion protein that immunospecifically binds to immune checkpoint proteins on the surface of cancer cells or immune cells. The immune checkpoint inhibitor therapy can be an anti-PD-1 antibody such as pembrolizumab or nivolumab. Alternatively the immune checkpoint inhibitor therapy can be an anti-PD-L1 antibody such as atezolizumab, avelumab, or durvalumab.

Another embodiment provides a method of reducing tumor burden in a subject in need thereof by (a) quantifying the amount of circulating T cells expressing CD38 in the subject in need thereof, (b) administering to the subject one or more cycles of a composition including an effective amount of a compound that promotes or enhances the depletion of $CD38^+CD8^+$ T cells, $CD38^+PD-1^+$ T cells, or both in the subject, (c) quantifying the amount of circulating T cells expressing CD38 in the subject in need thereof after each cycle of the composition, (d) administering to the subject a cancer vaccine in an amount effective to prime T cells, and (e) administering to the subject a checkpoint inhibitor in an amount effective to induce an immune response to reduce tumor burden, wherein step (d) is initiated when the amount of circulating T cells expressing CD38 measures less than 10% of the total circulating T cells in the subject in need thereof.

Another embodiment provides a composition containing an effective amount of antibody or fusion protein to deplete $CD38^+PD-1^+$ T cells, $CD38^+CD8^+$ T-cells, or both, in combination with a PD-1 or PD-L1 immune checkpoint inhibitor. In one embodiment the depletion antibody is bispecific for CD38 and CD8 or is bispecific for PD-1 and CD38 and the immune checkpoint inhibitor is an anti-PD-1 antibody, an anti-PD-L1 antibody, or both.

Another embodiment provides a method of increasing the efficacy of immune checkpoint inhibitor therapy in a subject in need thereof by administering to the subject a pharmaceutical composition containing an effective amount of a compound that depletes or blocks $CD38^+CD8^+$ T cells, $CD38^+PD-1^+$ T cells, or both by an amount effective to reduce or inhibit resistance to the immune checkpoint inhibitor therapy, and administering to the subject the immune checkpoint inhibitor therapy. In one embodiment the immune checkpoint inhibitor therapy is an anti-PD1/PDL1 therapeutic including, but not limited to an anti-PD-1 antibody, an anti-PD-L1 antibody, or both. The subject in need thereof can have cancer that is selected from the group consisting of bladder, brain, breast, cervical, colo-rectal, esophageal, kidney, liver, lung, nasopharangeal, pancreatic, prostate, skin, stomach, uterine, ovarian, testicular or hematologic cancers. The compound that depletes or blocks $CD38^+CD8^+$ cells can be a bispecific anti-CD38/CD8 antibody. The compound that depletes or blocks $CD38^+PD-1^+$ cells can be a bispecific CD38/PD-1 antibody.

One embodiment provides a method of treating anti-PD1/PDL1 therapy resistance in a subject in need thereof by administering to the subject a composition comprising a CD38 depleting antibody that reduces or eliminates the population of $CD38^+CD8^+$ T cells, $CD38^+PD-1^+$ T cells, or both by an amount effective to reduce or inhibit anti-PD-1/PD-L1 therapy resistance in the subject in need thereof before the subject is administered anti-PD1 therapy. The subject in need thereof can have cancer or cancerous tumors. The CD38 depleting/blocking antibody can be a bispecific antibody that targets CD38 and CD8, or CD38 and PD-1.

Yet another embodiment provides a method of detecting and treating resistance to anti-PD-1/PD-L1 therapy in a subject in need thereof by detecting the presence of $CD38^+CD8^+$ T cells, $CD38^+PD-1^+$ T cells, or $CD38^+PD-1^+CD8^+$ T cells in the sample from the subject and depleting or blocking $CD38^+CD8^+$ T cells, $CD38^+PD-1^+$ T cells, or $CD38^+PD-1^+CD8^+$ T cells from the subject before, during, after or contemporaneously administering an anti-PD-1/PD-L1 therapy to the subject. The sample can be blood, biopsy, or tumor tissue. The subject has cancer. In another embodiment the subject is administered a second therapeutic agent that is selected from the group consisting of vaccines, chemotherapeutic agents, cytokines, chemokines, and radiation therapy.

One embodiment provides a kit for the detection and treatment of anti-PD1/PDL1 resistance in a subject. The kit can contain reagents to detect the presence of $CD38^+CD8^+$ T cells, $CD38^+PD-1^+$ T cells, and $CD38^+PD-1^+CD8+$ cells, a pharmaceutical composition to deplete $CD38^+CD8^+$ T cells, $CD38^+PD-1^+$ T cells, or both from the subject, and an anti-PD-1/PD-L1 immune checkpoint inhibitor therapeutic. In one embodiment, the reagents to detect the presence of $CD38^+CD8^+$ T cells, $CD38^+PD-1^+$ T cells, and $CD38^+PD-1^+CD8^+$ T cells are fluorescently labeled antibodies.

Another embodiment provides a method for reducing tumor burden in a host in need thereof using the methods disclosed herein.

BRIEF DESCRIPTION OF THE DRAWINGS

FIG. 1A is a schematic illustration of the experimental design. Briefly, mice are injected with TC-1 or B16 tumor cells at Day 0 (D0). αPD-1 therapy begins on either Day 7 (D7) or Day 10 (D10) and is represented by light blue arrows. Vaccine (Vax) begins on Day 10 (D10) and is represented by dark purple arrows. FIGS. 1B and 1E are line graphs showing tumor volume (cm³) for TC1 (FIG. 1B) and B16 (FIG. 1E) tumor bearing mice that were untreated, treated with αPD1, pre-treated with PD1, Vax treated, Vax+αPD1 treated, and Vax+PD1 pretreatment. The X-axis represents time post-tumor injection (days) and the Y-axis represents tumor volume (cm³). FIGS. 1C and 1F are survival plots showing percent survival in the mice from FIGS. 1B and 1E, respectively. The X-axis represents time post-tumor injection (days) and the Y-axis represents percent survival. FIGS. 1D and 1G are bar graphs showing tumor volume (cm³) and survival (days) for individual TC1 (FIG. 1D) and B16 (FIG. 1G) tumor bearing mice that were untreated, αPD1 treated, αPD1 pretreated, Vax treated, Vax+αPD1 treated, and Vax+αPD1 pretreated. FIG. 1H is a bar graph showing CD8+ T cells per $10^6$ live cells in tumor bearing mice either untreated, treated with αPD1, pretreated with αPD1, treated with Vax, treated with Vax and αPD1, or pretreated with αPD1 and Vax. FIG. 1I is a bar graph showing percent $E7^+CD8^+$ T cells per total $CD8^+$ T cells in tumor bearing mice either untreated, treated with αPD1, pretreated with αPD1, treated with Vax, treated with Vax and αPD1, or pretreated with αPD1 and Vax.

FIG. 2A is a schematic illustration of the experimental design for FIG. 2. Briefly, mice are injected with TC1 tumor cells at Day 0 (D0). The mice receive αPD1 at Day 7 (D7), Day 10 (D10), and Day 17 (D17) and vaccine on D10 and D17. FIG. 2B is a bar graph showing the number of tumor infiltrating $CD8^+$ T cells per $10^6$ live cells in tumor bearing mice either untreated, treated with αPD1, treated with Vax, treated with Vax and αPD1, pretreated with αPD1 and Vax. FIG. 2C is a bar graph showing percent $E7^+CD8^+$ T cells per total $CD8^+$ T cells in tumor bearing mice either untreated, treated with αPD1, treated with Vax, treated with Vax and αPD1, pretreated with αPD1 and Vax.

FIGS. 6E-6F show flow cytometric measurements of CD38⁺ cells in PD1⁺CD8⁺ T-cells in PBMCs from advanced melanoma patients at 3 weeks and 9 weeks after anti-PD-1 treatment. For two NR patients, data is shown at 6 weeks since samples were not available at week 9. *p≤0.05, **p≤0.01.

FIGS. 7A-7B are a schematic illustration of the proposed mechanism of action.

FIG. 9B is a bar graph showing tumor volume in mice after various treatments in a TC-1 tumor model. FIG. 9C is a line graph showing mouse survival after various treatments in TC-1 tumor model. FIG. 9D is a bar graph showing frequency of PD1⁺CD38$^{high}$ in the TME of TC-1 tumor bearing mice after various treatments. FIG. 9E is a bar graph showing frequency of IFNγ⁺CD8⁺ T-cells in the TME of TC-1 tumor bearing mice after various treatments. The data are at D10 after tumor implantation and are representative of one of two independent experiments. Each dot represents one mouse with n=5/group. Error bars, SEM. $^{NS}$non-significant, *p≤0.05, p≤0.01, *p≤0.001, ****p≤0.0001.

FIG. 10A is a schematic of the experimental outline for pMel-1 CD8⁺ T-cell treatment. FIGS. 10B-10C are a flow cytometry plots of CD38 knock down on PD1⁺CD38⁺ T-cells. FIG. 10D is a bar graph showing MFI expression of CD38 in PD1⁺CD8⁺ T-cells. FIG. 10E is a Western blot showing protein expression of CD38 in PD1⁺CD8⁺ T-cells. FIGS. 10F-10H are bar graphs showing the frequency of Ki67⁺(FIG. 10F), CD40L⁺(FIG. 10G), and IFNγ+(FIG. 10H) in PD1+CD38⁺CD8⁺ T-cell population. Error bars, SEM. $^{NS}$non-significant, *p≤0.05, *p≤0.01, p≤0.001, *p≤0.0001.

FIG. 11A is a schematic of the experimental design for adoptive cell transfer (ACT). FIGS. 11B-11C are line graphs showing tumor growth (FIG. 11B) and survival (FIG. 11C) in B16 tumor-bearing RAG$^{-/-}$ mice following transfer of either total or PD1 CD38⁻ depleted, in vitro activated CD8⁺ T-cells (n=5-8/group; data is representative of two independent experiments). Error bars, SEM. *p≤0.05, **p≤0.01.

DETAILED DESCRIPTION OF THE INVENTION

I. Definitions

Figures 1A, 1B, 1C, 1D:
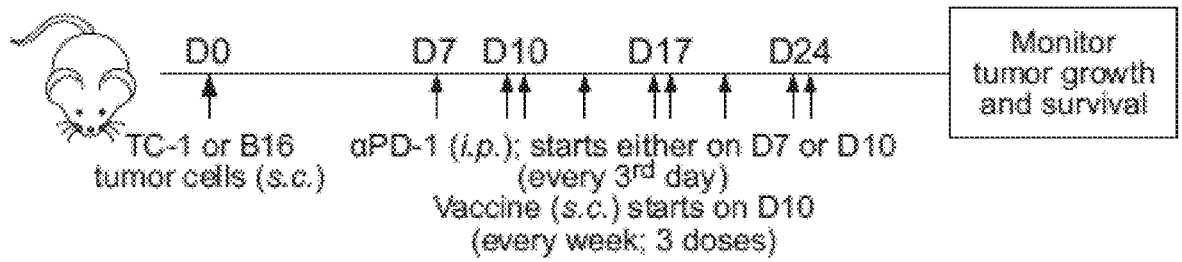

As used herein, the singular forms "a," "an," and "the" include plural referents unless the context clearly dictates otherwise. For example, reference to "the method of treatment" includes reference to equivalent steps and methods known to those skilled in the art, and so forth.

Recitation of ranges of values herein are merely intended to serve as a shorthand method of referring individually to each separate value falling within the range, unless otherwise indicated herein, and each separate value is incorporated into the specification as if it were individually recited herein.

Use of the term "about" is intended to describe values either above or below the stated value in a range of approx. +/−10%; in other embodiments, the values may range in value either above or below the stated value in a range of approx. +/−5%; in other embodiments, the values may range in value either above or below the stated value in a range of approx. +/−2%; in other embodiments, the values may range in value either above or below the stated value in a range of approx. +/−1%. The preceding ranges are intended to be made clear by context, and no further limitation is implied. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The terms "treat," "treating," or "treatment" refers to alleviating, reducing, or inhibiting one or more symptoms or physiological aspects of a disease, disorder, syndrome, or condition. "Treatment" as used herein covers any treatment of a disease in a subject, and includes: (a) preventing the disease or symptom from occurring in a subject which may be predisposed to the disease or symptom, but has not yet been diagnosed as having it; (b) inhibiting the disease symptom, i.e., arresting its development; or (c) relieving the disease symptom, i.e., causing regression of the disease or symptom.

The terms "individual," "subject," and "patient" are used interchangeably herein, and refer to a mammal, including, but not limited to, humans, rodents, such as mice and rats, and other laboratory animals.

As used herein, "programmed death receptor 1", or "PD1", is a cell surface receptor that is predominantly expressed on activated CD4+ and CD8$^+$ T cells as well as on B cells in the periphery. PD1 acts as an immune checkpoint in T cells. It plays a role in down regulating the immune system and promoting self-tolerance by suppressing T cell inflammatory activity. Upon interaction with its ligand PD-L1, PD1 suppresses T cell activation by recruiting SHP-1, which in turn dephosphorylates and inactivates Zap70, a major integrator of T cell receptor-mediated signaling. As a consequence of the interaction of PD-1 and its ligand, T cell proliferation and effector functions such as IFN-γ production and cytotoxic activity are inhibited.

Monoclonal PD-1 antibodies are a type of cancer immunotherapy called immune-checkpoint inhibitors. Instead of accelerating T cell activity like many traditional cancer immunotherapies, immune-checkpoint inhibitors release the brake on the immune system and unleash anti-tumor immune responses.

As used herein, the term "CD38 immunomodulatory agent" refers to cluster of differentiation 38 (CD38) binding moieties including but not limited to antibodies and antigen binding fragments thereof, and CD38 fusion proteins and binding fragments thereof. In one embodiment, CD38 has an amino acid sequence according to UniProtKB-P28907 (CD38_HUMAN) which is incorporated by reference in its entirety. Other names for CD38 include cyclic ADP ribose hydrolase, 2'-phospho-ADP-ribosyl cyclase, 2'-phospho-ADP-ribosyl cyclase/2'-phospho-cyclic-ADP-ribose transferase, 2'-phospho-cyclic-ADP-ribose transferase, ADP-ribosyl cyclase 1, cyclic ADP-ribose hydrolase 1, and T10.

As used herein, the terms "cell depleting" and "cell depletion" refer to the elimination or destruction of a specific cell type from a population of cells. A "cell depleting antibody" is an antibody that binds to a cell and induces depletion or death of the cell. Antibodies can induce cell depletion through various mechanisms including but not limited to the promotion of apoptosis, immune mediated mechanisms such as complement-dependent cytotoxicity, antibody dependent cellular toxicity, and antibody dependent phagocytosis.

"Cell depletion" can occur in vivo or ex vivo. In vivo cell depletion typically occurs through the administration of an antibody to the subject. Ex vivo depletion occurs when a sample of cells are removed from the subject and positive or negative selection techniques are used to select a subset of immune cells to return back to the subject.

As used herein, the term "blocking antibody" refers to an antibody that does not have a reaction when combined with an antigen, but prevents interaction of the antigen with its cognate receptor of which the antibody is against.

As used herein, the term "antibody" is intended to denote an immunoglobulin molecule that possesses a "variable region" antigen recognition site. The term "variable region" is intended to distinguish such domain of the immunoglobulin from domains that are broadly shared by antibodies (such as an antibody Fc domain). The variable region includes a "hypervariable region" whose residues are responsible for antigen binding. The hypervariable region includes amino acid residues from a "Complementarity Determining Region" or "CDR" (i.e., typically at approximately residues 24-34 (L1), 50-56 (L2) and 89-97 (L3) in the light chain variable domain and at approximately residues 27-35 (H1), 50-65 (H2) and 95-102 (H3) in the heavy chain variable domain; Kabat et al., *Sequences of Proteins of Immunological Interest*, 5th Ed. Public Health Service, National Institutes of Health, Bethesda, MD (1991)) and/or those residues from a "hypervariable loop" (i.e., residues 26-32 (L1), 50-52 (L2) and 91-96 (L3) in the light chain variable domain and 26-32 (H1), 53-55 (H2) and 96-101 (H3) in the heavy chain variable domain; Chothia and Lesk, 1987, *J. Mol. Biol.* 196:901-917). "Framework Region" or "FR" residues are those variable domain residues other than the hypervariable region residues as herein defined. The term antibody includes monoclonal antibodies, multi-specific antibodies, human antibodies, humanized antibodies, synthetic antibodies, chimeric antibodies, camelized antibodies (See e.g., Muyldermans et al., 2001, *Trends Biochem. Sci.* 26:230; Nuttall et al., 2000, *Cur. Pharm. Biotech.* 1:253; Reichmann and Muyldermans, 1999, *J. Immunol. Meth.* 231:25; International Publication Nos. WO 94/04678 and WO 94/25591; U.S. Pat. No. 6,005,079), single-chain Fvs (scFv) (see, e.g., see Pluckthun in *The Pharmacology of Monoclonal Antibodies*, vol. 113, Rosenburg and Moore eds. Springer-Verlag, New York, pp. 269-315 (1994)), single chain antibodies, disulfide-linked Fvs (sdFv), intrabodies, and anti-idiotypic (anti-Id) antibodies (including, e.g., anti-Id and anti-anti-Id antibodies to antibodies). In particular, such antibodies include immunoglobulin molecules of any type (e.g., IgG, IgE, IgM, IgD, IgA and IgY), class (e.g., IgG$_1$, IgG$_2$, IgG$_3$, IgG$_4$, IgA$_1$ and IgA$_2$) or subclass.

As used herein, the term "antigen binding fragment" of an antibody refers to one or more portions of an antibody that contain the antibody's Complementarity Determining Regions ("CDRs") and optionally the framework residues that include the antibody's "variable region" antigen recognition site, and exhibit an ability to immunospecifically bind antigen. Such fragments include Fab', F(ab')$_2$, Fv, single chain (ScFv), and mutants thereof, naturally occurring variants, and fusion proteins including the antibody's "variable region" antigen recognition site and a heterologous protein (e.g., a toxin, an antigen recognition site for a different antigen, an enzyme, a receptor or receptor ligand, etc.).

As used herein, the term "fragment" refers to a peptide or polypeptide including an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least 100 contiguous amino acid residues, at least 125 contiguous amino acid residues, at least 150 contiguous amino acid residues, at least 175 contiguous amino acid residues, at least 200 contiguous amino acid residues, or at least 250 contiguous amino acid residues.

The term "binding molecule," as used herein is intended to refer to molecules that specifically interact with and bind to a particular target. The target can comprise a biologic or small (chemical) molecule. The target molecule may define an antigen or antigenic moiety. Examples of a binding molecule include, but are not limited to, antibodies (including monoclonal antibodies, bispecific antibodies, as well as antibody fragments), fusion proteins, and other antigen-binding molecule known to those skilled in the art.

As used herein the term "modulate" relates to a capacity to alter an effect, result, or activity (e.g., signal transduction). Such modulation can be agonistic or antagonistic. Antagonistic modulation can be partial (i.e., attenuating, but not abolishing) or it can completely abolish such activity (e.g., neutralizing). Modulation can include internalization of a receptor following binding of an antibody or a reduction in expression of a receptor on the target cell. Agonistic modulation can enhance or otherwise increase or enhance an activity (e.g., signal transduction). In a still further embodiment, such modulation can alter the nature of the interaction between a ligand and its cognate receptor so as to alter the nature of the elicited signal transduction. For example, the molecules can, by binding to the ligand or receptor, alter the ability of such molecules to bind to other ligands or receptors and thereby alter their overall activity. Preferably, such modulation will provide at least a 10% change in a measurable immune system activity, more preferably, at least a 50% change in such activity, or at least a 2-fold, 5-fold, 10-fold, or still more preferably, at least a 100-fold change in such activity.

The term "substantially," as used in the context of binding or exhibited effect, is intended to denote that the observed effect is physiologically or therapeutically relevant. Thus, for example, a molecule is able to substantially block an activity of a ligand or receptor if the extent of blockage is physiologically or therapeutically relevant (for example if such extent is greater than 60% complete, greater than 70% complete, greater than 75% complete, greater than 80% complete, greater than 85% complete, greater than 90% complete, greater than 95% complete, or greater than 97% complete). Similarly, a molecule is said to have substantially the same immunospecificity and/or characteristic as another molecule, if such immunospecificities and characteristics are greater than 60% identical, greater than 70% identical, greater than 75% identical, greater than 80% identical, greater than 85% identical, greater than 90% identical, greater than 95% identical, or greater than 97% identical).

As used herein, the "co-stimulatory" signals encompass positive co-stimulatory signals (e.g., signals that result in enhancing an activity) and negative co-stimulatory signals (e.g., signals that result in inhibiting an activity).

As used herein, the term "derivative" refers to an antibody or antigen-binding fragment thereof that immunospecifically binds to the same target of a parent or reference antibody but which differs in amino acid sequence from the parent or reference antibody or antigen binding fragment thereof by including one, two, three, four, five or more amino acid substitutions, additions, deletions or modifications relative to the parent or reference antibody or antigen binding fragment thereof. Preferably such derivatives will have substantially the same immunospecificity and/or characteristics, or the same immunospecificity and characteristics as the parent or reference antibody or antigen binding fragment thereof. The amino acid substitutions or additions of such derivatives can include naturally occurring (i.e., DNA-encoded) or non-naturally occurring amino acid residues. The term "derivative" encompasses, for example, chimeric or humanized variants, as well as variants having altered CH1, hinge, CH2, CH3 or CH4 regions, so as to form, for example antibodies, etc., having variant Fc regions that exhibit enhanced or impaired effector or binding characteristics.

As used herein, a "chimeric antibody" is a molecule in which different portions of the antibody are derived from different immunoglobulin molecules such as antibodies having a variable region derived from a non-human antibody and a human immunoglobulin constant region.

As used herein, the term "humanized antibody" refers to an immunoglobulin including a human framework region and one or more CDR's from a non-human (usually a mouse or rat) immunoglobulin. The non-human immunoglobulin providing the CDR's is called the "donor" and the human immunoglobulin providing the framework is called the "acceptor." Constant regions need not be present, but if they are, they should be substantially identical to human immunoglobulin constant regions, i.e., at least about 85-99%, preferably about 95% or more identical. Hence, all parts of a humanized immunoglobulin, except possibly the CDR's, are substantially identical to corresponding parts of natural human immunoglobulin sequences. A humanized antibody is an antibody including a humanized light chain and a humanized heavy chain immunoglobulin. For example, a humanized antibody would not encompass a typical chimeric antibody, because, e.g., the entire variable region of a chimeric antibody is non-human.

As used herein, the term "endogenous concentration" refers to the level at which a molecule is natively expressed (i.e., in the absence of expression vectors or recombinant promoters) by a cell (which cell can be a normal cell, a cancer cell or an infected cell).

As used herein, the terms "treat," "treating," "treatment" and "therapeutic use" refer to the elimination, reduction or amelioration of one or more symptoms of a disease or disorder exacerbated by anti-PD-1 antibodies or an antigen fragment thereof.

As used herein, a "therapeutically effective amount" refers to that amount of a therapeutic agent sufficient to mediate a clinically relevant elimination, reduction or amelioration of such symptoms. An effect is clinically relevant if its magnitude is sufficient to impact the health or prognosis of a recipient subject. A therapeutically effective amount may refer to the amount of therapeutic agent sufficient to delay or minimize the onset of disease, e.g., delay or minimize the spread of cancer. A therapeutically effective amount may also refer to the amount of the therapeutic agent that provides a therapeutic benefit in the treatment or management of a disease.

As used herein, the term "prophylactic agent" refers to an agent that can be used in the prevention of a disorder or disease prior to the detection of any symptoms of such disorder or disease. A "prophylactically effective" amount is the amount of prophylactic agent sufficient to mediate such protection. A prophylactically effective amount may also refer to the amount of the prophylactic agent that provides a prophylactic benefit in the prevention of disease.

As used herein, the term "cancer" refers to a neoplasm or tumor resulting from abnormal uncontrolled growth of cells. As used herein, cancer explicitly includes, leukemias and lymphomas. The term "cancer" refers to a disease involving cells that have the potential to metastasize to distal sites and exhibit phenotypic traits that differ from those of non-cancer cells, for example, formation of colonies in a three-dimensional substrate such as soft agar or the formation of tubular networks or web-like matrices in a three-dimensional basement membrane or extracellular matrix preparation. Non-cancer cells do not form colonies in soft agar and form distinct sphere-like structures in three-dimensional basement membrane or extracellular matrix preparations.

As used herein, an "immune cell" refers to any cell from the hemopoietic origin including, but not limited to, T cells, B cells, monocytes, dendritic cells, and macrophages.

As used herein, "dysfunctional T cells" refer to T cells that do not react to repeated immune stimulation and also fail to generate immune memory. More specifically, the T cells can be $CD38^+CD8^+$ T cells, $CD38^+PD-1^+$ T cells, or $CD38^+PD-1^+CD8^+$ T cells.

As used herein, the terms "immunologic," "immunological" or "immune" response is the development of a beneficial humoral (antibody mediated) and/or a cellular (mediated by antigen-specific T cells or their secretion products) response directed against a peptide in a recipient patient. Such a response can be an active response induced by administration of immunogen or a passive response induced by administration of antibody or primed T-cells. A cellular immune response is elicited by the presentation of polypeptide epitopes in association with Class I or Class II MHC molecules to activate antigen-specific $CD4^+$ T helper cells and/or $CD8^+$ cytotoxic T cells. The response may also involve activation of monocytes, macrophages, NK cells, basophils, dendritic cells, astrocytes, microglia cells, eosinophils, activation or recruitment of neutrophils or other components of innate immunity. The presence of a cell-mediated immunological response can be determined by proliferation assays ($CD4^+$ T cells) or CTL (cytotoxic T lymphocyte) assays. The relative contributions of humoral and cellular responses to the protective or therapeutic effect of an immunogen can be distinguished by separately isolating antibodies and T-cells from an immunized syngeneic animal and measuring protective or therapeutic effect in a second subject.

As used herein, an "immunogenic agent" or "immunogen" is capable of inducing an immunological response against itself on administration to a mammal, optionally in conjunction with an adjuvant.

As used herein, the terms "individual," "host," "subject, and "patient" are used interchangeably herein, and refer to a mammal, including, but not limited to, humans, rodents, such as mice and rats, and other laboratory animals.

As used herein, the term "polypeptide" refers to a chain of amino acids of any length, regardless of modification (e.g., phosphorylation or glycosylation). The term polypeptide includes proteins and fragments thereof. The polypeptides can be "exogenous," meaning that they are "heterologous," i.e., foreign to the host cell being utilized, such as human polypeptide produced by a bacterial cell. Polypeptides are disclosed herein as amino acid residue sequences. Those sequences are written left to right in the direction from the amino to the carboxy terminus.

In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

As used herein, the term "variant" refers to a polypeptide or polynucleotide that differs from a reference polypeptide or polynucleotide, but retains essential properties. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A substituted or inserted amino acid residue may or may not be one encoded by the genetic code. A variant of a polypeptide may be naturally occurring such as an allelic variant, or it may be a variant that is not known to occur naturally.

Modifications and changes can be made in the structure of the polypeptides of the disclosure and still obtain a molecule having similar characteristics as the polypeptide (e.g., a conservative amino acid substitution). For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence and nevertheless obtain a polypeptide with like properties.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and cofactors. It is known in the art that an amino acid can be substituted by another amino acid having a similar hydropathic index and still obtain a functionally equivalent polypeptide. In such changes, the substitution of amino acids whose hydropathic indices are within +2 is preferred, those within +1 are particularly preferred, and those within +0.5 are even more particularly preferred.

Substitution of like amino acids can also be made on the basis of hydrophilicity, particularly where the biological functional equivalent polypeptide or peptide thereby created is intended for use in immunological embodiments. The following hydrophilicity values have been assigned to amino acid residues: arginine (+3.0); lysine (+3.0); aspartate (+3.0+1); glutamate (+3.0+1); serine (+0.3); asparagine (+0.2); glutamine (+0.2); glycine (0); proline (−0.5+1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within +2 is preferred, those within +1 are particularly preferred, and those within +0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various foregoing characteristics into consideration are well known to those of skill in the art and include (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Trp: Tyr), (Tyr: Trp, Phe), and (Val: Ile, Leu). Embodiments of this disclosure thus contemplate functional or biological equivalents of a polypeptide as set forth above. In particular, embodiments of the polypeptides can include variants having about 50%, 60%, 70%, 80%, 90%, 95%, 96%, 97%, 98%, 99%, or more sequence identity to the polypeptide of interest.

The term "percent (%) sequence identity" is defined as the percentage of nucleotides or amino acids in a candidate sequence that are identical with the nucleotides or amino acids in a reference nucleic acid sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

For purposes herein, the % sequence identity of a given nucleotides or amino acids sequence C to, with, or against a given nucleic acid sequence D (which can alternatively be phrased as a given sequence C that has or comprises a certain % sequence identity to, with, or against a given sequence D) is calculated as follows: 100 times the fraction W/Z, where W is the number of nucleotides or amino acids scored as identical matches by the sequence alignment program in that program's alignment of C and D, and where Z is the total number of nucleotides or amino acids in D. It will be appreciated that where the length of sequence C is not equal to the length of sequence D, the % sequence identity of C to D will not equal the % sequence identity of D to C.

As used herein, the term "pharmaceutically acceptable carrier" encompasses any of the standard pharmaceutical carriers, such as a phosphate buffered saline solution, water and emulsions such as an oil/water or water/oil emulsion, and various types of wetting agents.

II. Methods of Detecting and Treating Anti-PD1/PDL1 Therapy Resistance

Disclosed herein are compositions and methods for improving the efficacy of checkpoint inhibitor therapy. PD-1/PD-L1 therapy is highly successful for some cancer patients however, a large subset of patients are resistant to anti-PD-1/PD-L1 therapy. One embodiment provides a method of increasing the efficacy of anti-PD-1/PD-L1 therapy by inhibiting or reducing the expression of CD38 on CD8 T cells. Compositions for inhibiting or reducing the expression of CD38 on CD8 T cells include but are not limited to antibodies including depleting antibodies, fusion proteins, and small molecule inhibitors. In one embodiment, the disclosed compositions can be administered to the subject in need thereof before PD-1/PD-L1 therapy to increase the efficacy of the PD-1/PDL1 therapy and reduce or eliminate resistance to PD-1/PD-L1 therapy.

In another embodiment, the amount of circulating CD38 expressing $CD8^+$ T cells out of the entire population of $CD8^+$ T cells can be used to predict and monitor resistance to checkpoint inhibitor therapy. Compositions for inhibiting or reducing the expression of CD38 on $CD8^+$ T cells can be administered to the subject until the amount of circulating CD38 expressing $CD8^+$ T cells is below 10% of the entire population of $CD8^+$ T cells. In one embodiment, when the number of circulating CD38 expressing $CD8^+$ T cells is below 10% of the total circulating $CD8^+$ T cells, the subject is administered checkpoint inhibitor therapy. In another embodiment, when the number of circulating CD38 expressing $CD8^+$ T cells is below 4% of the total circulating $CD8^+$ T cells, the subject is administered checkpoint inhibitor therapy.

A. $CD38^+CD8^+$, $CD38^+PD-1^+$, and $PD1^+CD38^+CD8^+$ T-Cell Depletion

Methods of treating resistance to anti-PD-1/PD-L1 therapy in a subject are provided. Typically, the methods include administering to a subject an effective amount of one or more compositions including a compound that inhibits or depletes $CD38^+CD8^+$ T cells or $CD38^+PD-1+$ T cells. Without being bound to any one theory, it is believed that the presence of dysfunctional $CD38^+CD8^+$ T cells, $CD38^+PD-1^+$ T cells, or $CD38^+PD-1^+CD8$ T cells in the tumor microenvironment of a subject is a predictive biomarker of anti-PD-1 therapy failure. The terminally dysfunctional T cells fail to get activated, do not produce IFNγ, undergo apoptosis, and do not generate memory even after subsequent antigenic rechallenge with anti-PD1. The disclosed compositions can be administered to a subject in need thereof in an effective amount to deplete or inhibit the dysfunctional $CD38^+CD8^+$ T cells, $CD38^+PD-1^+$ T cells, or $CD38^+PD-1^+CD8^+$ T cells, thus inhibiting or reducing immune checkpoint inhibitor therapy resistance.

In one embodiment, the disclosed methods can be used to decrease tumor burden in a subject in need thereof. Tumor burden can be reduced in a subject in need thereof by depleting $CD38^+CD8^+$ T cells, $CD38^+PD-1^+$ T cells, or both in the subject before administration of an anti-PD-1 antibody, an anti-PD-L1 antibody, or both. Without being bound to any one theory, it is believed that by depleting the terminally dysfunctional $CD38^+CD8^+$, $CD38^+PD-1^+$, and $CD38^+PD-1^+CD8^+$ T cells the efficacy of anti-PD-1/PD-L1 therapy can be improved. By enriching the population of anti-PD-1/PD-L1 responsive T cells, the response to anti-PD-1/PD-L1 therapy can be increased thus inducing cell death within the tumor.

1. Therapeutic Strategy

In some embodiments, the disclosed compositions that inhibit or deplete $CD38^+CD8^+$ T cells or $CD38^+PD-1^+$ T cells are administered directly to the subject. In some embodiments, the disclosed compositions that inhibit or deplete $CD38^+CD8^+$ T cells or $CD38^+PD-1^+$ T cells are contacted with cells (e.g., immune cells) ex vivo, and the treated cells are administered to the subject (e.g., adoptive transfer). The antibody or antigen binding fragment thereof can enable a more robust immune response to be possible. The disclosed compositions are useful to deplete terminally dysfunctional immune cells from the tumor microenvironment so that the efficacy of anti-PD-1/PD-L1 therapy is improved.

In one embodiment, the presence of $CD38^+CD8^+$ T cells, $CD38^+PD-1^+$ T cells, or $CD38^+PD-1^+CD8^+$ T cells is determined in the subject prior to administration of anti-PD-1/PD-L1 therapy. A sample can be obtained from the subject. The sample can be blood or tumor tissue. In one embodiment, if $CD38^+CD8^+$ T cells, $CD38^+PD-1^+$ T cells, or $CD38^+PD-1^+CD8^+$ T cells are present in the sample then the subject is diagnosed as resistant to anti-PD-1/PD-L1 therapy. Resistant subjects can be administered the disclosed compositions in an effective amount to deplete the dysfunctional $CD38^+CD8^+$ T cells, $CD38^+PD-1^+$ T cells, or $CD38^+PD-1^+CD8^+$ T cells, thus enriching the population of anti-PD-1/PD-L1 responsive T cells. After the dysfunctional cells have been depleted, the subjects can be administered an anti-PD-1/PD-L1 therapy. In another embodiment, resistant subjects are administered a therapy other than anti-PD-1/PD-L1, such as anti-CTLA4 therapy.

In another embodiment, the presence of $CD38^+CD8^+$ T cells, $CD38^+PD-1^+$ T cells, or $CD38^+PD-1^+CD8^+$ T cells in a subject after the administration of anti-PD-1/PD-L1 therapy is an indication of the development of resistance to the therapy. A sample can be obtained from the subject after administration of anti-PD-1/PD-L1 therapy to determine the presence of $CD38^+CD8^+$ T cells, $CD38^+PD-1^+$ T cells, or $CD38^+PD-1^+CD8^+$ T cells. If these cells are detected then the subject can be administered the disclosed compositions in an effective amount to deplete the dysfunctional $CD38^+CD8^+$ T cells, $CD38^+PD-1^+$ T cells, or $CD38^+PD-1^+CD8^+$ T cells. In one embodiment, the presence of $CD38^+CD8^+$ T cells, $CD38^+PD-1^+$ T cells, or $CD38^+PD-1^+CD8^+$ T cells is monitored throughout the subject's anti-PD-1/PD-L1 therapy regimen.

Without being bound to any one theory it is believed that expression of CD38 determines functionality of PD-1 expressing $CD8^+$ T-cells. In one embodiment, knockdown or depletion of CD38 enhances cell activation, proliferation and effector functions of $CD8^+$ T cells.

a. anti-PD-1/PDL1 Therapy

In one embodiment, subjects in need thereof are administered an anti-CD8/CD38 depleting/blocking antibody before being administered anti-PD-1/PD-L1 therapy. In another embodiment, the anti-CD8/CD38 depleting/blocking antibody and the anti-PD-1/PD-L1 therapy are administered in alternation. The anti-CD8/CD38 depleting/blocking antibody can be administered to the subject 1, 2, 3, 4, 5, or more than 5 days before the anti-PD-1/PD-L1 therapy.

Suitable PD-1 antagonists are described in U.S. Pat. Nos. 8,114,845, 8,609,089, and 8,709,416, which are specifically incorporated by reference herein in their entities, and include compounds or agents that either bind to and block a ligand of PD-1 to interfere with or inhibit the binding of the ligand to the PD-1 receptor, or bind directly to and block the PD-1 receptor without inducing inhibitory signal transduction through the PD-1 receptor.

In some embodiments, the PD-1 receptor antagonist binds directly to the PD-1 receptor without triggering inhibitory signal transduction and also binds to a ligand of the PD-1 receptor to reduce or inhibit the ligand from triggering signal transduction through the PD-1 receptor. By reducing the number and/or amount of ligands that bind to PD-1 receptor and trigger the transduction of an inhibitory signal, fewer cells are attenuated by the negative signal delivered by PD-1 signal transduction and a more robust immune response can be achieved.

It is believed that PD-1 signaling is driven by binding to a PD-1 ligand in close proximity to a peptide antigen presented by major histocompatibility complex (MHC) (see, for example, Freeman, *Proc. Natl. Acad. Sci. U. S. A,* 105:10275-10276 (2008)). Therefore, proteins, antibodies or small molecules that prevent co-ligation of PD-1 and TCR on the T cell membrane are also useful PD-1 antagonists.

In some embodiments, the PD-1 receptor antagonists are small molecule antagonists or antibodies that reduce or interfere with PD-1 receptor signal transduction by binding to ligands of PD-1 or to PD-1 itself, thereby not triggering inhibitory signal transduction through the PD-1 receptor.

Other PD-1 antagonists contemplated by the methods of this invention include antibodies that bind to PD-1 or ligands of PD-1, and other antibodies.

Suitable anti-PD-1 antibodies include, but are not limited to, those described in the following U.S. Pat. Nos. 7,332,582, 7,488,802, 7,521,051, 7,524,498, 7,563,869, 7,981,416, 8,088,905, 8,287,856, 8,580,247, 8,728,474, 8,779,105, 9,067,999, 9,073,994, 9,084,776, 9,205,148, 9,358,289, 9,387,247, 9,492,539, and 9,492,540 all of which are incorporated by reference in their entireties.

See also Berger et al., *Clin. Cancer Res.,* 14:30443051 (2008).

Exemplary anti-PD-L1 antibodies include, but are not limited to, those described in the following U.S. Pat. Nos. 8,383,796, 9,102,725, 9,273,135, 9,393,301, and 9,580,507 all of which are specifically incorporated by reference herein in their entirety.

For anti-PD-L2 antibodies see U.S. Pat. Nos. 7,411,051, 7,052,694, 7,390,888, 8,188,238, and 9,255,147.

Other exemplary PD-1 receptor antagonists include, but are not limited to PD-L2 polypeptides, including homologs and variants of these, as well as active fragments of any of the foregoing, and fusion proteins that incorporate any of these. In some embodiments, the fusion protein includes the soluble portion of PD-L2 coupled to the Fc portion of an antibody, such as human IgG, and does not incorporate all or part of the transmembrane portion of human PD-L2.

The PD-1 antagonist can also be a fragment of a mammalian PD-1, for example from mouse or primate, such as a human, wherein the fragment binds to and blocks PD-1 but does not result in inhibitory signal transduction through PD-1. The fragments can also be part of a fusion protein, for example an Ig fusion protein.

Other useful polypeptides PD-1 antagonists include those that bind to the ligands of the PD-1 receptor. These include the PD-1 receptor protein, or soluble fragments thereof, which can bind to the PD-1 ligands, such as PD-L1 or PD-L2, and prevent binding to the endogenous PD-1 receptor, thereby preventing inhibitory signal transduction. PD-1 has also been shown to bind the protein B7.1 (Butte et al., Immunity, Vol. 27, pp. 111-122, (2007)). Such fragments also include the soluble ECD portion of the PD-1 protein that includes mutations, such as the A99L mutation, that increases binding to the natural ligands (Molnar et al., PNAS, 105:10483-10488 (2008)). B7-1 or soluble fragments thereof, which can bind to the B7-H1 ligand and prevent binding to the endogenous PD-1 receptor, thereby preventing inhibitory signal transduction, are also useful.

PD-1 and PD-L1 anti-sense nucleic acids, both DNA and RNA, as well as siRNA molecules can also be PD-1 antagonists. Such anti-sense molecules prevent expression of PD-1 on T cells as well as production of T cell ligands, such as PD-L1 and/or PD-L2. For example, siRNA (for example, of about 21 nucleotides in length, which is specific for the gene encoding PD-1, or encoding a PD-1 ligand, and which oligonucleotides can be readily purchased commercially) complexed with carriers, such as polyethyleneimine (see Cubillos-Ruiz et al., J. Clin. Invest. 119(8): 2231-2244 (2009), are readily taken up by cells that express PD-1 as well as ligands of PD-1 and reduce expression of these receptors and ligands to achieve a decrease in inhibitory signal transduction in T cells, thereby activating T cells.

b. Additional Therapeutics

The disclosed methods can optionally include a step of administering an additional therapeutic agent. Exemplary additional therapeutic agents include, but are not limited to, cytokines, chemotherapeutic agents, radionuclides, radiation, other immunotherapeutics, enzymes, antibiotics, antivirals (especially protease inhibitors alone or in combination with nucleosides for treatment of HIV or Hepatitis B or C), anti-parasites (helminths, protozoans), growth factors, growth inhibitors, hormones, hormone antagonists, antibodies and bioactive fragments thereof (including humanized, single chain, and chimeric antibodies), antigen and vaccine formulations (including adjuvants), peptide drugs, anti-inflammatories, ligands that bind to Toll-Like Receptors (including but not limited to CpG oligonucleotides) to activate the innate immune system, molecules that mobilize and optimize the adaptive immune system, other molecules that activate or up-regulate the action of cytotoxic T lymphocytes, natural killer cells and helper T-cells, and other molecules that deactivate or down-regulate suppressor or regulatory T-cells.

The disclosed methods can optionally include a step of administering to the subject a chemotherapeutic agent. Representative chemotherapeutic agents include, but are not limited to amsacrine, bleomycin, busulfan, capecitabine, carboplatin, carmustine, chlorambucil, cisplatin, cladribine, clofarabine, crisantaspase, cyclophosphamide, cytarabine, dacarbazine, dactinomycin, daunorubicin, docetaxel, doxorubicin, epirubicin, etoposide, fludarabine, fluorouracil, gemcitabine, hydroxycarbamide, idarubicin, ifosfamide, irinotecan, leucovorin, liposomal doxorubicin, liposomal daunorubicin, lomustine, melphalan, mercaptopurine, mesna, methotrexate, mitomycin, mitoxantrone, oxaliplatin, paclitaxel, pemetrexed, pentostatin, procarbazine, raltitrexed, satraplatin, streptozocin, tegafur-uracil, temozolomide, teniposide, thiotepa, tioguanine, topotecan, treosulfan, vinblastine, vincristine, vindesine, vinorelbine, or a combination thereof. Representative pro-apoptotic agents include, but are not limited to fludarabinetaurosporine, cycloheximide, actinomycin D, lactosylceramide, 15d-PGJ(2) and combinations thereof.

2. Subjects to be Treated a. Treatment of Cancer

The methods and compositions disclosed herein are useful in the treatment of a variety of cancers or other abnormal proliferative diseases, including (but not limited to) the following: carcinoma, including that of the bladder, breast, colon, kidney, liver, lung, ovary, pancreas, stomach, cervix, thyroid and skin; including squamous cell carcinoma; hematopoietic tumors of lymphoid lineage, including leukemia, acute lymphocytic leukemia, acute lymphoblastic leukemia, B-cell lymphoma, T-cell lymphoma, Berketts lymphoma; hematopoietic tumors of myeloid lineage, including acute and chronic myelogenous leukemias and promyelocytic leukemia; tumors of mesenchymal origin, including fibrosarcoma and rhabdomyoscarcoma; other tumors, including melanoma, seminoma, tetratocarcinoma, neuroblastoma and glioma; tumors of the central and peripheral nervous system, including astrocytoma, neuroblastoma, glioma, and schwannomas; tumors of mesenchymal origin, including fibrosarcoma, rhabdomyoscarama, and osteosarcoma; and other tumors, including melanoma, xenoderma pegmentosum, keratoactanthoma, seminoma, thyroid follicular cancer and teratocarcinoma.

Cancers caused by aberrations in apoptosis can also be treated by the disclosed methods and compositions. Such cancers may include, but are not be limited to, follicular lymphomas, carcinomas with p53 mutations, hormone dependent tumors of the breast, prostate and ovary, and precancerous lesions such as familial adenomatous polyposis, and myelodysplastic syndromes.

In specific embodiments, malignancy or dysproliferative changes (such as metaplasias and dysplasias), or hyperproliferative disorders, are treated or prevented by the methods and compositions in the ovary, bladder, breast, colon, lung, skin, pancreas, or uterus. In other specific embodiments, sarcoma, melanoma, or leukemia is treated or prevented by the methods and compositions.

Specific cancers and related disorders that can be treated or prevented by methods and compositions disclosed herein include, but are not limited to, leukemias including, but not limited to, acute leukemia, acute lymphocytic leukemia, acute myelocytic leukemias such as myeloblastic, promyelocytic, myelomonocytic, monocytic, erythroleukemia leukemias and myelodysplastic syndrome, chronic leukemias such as but not limited to, chronic myelocytic (granulocytic) leukemia, chronic lymphocytic leukemia, hairy cell leukemia; polycythemia vera; lymphomas such as, but not limited to, Hodgkin's disease or non-Hodgkin's disease lymphomas (e.g., diffuse anaplastic lymphoma kinase (ALK) negative, large B-cell lymphoma (DLBCL); diffuse anaplastic lymphoma kinase (ALK) positive, large B-cell lymphoma (DLBCL); anaplastic lymphoma kinase (ALK) positive, ALK+ anaplastic large-cell lymphoma (ALCL), acute myeloid lymphoma (AML)); multiple myelomas such as, but not limited to, smoldering multiple myeloma, nonsecretory myeloma, osteosclerotic myeloma, plasma cell leukemia, solitary plasmacytoma and extramedullary plasmacytoma; Waldenstrom's macroglobulinemia; monoclonal gammopathy of undetermined significance; benign monoclonal gammopathy; heavy chain disease; bone and connective tissue sarcomas such as, but not limited to, bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; brain tumors including but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma; breast cancer including, but not limited to, adenocarcinoma, lobular (small cell) carcinoma, intraductal carcinoma, medullary breast cancer, mucinous breast cancer, tubular breast cancer, papillary breast cancer, Paget's disease, and inflammatory breast cancer; adrenal cancer, including but not limited to, pheochromocytom and adrenocortical carcinoma; thyroid cancer such as but not limited to papillary or follicular thyroid cancer, medullary thyroid cancer and anaplastic thyroid cancer; pancreatic cancer, including but not limited to, insulinoma, gastrinoma, glucagonoma, vipoma, somatostatin-secreting tumor, and carcinoid or islet cell tumor; pituitary cancers including but not limited to, Cushing's disease, prolactin-secreting tumor, acromegaly, and diabetes insipius; eye cancers including, but not limited to, ocular melanoma such as iris melanoma, choroidal melanoma, and cilliary body melanoma, and retinoblastoma; vaginal cancers, including, but not limited to, squamous cell carcinoma, adenocarcinoma, and melanoma; vulvar cancer, including but not limited to, squamous cell carcinoma, melanoma, adenocarcinoma, basal cell carcinoma, sarcoma, and Paget's disease; cervical cancers including, but not limited to, squamous cell carcinoma, and adenocarcinoma; uterine cancers including, but not limited to, endometrial carcinoma and uterine sarcoma; ovarian cancers including, but not limited to, ovarian epithelial carcinoma, borderline tumor, germ cell tumor, and stromal tumor; esophageal cancers including, but not limited to, squamous cancer, adenocarcinoma, adenoid cyctic carcinoma, mucoepidermoid carcinoma, adenosquamous carcinoma, sarcoma, melanoma, plasmacytoma, verrucous carcinoma, and oat cell (small cell) carcinoma; stomach cancers including, but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers including, but not limited to, hepatocellular carcinoma and hepatoblastoma, gallbladder cancers including, but not limited to, adenocarcinoma; cholangiocarcinomas including, but not limited to, papillary, nodular, and diffuse; lung cancers including but not limited to, non-small cell lung cancer, squamous cell carcinoma (epidermoid carcinoma), adenocarcinoma, large-cell carcinoma and small-cell lung cancer; testicular cancers including, but not limited to, germinal tumor, seminoma, anaplastic, classic (typical), spermatocytic, nonseminoma, embryonal carcinoma, teratoma carcinoma, choriocarcinoma (yolk-sac tumor), prostate cancers including, but not limited to, adenocarcinoma, leiomyosarcoma, and rhabdomyosarcoma; penal cancers; oral cancers including, but not limited to, squamous cell carcinoma; basal cancers; salivary gland cancers including, but not limited to, adenocarcinoma, mucoepidermoid carcinoma, and adenoidcystic carcinoma; pharynx cancers including, but not limited to, squamous cell cancer, and verrucous; skin cancers including, but not limited to, basal cell carcinoma, squamous cell carcinoma and melanoma, superficial spreading melanoma, nodular melanoma, lentigo malignant melanoma, acral lentiginous melanoma; kidney cancers including, but not limited to, renal cell cancer, adenocarcinoma, hypernephroma, fibrosarcoma, transitional cell cancer (renal pelvis and/or uterer); Wilms' tumor; bladder cancers including, but not limited to, transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al., 1985, Medicine, 2d Ed., J.B. Lippincott Co., Philadelphia and Murphy et al., 1997, Informed Decisions: The Complete Book of Cancer Diagnosis, Treatment, and Recovery, Viking Penguin, Penguin Books U.S.A., Inc., United States of America).

III. Compositions and Methods for CD38 Cell Depletion

Disclosed herein are compositions and methods for improving the effectiveness of anti-PD-1/PD-L1 therapy by depleting or inhibiting CD38 expressing $CD8^+$ T cells in patients in need thereof. It has been discovered that the presence of $CD38^+PD-1^+CD8^+$ T cells in the tumor microenvironment contributes to the development of anti-PD-1/PD-L1 therapy resistance. Additionally, the presence of $CD38^+$ $PD-1^+CD8^+$ T cells in the blood of patients that have already received anti-PD-1/PD-L1 therapy is a marker of the development of immune checkpoint inhibitor therapy resistance. Methods of depleting or inhibiting specific cell populations are known in the art and include but are not limited to immunomodulatory agents, fluorescent activated cell sorting, magnetic bead separation, and apheresis.

A. CD38/CD8 Immunomodulatory Agents

One embodiment provides a method of improving anti-PD-1/PD-L1 therapy by using compositions that immunospecifically bind to CD38 on the surface of CD8 T cells to deplete $CD38^+CD8^+$ T cells and reduce or inhibit anti-PD-1/PD-L1 therapy resistance. In another embodiment, the compositions immunospecifically bind to CD38 and block the interaction of CD38 with its receptor. In one embodiment, the CD38 and CD8 immunospecific compositions are bispecific compositions. Exemplary immunomodulatory agents include but are not limited to antibodies, antigen-binding fragment, proteins, peptides, fusion proteins, or small molecules.

1. CD38

Cluster of differentiation 38 (CD38) is a multifunctional cell surface protein that has receptor and enzyme functions. CD38 has been shown to play a critical role in diverse immune functions including T cell activation, neutrophil chemotaxis, dendritic cell migration, and monocyte chemokine production. It was originally recognized as a differentiation and activation marker of lymphocytes but has more recently been used as a phenotypic marker in T- and B-cell malignancies because of its high expression in plasma cell tumors.

CD38 is expressed on numerous cells types of the hematopoietic system, such as lymphocytes, myeloid cells, natural killer (NK) cells, platelets, and erythrocytes, as well as in solid tissues, including various cell types of the brain, the eye, in pancreatic islet cells, smooth muscle cells, and osteoclasts and osteoblasts. The expression of CD38 on hematopoietic cells depends on differentiation and activation status of the cell. Lineage committed hematopoietic cells express CD38, while it is lost by mature cells, and expressed again in activated lymphocytes.

The expression of CD38 has been associated with various diseases including but not limited to HIV infection, autoimmune diseases, type II diabetes, osteoporosis, and cancer, more specifically hematological cancer.

Sequences for human CD38 are known in the arts. For example, the amino acid sequence for human CD38 is as follows:

UniProt Accession P28907-1 which is incorporated by reference in its entirety.

```
                                          (SEQ ID NO: 1)
         10         20         30         40
MANCEFSPVS GDKPCCRLSR RAQLCLGVSI LVLILVVVLA 50         60         70         80
VVVPRWRQQW SGPGTTKRFP ETVLARCVKY TEIHPEMRHV 90        100        110        120
DCQSVWDAFK GAFISKHPCN ITEEDYQPLM KLGTQTVPCN 130        140        150        160
KILLWSRIKD LAHQFTQVQR DMFTLEDTLL GYLADDLTWC 170        180        190        200
GEFNTSKINY QSCPDWRKDC SNNPVSVFWK TVSRRFAEAA 210        220        230        240
CDVVHVMLNG SRSKIFDKNS TFGSVEVHNL QPEKVQTLEA 250        260        270        280
WVIHGGREDS RDLCQDPTIK ELESIISKRN IQFSCKNIYR 290        300
PDKFLQCVKN PEDSSCTSEI
```

One embodiment provides an immunomodulatory agent that specifically binds to SEQ ID NO: 1 or a functional fragment thereof and modulates CD38 mediated signal transduction. In another embodiment, the immunomodulatory agent depletes CD38+ cells.

Amino acids 43-300 of SEQ ID NO: 1 represent the ECD of human CD38 and has the following sequence:

```
                                          (SEQ ID NO: 2)
VPRWRQQWSGPGTTKRFPETVLARCVKYTEIHPEMRHVDCQSVWDAFKG

AFISKHPCNITEEDYQPLMKLGTQTVPCNKILLWSRIKDLAHQFTQVQR

DMFTLEDTLLGYLADDLTWCGEFNTSKINYQSCPDWRKDCSNNPVSVFW

KTVSRRFAEAACDVVHVMLNGSRSKIFDKNSTFGSVEVHNLQPEKVQTL

EAWVIHGGREDSRDLCQDPTIKELESIISKRNIQFSCKNIYRPDKFLQC

VKNPEDSSCTSEI
```

Isoform II of human CD38 has the following amino acid sequence:

```
                                          (SEQ ID NO: 3)
MANCEFSPVSGDKPCCRLSRRAQLCLGVSILVLILVVVLAVVVPRWRQQ

WSGPGTTKRFPETVLARCVKYTEIHPEMRHVDCQSVWDAFKGAFISKHP

CNITEEDYQPLMKLGTQTVPCNKK
```

In one embodiment, the immunomodulatory agent specifically binds to SEQ ID NO:3 or a functional fragment thereof and modulates CD38 mediated signal transduction or depletes CD38+ cells.

a. Ligands of CD38

One embodiment provides immunomodulatory agents that specifically bind to a ligand of CD38 and modulates CD38 mediated signal transduction. Exemplary ligands of CD38 include CD31, also called PECAM. The canonical amino acid sequence for human CD31 is as follows:

UniProt Accession P16284-1 which is incorporated by reference in its entirety.

```
                                          (SEQ ID NO: 4)
        10         20         30         40
MQPRWAQGAT MWLGVLLTLL LCSSLEGQEN SFTINSVDMK 50         60         70         80
SLPDWTVQNG KNLTLQCFAD VSTTSHVKPQ HQMLFYKDDV 90        100        110        120
LFYNISSMKS TESYFIPEVR IYDSGTYKCT VIVNNKEKTT 130        140        150        160
AEYQVLVEGV PSPRVTLDKK EAIQGGIVRV NCSVPEEKAP 170        180        190        200
IHFTIEKLEL NEKMVKLKRE KNSRDQNFVI LEFPVEEQDR 210        220        230        240
VLSFRCQARI ISGIHMQTSE STKSELVTVT ESFSTPKFHI 250        260        270        280
SPTGMIMEGA QLHIKCTIQV THLAQEFPEI IIQKDKAIVA 290        300        310        320
HNRHGNKAVY SVMAMVEHSG NYTCKVESSR ISKVSSIVVN 330        340        350        360
ITELFSKPEL ESSFTHLDQG ERLNLSCSIP GAPPANFTIQ 370        380        390        400
KEDTIVSQTQ DFTKIASKSD SGTYICTAGI DKVVKKSNTV 410        420        430        440
QIVVCEMLSQ PRISYDAQFE VIKGQTIEVR CESISGTLPI 450        460        470        480
SYQLLKTSKV LENSTKNSND PAVFKDNPTE DVEYQCVADN 490        500        510        520
CHSHAKMLSE VLRVKVIAPV DEVQISILSS KVVESGEDIV 530        540        550        560
LQCAVNEGSG PITYKFYREK EGKPFYQMTS NATQAFWTKQ 570        580        590        600
KASKEQEGEY YCTAFNRANH ASSVPRSKIL TVRVILAPWK 610        620        630        640
KGLIAVVIIG VIIALLIIAA KCYFLRKAKA KQMPVEMSRP 650        660        670        680
AVPLLNSNNE KMSDPNMEAN SHYGHNDDVR NHAMKPINDN 690        700        710        720
KEPLNSDVQY TEVQVSSAES HKDLGKKDTE TVYSEVRKAV

730
PDAVESRYSR TEGSLDGT
```

One embodiment provides an immunomodulatory agent that specifically binds SEQ ID NO:4 or a functional fragment thereof and modulates CD38 mediated signal transduction.

2. CD8

Cluster of differentiation 8 (CD8) is an integral membrane glycoprotein that plays important roles in immune response, serving multiple functions in responses against both internal and external offenses. In T cells, CD8 functions primarily as a co-receptor for MHC Class I molecule:peptide complex. CD8 interacts simultaneously with the T cell receptor and MHC Class I proteins presented by antigen presenting cells.

CD8 is a dimer of alpha chains (CD8A) and/or beta chains (CD8B). CD8 can exist as a homodimer of CD8A or a heterodimer of CD8A/CD8B. CD8A homodimer promotes survival and differentiation of activated lymphocytes into memory CD8 T cells.

Sequences for human CD8A are known in the arts. For example, the canonical amino acid sequence for human CD8A is as follows:

```
UniProt accession P01732 which is incorporated by
reference in its entirety.
                                          (SEQ ID NO: 5)
         10         20         30         40
MALPVTALLL PLALLLHAAR PSQFRVSPLD RTWNLGETVE 50         60         70         80
LKCQVLLSNP TSGCSWLFQP RGAAASPTFL LYLSQNKPKA 90        100        110        120
AEGLDTQRFS GKRLGDTFVL TLSDFRRENE GYYFCSALSN 130        140        150        160
SIMYFSHFVP VFLPARPTTT PAPRPPTPAP TIASQPLSLR 170        180        190        200
PEACRPAAGG AVHTRGLDFA CDIYIWAPLA GTCGVLLLSL 210        220        230
VITLYCNHRN RRRVCKCPRP VVKSGDKPSL SARYV
```

One embodiment provides an immunomodulatory agent that specifically binds to SEQ ID NO:5 or a functional fragment thereof and modulates CD8 mediated signal transduction. In one embodiment, the immunomodulatory agent is a bispecific and depletes CD38$^+$CD8$^+$ T-cells.

Amino acids 22-182 of SEQ ID NO:5 represent the ECD of human CD8A and has the following sequence:

```
                                          (SEQ ID NO: 6)
SQFRVSPLDRTWNLGETVELKCQVLLSNPTSGCSWLFQPRGAAASPTFL

LYLSQNKPKAAEGLDTQRFSGKRLGDTFVLTLSDFRRENEGYYFCSALS

NSIMYFSHFVPVFLPAKPTTTPAPRPPTPAPTIASQPLSLRPEACRPAA

GGAVHTRGLDFACD
```

The sequence of CD8A isoform II is as follows:

```
                                          (SEQ ID NO: 7)
MALPVTALLLPLALLLHAARPSQFRVSPLDRTWNLGETVELKCQVLLSN

PTSGCSWLFQPRGAAASPTFLLYLSQNKPKAAEGLDTQRFSGKRLGDTF

VLTLSDFRRENEGYYFCSALSNSIMYFSHFVPVFLPAKPTTTPAPRPPT

PAPTIASQPLSLRPEACRPAAGGAGNRRRVCKCPRPVVKSGDKPSLSAR

YV
```

The sequence of CD8A isoform III is as follows:

```
                                          (SEQ ID NO: 8)
MRNQAPGRPKGATFPPRRPTGSRAPPLAPELRAKQRPGERVMALPVTAL

LLPLALLLHAARPSQFRVSPLDRTWNLGETVELKCQVLLSNPTSGCSWL

FQPRGAAASPTFLLYLSQNKPKAAEGLDTQRFSGKRLGDTFVLTLSDFR

RENEGYYFCSALSNSIMYFSHFVPVFLPAKPTTTPAPRPPTPAPTIASQ

PLSLRPEACRPAAGGAVHTRGLDFACDIYIWAPLAGTCGVLLLSLVITL

YCNHRNRRRVCKCPRPVVKSGDKPSLSARYV
```

Sequences for human CD8B are known in the arts. For example, the canonical amino acid sequence for human CD8B is as follows:

```
UniProt accession P10966 which is incorporated by
reference in its entirety.
                                          (SEQ ID NO: 9)
         10         20         30         40
MRPRLWLLLA AQLTVLHGNS VLQQTPAYIK VQTNKMVMLS 50         60         70         80
CEAKISLSNM RIYWLRQRQA PSSDSHHEFL ALWDSAKGTI 90        100        110        120
HGEEVEQEKI AVFRDASRFI LNLTSVKPED SGIYFCMIVG 130        140        150        160
SPELTFGKGT QLSVVDFLPT TAQPTKKSTL KKRVCRLPRP 170        180        190        200
ETQKGPLCSP ITLGLLVAGV LVLLVSLGVA IHLCCRRRRA

210
RLRFMKQFYK
```

One embodiment provides an immunomodulatory agent that specifically binds to SEQ ID NO:9 or a functional fragment thereof and modulates CD8 mediated signal transduction. In one embodiment, the immunomodulatory agent is a bispecific and depletes CD38$^+$CD8$^+$ T-cells.

Amino acids 22-170 of SEQ ID NO:9 represent the ECD of human CD8B and has the following sequence:

```
                                          (SEQ ID NO: 10)
LQQTPAYIKVQTNKMVMLSCEAKISLSNMRIYWLRQRQAPSSDSHHEFL

ALWDSAKGTIHGEEVEQEKIAVFRDASRFILNLTSVKPEDSGIYFCMIV

GSPELTFGKGTQLSVVDFLPTTAQPTKKSTLKKRVCRLPRPETQKGPLC

SP
```

The sequence of Isoform II (also called M-3, Mbeta2) is as follows:

```
                                          (SEQ ID NO: 11)
MRPRLWLLLAAQLTVLHGNSVLQQTPAYIKVQTNKMVMLSCEAKISLSN

MRIYWLRQRQAPSSDSHHEFLALWDSAKGTIHGEEVEQEKIAVFRDASR

FILNLTSVKPEDSGIYFCMIVGSPELTFGKGTQLSVVDFLPTTAQPTKK

STLKKRVCRLPRPETQKGPLCSPITLGLLVAGVLVLLVSLGVAIHLCCR

RRRARLRFMKQLRLHPLEKCSRMDY
```

The sequence of Isoform III (also called S-1, Sbeta3) is as follows:

```
                                          (SEQ ID NO: 12)
MRPRLWLLLAAQLTVLHGNSVLQQTPAYIKVQTNKMVMLSCEAKISLSN

MRIYWLRQRQAPSSDSHHEFLALWDSAKGTIHGEEVEQEKIAVFRDASR

FILNLTSVKPEDSGIYFCMIVGSPELTFGKGTQLSVVDFLPTTAQPTKK

STLKKRVCRLPRPETQKGRRRRARLRFMKQPQGEGISGTFVPQCLHGYY

SNTTTSQKLLNPWILKT
```

The sequence of Isoform IV (also called M-2) is as follows:

(SEQ ID NO: 13)
MRPRLWLLLAAQLTVLHGNSVLQQTPAYIKVQTNKMVMLSCEAKISLSN
MRIYWLRQRQAPSSDSHHEFLALWDSAKGTIHGEEVEQEKIAVFRDASR
FILNLTSVKPEDSGIYFCMIVGSPELTFGKGTQLSVVDFLPTTAQPTKK
STLKKRVCRLPRPETQKGPLCSPITLGLLVAGVLVLLVSLGVAIHLCCR
RRRARLRFMKQKFNIVCLKISGFTTCCCFQILQISREYGFGVLLQKDIG
Q

The sequence of Isoform V (also known as Mbeta3) is as follows:

(SEQ ID NO: 14)
MRPRLWLLLAAQLTVLHGNSVLQQTPAYIKVQTNKMVMLSCEAKISLSN
MRIYWLRQRQAPSSDSHHEFLALWDSAKGTIHGEEVEQEKIAVFRDASR
FILNLTSVKPEDSGIYFCMIVGSPELTFGKGTQLSVVDFLPTTAQPTKK
STLKKRVCRLPRPETQKGPLCSPITLGLLVAGVLVLLVSLGVAIHLCCR
RRRARLRFMKQPQGEGISGTFVPQCLHGYYSNTTTSQKLLNPWILKT

The sequence of Isoform VI (also known as Sbeta1) is as follows:

(SEQ ID NO: 15)
MRPRLWLLLAAQLTVLHGNSVLQQTPAYIKVQTNKMVMLSCEAKISLSN
MRIYWLRQRQAPSSDSHHEFLALWDSAKGTIHGEEVEQEKIAVFRDASR
FILNLTSVKPEDSGIYFCMIVGSPELTFGKGTQLSVVDFLPTTAQPTKK
STLKKRVCRLPRPETQKGRRRRARLRFMKQFYK

The sequence of Isoform VII (also known as Sbeta4) is as follows:

(SEQ ID NO: 16)
MRPRLWLLLAAQLTVLHGNSVLQQTPAYIKVQTNKMVMLSCEAKISLSN
MRIYWLRQRQAPSSDSHHEFLALWDSAKGTIHGEEVEQEKIAVFRDASR
FILNLTSVKPEDSGIYFCMIVGSPELTFGKGTQLSVVDFLPTTAQPTKK
STLKKRVCRLPRPETQKDFTNKQRIGFWCPATKRHRSVMSTMWKNERRD
TFNPGEFNGC

The sequence of Isoform VIII (also know as Sbeta5) is as follows:

(SEQ ID NO: 17)
MRPRLWLLLAAQLTVLHGNSVLQQTPAYIKVQTNKMVMLSCEAKISLSN
MRIYWLRQRQAPSSDSHHEFLALWDSAKGTIHGEEVEQEKIAVFRDASR
FILNLTSVKPEDSGIYFCMIVGSPELTFGKGTQLSVVDFLPTTAQPTKK
STLKKRVCRLPRPETQKGLKGKVYQEPLSPNACMDTTAILQPHRSCLTH
GS

One embodiment provides an immunomodulatory agent that specifically binds to SEQ ID NO:9 or a functional fragment thereof and modulates CD8 mediated signal transduction. In another embodiment the immunomodulatory agent specifically binds any one of the isoforms of CD8B according to SEQ ID NO: 11-17 or a functional fragment thereof. In one embodiment the immunomodulatory agent can bind both CD38 and CD8 to deplete $CD38^+CD8^+$ T cells.

3. PD-1

PD-1 is a cell surface receptor that is predominantly expressed on activated $CD4^+$ and $CD8^+$ T cells as well as on B cells in the periphery. PD-1 acts as an immune checkpoint in T cells. It plays a role in down regulating the immune system and promoting self-tolerance by suppressing T cell inflammatory activity. Upon interaction with its ligand PD-L1, PD-1 suppresses T cell activation by recruiting SHP-1, which in turn dephosphorylates and inactivates Zap70, a major integrator of T cell receptor-mediated signaling.

Sequences for human PD-1 are known in the arts. For example, the canonical amino acid sequence for human PD-1 is as follows:

UniProt accession Q15116 which is incorporated by
reference in its entirety.
(SEQ ID NO: 18)
          10          20          30          40
MQIPQAPWPV  VWAVLQLGWR  PGWFLDSPDR  PWNPPTFSPA 50          60          70          80
LLVVTEGDNA  TFTCSFSNTS  ESFVLNWYRM  SPSNQTDKLA 90         100         110         120
AFPEDRSQPG  QDCRFRVTQL  PNGRDFHMSV  VRARRNDSGT 130         140         150         160
YLCGAISLAP  KAQIKESLRA  ELRVTERRAE  VPTAHPSPSP 170         180         190         200
RPAGQFQTLV  VGVVGGLLGS  LVLLVWVLAV  ICSRAARGTI 210         220         230         240
GARRTGQPLK  EDPSAVPVFS  VDYGELDFQW  REKTPEPPVP 250         260         270         280
CVPEQTEYAT  IVFPSGMGTS  SPARRGSADG  PRSAQPLRPE

DGHCSWPL

One embodiment provides an immunomodulatory agent that specifically binds to SEQ ID NO: 18 or a functional fragment thereof and modulates PD-1 mediated signal transduction.

In one embodiment, the immunomodulatory agent is a bispecific antibody that depletes $CD38^+PD-1^+$ T cells.

B. Immunomodulatory Agents or Binding Moieties

Immunomodulatory agents or binding moieties that bind to CD38, CD8 and/or PD-1 can be used to deplete $CD38^+ CD8^+$ T cells, $PD1^+CD38^+$ T cells, and/or $PD-1^+CD38^+ CD8^+$ T cells or to disrupt PD-1 signaling. The disclosed immunomodulatory agents or binding moieties can inhibit, reduce, or block CD38, CD8, and/or PD-1 mediated signaling. The disclosed compositions and methods can be used to modulate CD38, CD8, PD-1, and/or counter-receptor signaling on, for example, immune cells including but not limited to monocytes, Tregs, tumor-associated macrophages (TAMs), Myeloid Derived Suppressor Cells (MDSC), T cells, Th2 cells, myeloid cells including antigen-presenting cells (e.g., monocyte, macrophage, or dendritic cell), T cells, Natural Killer (NK) cells, or a combination thereof. In some embodiments, the compositions are specifically targeted to one or more cells types. In some embodiments, the disclosed compositions can be used on tumor cells.

In some embodiments, the anti-CD38, anti-CD8, and anti-PD-1 immunomodulatory agents or binding moieties inhibit, reduce, block, or otherwise disrupt signaling through a known or unknown counter-receptor through blockade of CD38, CD8, or PD-1 interaction with said known or unknown counter-receptor. For example, in some embodiments, the CD38, CD8, or PD-1 antagonists bind to, inhibit, block, create a conformational change, or otherwise interfere with CD38, CD8, or PD-1 mediated signal transduction, respectively.

1. Antibodies

In one embodiment the immunomodulatory agent or binding moiety is an antibody. Suitable antibodies can be prepared by one of skill in the art. Nucleic acid and polypeptide sequences for CD38, CD8, and PD-1 are known in the art and exemplary sequences are provided above. The sequences can be used, as discussed in more detail below, by one of skill in the art to prepare an antibody or antigen binding fragment thereof specific for CD38, CD8, and PD-1. The antibody or antigen binding fragment therefore, can be an antagonist of CD38, CD8, and PD-1 mediated signaling.

In another embodiment, the antibody is a blocking antibody. The blocking antibody blocks the signaling mediated by CD38 by preventing the binding of its natural ligand CD31. In one embodiment, the blocking antibody may not necessarily kill the CD38$^+$CD8$^+$ T cells.

CD38 antibodies are known in the art. See for example U.S. Pat. Nos. 8,362,211, 8,088,896, 8,263,746, and 8,153,765.

CD8 antibodies and antigen binding fragments are known in the art. See for example U.S. Pat. No. 5,620,956 and US Patent Applications 2009/0304659 and 2014/0271462.

To prepare an antibody or antigen binding fragment thereof that specifically binds to CD38, CD8, and/or PD-1, purified proteins, polypeptides, fragments, fusions, or epitopes to CD38, CD8, and/or PD-1, or polypeptides expressed from nucleic acid sequences thereof, can be used. The antibodies or antigen binding fragments thereof can be prepared using any suitable methods known in the art such as those discussed in more detail below.

In a preferred embodiment, the antibody is a bispecific antibody anti-CD38/CD8 antibody or a bispecific anti-CD38/anti-PD-1 antibody.

a. Human and Humanized Antibodies

In some embodiments, the antibodies are humanized antibodies. Many non-human antibodies (e.g., those derived from mice, rats, or rabbits) are naturally antigenic in humans, and thus can give rise to undesirable immune responses when administered to humans. Therefore, the use of human or humanized antibodies in the methods serves to lessen the chance that an antibody administered to a human will evoke an undesirable immune response.

Transgenic animals (e.g., mice) that are capable, upon immunization, of producing a full repertoire of human antibodies in the absence of endogenous immunoglobulin production can be employed. For example, it has been described that the homozygous deletion of the antibody heavy chain joining region (J(H)) gene in chimeric and germ-line mutant mice results in complete inhibition of endogenous antibody production. Transfer of the human germ-line immunoglobulin gene array in such germ-line mutant mice will result in the production of human antibodies upon antigen challenge.

Optionally, the antibodies are generated in other species and "humanized" for administration in humans. Humanized forms of non-human (e.g., murine) antibodies are chimeric immunoglobulins, immunoglobulin chains or fragments thereof (such as Fv, Fab, Fab', F(ab')$_2$, or other antigen-binding subsequences of antibodies) which contain minimal sequence derived from non-human immunoglobulin. Humanized antibodies include human immunoglobulins (recipient antibody) in which residues from a complementarity determining region (CDR) of the recipient antibody are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also contain residues that are found neither in the recipient antibody nor in the imported CDR or framework sequences. In general, the humanized antibody will contain substantially all of at least one, and typically two, variable domains, in which all or substantially all, of the CDR regions correspond to those of a non-human immunoglobulin and all or substantially all of the FR regions are those of a human immunoglobulin consensus sequence. The humanized antibody optimally also will contain at least a portion of an immunoglobulin constant region (Fc), typically that of a human immunoglobulin.

Methods for humanizing non-human antibodies are well known in the art. Generally, a humanized antibody has one or more amino acid residues introduced into it from a source that is non-human. These non-human amino acid residues are often referred to as "import" residues, which are typically taken from an "import" variable domain. Antibody humanization techniques generally involve the use of recombinant DNA technology to manipulate the DNA sequence encoding one or more polypeptide chains of an antibody molecule. Humanization can be essentially performed by substituting rodent CDRs or CDR sequences for the corresponding sequences of a human antibody. Accordingly, a humanized form of a nonhuman antibody (or a fragment thereof) is a chimeric antibody or fragment, wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important in order to reduce antigenicity. According to the "best-fit" method, the sequence of the variable domain of a rodent antibody is screened against the entire library of known human variable domain sequences. The human sequence which is closest to that of the rodent is then accepted as the human framework (FR) for the humanized antibody. Another method uses a particular framework derived from the consensus sequence of all human antibodies of a particular subgroup of light or heavy chains. The same framework may be used for several different humanized antibodies.

It is further important that antibodies be humanized with retention of high affinity for the antigen and other favorable biological properties. To achieve this goal, humanized antibodies can be prepared by a process of analysis of the parental sequences and various conceptual humanized products using three dimensional models of the parental and humanized sequences. Three dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved. In general, the CDR residues are directly and most substantially involved in influencing antigen binding.

The antibody can be bound to a substrate or labeled with a detectable moiety or both bound and labeled. The detectable moieties contemplated with the present compositions include fluorescent, enzymatic and radioactive markers.

b. Single-Chain Antibodies

In some embodiments, the antibodies are single-chain antibodies. Methods for the production of single-chain antibodies are well known to those of skill in the art. A single chain antibody is created by fusing together the variable domains of the heavy and light chains using a short peptide linker, thereby reconstituting an antigen binding site on a single molecule. Single-chain antibody variable fragments (scFvs) in which the C-terminus of one variable domain is tethered to the N-terminus of the other variable domain via a 15 to 25 amino acid peptide or linker have been developed without significantly disrupting antigen binding or specificity of the binding. The linker is chosen to permit the heavy chain and light chain to bind together in their proper conformational orientation. These Fvs lack the constant regions (Fc) present in the heavy and light chains of the native antibody.

c. Monovalent Antibodies

In some embodiments, the antibodies are monovalent antibodies. In vitro methods are also suitable for preparing monovalent antibodies. Digestion of antibodies to produce fragments thereof, particularly, Fab fragments, can be accomplished using routine techniques known in the art. For instance, digestion can be performed using papain. Papain digestion of antibodies typically produces two identical antigen binding fragments, called Fab fragments, each with a single antigen binding site, and a residual Fc fragment. Pepsin treatment yields a fragment, called the F(ab')$_2$ fragment, that has two antigen combining sites and is still capable of cross-linking antigen.

The Fab fragments produced in the antibody digestion also contain the constant domains of the light chain and the first constant domain of the heavy chain. Fab' fragments differ from Fab fragments by the addition of a few residues at the carboxy terminus of the heavy chain domain including one or more cysteines from the antibody hinge region. The F(ab')$_2$ fragment is a bivalent fragment comprising two Fab' fragments linked by a disulfide bridge at the hinge region. Fab'-SH is the designation herein for Fab' in which the cysteine residue(s) of the constant domains bear a free thiol group. Antibody fragments originally were produced as pairs of Fab' fragments which have hinge cysteines between them. Other chemical couplings of antibody fragments are also known.

d. Hybrid Antibodies

In some embodiments, the antibodies are hybrid antibodies. In hybrid antibodies, one heavy and light chain pair is homologous to that found in an antibody raised against one epitope, while the other heavy and light chain pair is homologous to a pair found in an antibody raised against another epitope. This results in the property of multi-functional valency, i.e., ability to bind at least two different epitopes simultaneously. Such hybrids can be formed by fusion of hybridomas producing the respective component antibodies, or by recombinant techniques. Such hybrids may, of course, also be formed using chimeric chains.

e. Conjugates or Fusions of Antibody Fragments

In some embodiments, the antibodies are conjugates or fusions of antibody fragments.

The targeting function of the antibody can be used therapeutically by coupling the antibody or a fragment thereof with a therapeutic agent. Such coupling of the antibody or fragment (e.g., at least a portion of an immunoglobulin constant region (Fc)) with the therapeutic agent can be achieved by making an immunoconjugate or by making a fusion protein, comprising the antibody or antibody fragment and the therapeutic agent.

Such coupling of the antibody or fragment with the therapeutic agent can be achieved by making an immunoconjugate or by making a fusion protein, or by linking the antibody or fragment to a nucleic acid such as an siRNA, comprising the antibody or antibody fragment and the therapeutic agent.

In some embodiments, the antibody is modified to alter its half-life. In some embodiments, it is desirable to increase the half-life of the antibody so that it is present in the circulation or at the site of treatment for longer periods of time. For example, it may be desirable to maintain titers of the antibody in the circulation or in the location to be treated for extended periods of time. Antibodies can be engineered with Fc variants that extend half-life, e.g., using Xtend™ antibody half-life prolongation technology (Xencor, Monrovia, CA). In other embodiments, the half-life of the anti-DNA antibody is decreased to reduce potential side effects. The conjugates disclosed can be used for modifying a given biological response. The drug moiety is not to be construed as limited to classical chemical therapeutic agents. For example, the drug moiety may be a protein or polypeptide possessing a desired biological activity. Such proteins may include, for example, a toxin such as abrin, ricin A, *pseudomonas* exotoxin, or diphtheria toxin.

f. Bispecific Antibody

In a preferred embodiment, the antibodies are bispecific antibodies. Bispecific antibodies are characterized by their ability to simultaneously bind two targets. Bispecific antibodies can bind two different receptors, ligands, or a combination thereof on the same cell. Alternatively, bispecific antibodies can be used to recruit effector cells to a target. In this case the bispecific can bind one arm to a cell surface receptor for a target cell while the second arm recruits an immune effector cell by binding to an antigen for the effector cell. By recruiting effector cells to the target cell, bispecific antibodies facilitate immune mediated mechanisms such as complement-dependent cytotoxicity, antibody dependent cellular toxicity, and antibody-dependent cellular phagocytosis.

Early bispecific antibodies were developed by cross-linking full-length antibodies or fusing two hybridoma cell lines to form hybrid hybridomas or quadroma cell lines. However, these formulations are difficult to consistently produce on a large scale.

Dual variable domain-immunoglobulin (DVD-Ig) is a type of bispecific antibody in which the $V_L$ and $V_H$ domains of an antibody toward a first antigen are covalently linked via short linkers to the N-terminal end of the respective light and heavy chain of a mAb against a second antigen. DVD-Ig can be engineered from any two monoclonal antibodies and retain the bioactivity of the parent monoclonal antibody. DVD-Ig bispecific antibodies can combine monoclonal antibodies of different species origin or isotype.

Methods of producing and using bispecific antibodies are known in the arts. See for example U.S. Pat. Nos. 7,226,592, 8,268,314, 9,079,965, and 9,315,567.

In one embodiment the bispecific antibody is engineered to bind CD38 and CD8 on the same cell. Binding of the antibody to CD38 and CD8 on the target cell can deplete said targeted cell. In another embodiment, the bispecific antibody is engineered to bind CD38 and PD-1 on the same cell. Binding of the antibody to CD38 and PD-1 on the target cell can deplete said targeted cell.

2. Proteins and Polypeptides a. Protein and Polypeptide Compositions

The disclosed immunomodulatory or binding agent can be a protein, polypeptide, or fusion protein. For example, the immunomodulatory agent or binding moiety can be an isolated or recombinant protein or polypeptide, or functional fragment, variant, or fusion protein thereof of CD38 and CD8 and/or PD-1.

The CD38, CD8, or PD-1 protein or polypeptide, or functional fragment, variant, or fusion protein thereof can be an antagonist. For example, in some embodiments an antagonist of CD38, CD8, or PD-1 is a CD38, CD8, or PD-1 polypeptide or a fragment or fusion protein thereof that binds to a ligand of CD38, CD8, or PD-1. The polypeptide can be a soluble fragment, for example the extracellular domain of CD38, CD8, or PD-1, or a functional fragment thereof, or a fusion protein thereof. In some embodiments, a soluble ligand of CD38, CD8, or PD-1 may serve as an antagonist, decreasing CD38, CD8, or PD-1 mediated signal transduction.

The activity of a protein or polypeptide of CD38, CD8, or PD-1, or any fragment, variant or fusion protein thereof can be determined using functional assays that are known in the art, and include the assays discussed below. Typically, the assays include determining if the protein, polypeptide or fragment, variant or fusion protein thereof increases (i.e., agonist) or decreases (i.e., antagonist) signaling through the CD38, CD8, or PD-1 receptor. In some embodiments, the assay includes determining if the protein, polypeptide or fragment, variant, or fusion protein thereof increases (i.e., agonist) or decreases (i.e., antagonist) the immune response associated with CD38, CD8, or PD-1. Typically, the assays include determining if the protein, polypeptide or fragment, variant, or fusion protein thereof increases (i.e., agonist) or decreases (i.e., antagonist) signaling through CD38, CD8, or PD-1. In some embodiments, the assay includes determining if the protein, polypeptide or fragment, variant, or fusion protein thereof decreases (i.e., agonist) or increases (i.e., antagonist) an immune response regulated by CD38, CD8, or PD-1. In some embodiments, the assay includes determining if the protein, polypeptide or fragment, variant, or fusion protein thereof increases (i.e., antagonist) the apoptosis and differentiation of acute myeloid leukemia cells and acute lymphoblastic leukemia cells resulting in reduced self-renewal capacity of AML and ALL stem cells.

Nucleic acid and polypeptide sequences for CD38, CD8, and PD-1 are known in the art and exemplary protein and peptide sequences are provided above. The sequences can be used, as discussed in more detail below, by one of skill in the art to prepare any protein or polypeptide of CD38, CD8, or PD-1, or any fragment, variant, or fusion protein thereof. Generally, the proteins, polypeptides, fragments, variants, and fusions thereof of CD38, CD8, or PD-1 are expressed from nucleic acids that include sequences that encode a signal sequence. The signal sequence is generally cleaved from the immature polypeptide to produce the mature polypeptide lacking the signal sequence. The signal sequence can be replaced by the signal sequence of another polypeptide using standard molecule biology techniques to affect the expression levels, secretion, solubility, or other property of the polypeptide CD38, CD8, or PD-1 proteins with and without a signal sequence are disclosed. It is understood that in some cases, the mature protein as it is known or described in the art, i.e., the protein sequence without the signal sequence, is a putative mature protein. During normal cell expression, a signal sequence can be removed by a cellular peptidase to yield a mature protein. The sequence of the mature protein can be determined or confirmed using methods that are known in the art.

i. Fragments

As used herein, a fragment of CD38, CD8, or PD-1 refers to any subset of the polypeptide that is at least one amino acid shorter than full length protein. Useful fragments include those that retain the ability to bind to their natural ligand or ligands. A polypeptide that is a fragment of any full-length CD38, CD8, or PD-1 typically has at least 20 percent, 30 percent, 40 percent, 50 percent, 60 percent, 70 percent, 80 percent, 90 percent, 95 percent, 98 percent, 99 percent, 100 percent, or even more than 100 percent of the ability to bind its natural ligand respectively as compared to the full-length protein.

Fragments of CD38, CD8, or PD-1 include cell free fragments. Cell free polypeptides can be fragments of full-length, transmembrane, polypeptides that may be shed, secreted or otherwise extracted from the producing cells. Cell free fragments of polypeptides can include some or all of the extracellular domain of the polypeptide, and lack some or all of the intracellular and/or transmembrane domains of the full-length protein. In one embodiment, polypeptide fragments include the entire extracellular domain of the full-length protein. In other embodiments, the cell free fragments of the polypeptides include fragments of the extracellular domain that retain biological activity of full-length protein. The extracellular domain can include 1, 2, 3, 4, or 5 contiguous amino acids from the transmembrane domain, and/or 1, 2, 3, 4, or 5 contiguous amino acids from the signal sequence. Alternatively, the extracellular domain can have 1, 2, 3, 4, 5 or more amino acids removed from the C-terminus, N-terminus, or both. In some embodiments the extracellular domain is the only functional domain of the fragment (e.g., the ligand binding domain).

ii. Variants

Variants of CD38 and fragments thereof are also provided. In some embodiments, the variant is at least 50, 60, 70, 80, 85, 90, 95, 96, 97, 98, or 99 percent identical to any one of SEQ ID NO: 1-3. Variants of CD8 and fragments thereof are also provided. In some embodiments, the variant is at least 50, 60, 70, 80, 85, 90, 95, 96, 97, 98, or 99 percent identical to any one of SEQ ID NO:5-17. Variants of PD-1 and fragments thereof are also provided. In some embodiments, the variant is at least 50, 60, 70, 80, 85, 90, 95, 96, 97, 98, or 99 percent identical to any one of SEQ ID NO: 18. Useful variants include those that increase biological activity, as indicated by any of the assays described herein, or that increase half-life or stability of the protein. The protein and polypeptides of CD38, CD8, or PD-1, and fragments, variants, and fusion proteins thereof can be engineered to increase biological activity. For example, in some embodiments, a CD38, CD8, or PD-1 polypeptide, protein, or fragment, variant or fusion thereof has been modified with at least one amino acid substitution, deletion, or insertion that increases a function thereof.

Finally, variant polypeptides can be engineered to have an increased half-life relative to wildtype. These variants typically are modified to resist enzymatic degradation. Exemplary modifications include modified amino acid residues and modified peptide bonds that resist enzymatic degradation. Various modifications to achieve this are known in the art. The variants can be modified to adjust for effects of affinity for the receptor on the half-life of proteins, polypeptides, fragments, or fusions thereof at serum and endosomal pH.

iii. Fusion Proteins

Fusion polypeptides have a first fusion partner including all or a part of a human or mouse CD38, CD8, or PD-1 polypeptide fused to a second polypeptide directly or via a linker peptide sequence that is fused to the second polypeptide. In one embodiment, the ECD of human or mouse CD38, CD8, or PD-1 or a fragment thereof is fused to a second polypeptide. The fusion proteins optionally contain a domain that functions to dimerize or multimerize two or more fusion proteins. The peptide/polypeptide linker domain can either be a separate domain, or alternatively can be contained within one of the other domains (first polypeptide or second polypeptide) of the fusion protein. Similarly, the domain that functions to dimerize or multimerize the fusion proteins can either be a separate domain, or alternatively can be contained within one of the other domains (first polypeptide, second polypeptide or peptide/polypeptide linker domain) of the fusion protein. In one embodiment, the dimerization/multimerization domain and the peptide/polypeptide linker domain are the same.

Fusion proteins disclosed herein are of formula I:

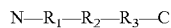

wherein "N" represents the N-terminus of the fusion protein, "C" represents the C-terminus of the fusion protein. In some embodiments, "$R_1$" is a polypeptide or protein of CD38, CD8, or PD-1 or fragment or variant thereof, "$R_2$" is an optional peptide/polypeptide linker domain, and "$R_3$" is a second polypeptide. Alternatively, $R_3$ may be a polypeptide or protein of CD38, CD8, or PD-1, or fragment or variant thereof and $R_1$ may be a second polypeptide. In some embodiments, the CD38, CD8, or PD-1 polypeptide is the extracellular domain.

Dimerization or multimerization can occur between or among two or more fusion proteins through dimerization or multimerization domains. Alternatively, dimerization or multimerization of fusion proteins can occur by chemical crosslinking. The dimers or multimers that are formed can be homodimeric/homomultimeric or heterodimeric/heteromultimeric.

In some embodiments, the fusion protein includes the extracellular domain of CD38, CD8, or PD-1, or a fragment or variant thereof, fused to an Ig Fc region. Recombinant Ig fusion proteins can be prepared by fusing the coding region of the extracellular domain or a fragment or variant thereof to the Fc region of human IgG1, IgG2, IgG3 or IgG4 or mouse IgG2a, or other suitable Ig domain, as described previously (Chapoval, et al., Methods Mol. Med., 45:247-255 (2000)).

iv. Polypeptide Modifications

The polypeptides and fusion proteins may be modified by chemical moieties that may be present in polypeptides in a normal cellular environment, for example, phosphorylation, methylation, amidation, sulfation, acylation, glycosylation, sumoylation and ubiquitylation. Fusion proteins may also be modified with a label capable of providing a detectable signal, either directly or indirectly, including, but not limited to, radioisotopes and fluorescent compounds.

The polypeptides and fusion proteins may also be modified by chemical moieties that are not normally added to polypeptides in a cellular environment. For example, the disclosed fusion proteins may also be modified by covalent attachment of polymer chains, including, but not limited to, polyethylene glycol polymer (PEG) chains (i.e., pegylation). Conjugation of macromolecules to PEG has emerged recently as an effective strategy to alter the pharmacokinetic (PK) profiles of a variety of drugs, and thereby to improve their therapeutic potential. PEG conjugation increases retention of drugs in the circulation by protecting against enzymatic digestion, slowing filtration by the kidneys and reducing the generation of neutralizing antibodies. In addition, PEG conjugates can be used to allow multimerization of the fusion proteins.

Modifications may be introduced into the molecule by reacting targeted amino acid residues of the polypeptide with an organic derivatizing agent that is capable of reacting with selected side chains or terminal residues. Another modification is cyclization of the protein.

Examples of chemical derivatives of the polypeptides include lysinyl and amino terminal residues derivatized with succinic or other carboxylic acid anhydrides. Derivatization with a cyclic carboxylic anhydride has the effect of reversing the charge of the lysinyl residues. Other suitable reagents for derivatizing amino-containing residues include imidoesters such as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate. Carboxyl side groups, aspartyl or glutamyl, may be selectively modified by reaction with carbodiimides (R—N=C=N—R') such as 1-cyclohexyl-3-(2-morpholinyl-(4-ethyl)carbodiimide or 1-ethyl-3-(4-azonia-4,4-dimethylpentyl) carbodiimide. Furthermore, aspartyl and glutamyl residues can be converted to asparaginyl and glutaminyl residues by reaction with ammonia. Fusion proteins may also include one or more D-amino acids that are substituted for one or more L-amino acids.

v. Modified Binding Properties

Binding properties of the proteins, polypeptides, fragments, variants and fusions thereof are relevant to the dose and dose regimen to be administered. In one embodiment the disclosed proteins, polypeptides, fragments, variants and fusions thereof have binding properties to CD38, CD8, PD-1 or a CD38, CD8, or PD-1 ligand that demonstrate a higher term, or higher percentage, of occupancy of a binding site (e.g., on the ligand) relative to other receptor molecules that bind thereto. In other embodiments, the disclosed proteins, polypeptides, fragments, variants and fusions thereof have reduced binding affinity to a CD38, CD8, or PD-1 relative to wildtype protein.

In some embodiments the proteins, polypeptides, fragments, variants and fusions thereof have a relatively high affinity for CD38, CD8, or PD-1 and may therefore have a relatively slow off rate. In other embodiments, the proteins polypeptides, fragments, variants and fusions thereof are administered intermittently over a period of days, weeks or months to dampen immune responses which are allowed to recover prior to the next administration, which may serve to alter the immune response without completely turning the immune response on or off and may avoid long term side effects.

3. Isolated Nucleic Acid Molecules

Isolated nucleic acid sequences encoding the CD38, CD8, or PD-1 proteins, polypeptides, fragments, variants and fusions thereof are disclosed herein. As used herein, "isolated nucleic acid" refers to a nucleic acid that is separated from other nucleic acid molecules that are present in a mammalian genome, including nucleic acids that normally flank one or both sides of the nucleic acid in a mammalian genome. The term "isolated" as used herein with respect to nucleic acids also includes the combination with any non-naturally-occurring nucleic acid sequence, since such non-naturally-occurring sequences are not found in nature and do not have immediately contiguous sequences in a naturally-occurring genome.

An isolated nucleic acid can be, for example, a DNA molecule, provided one of the nucleic acid sequences normally found immediately flanking that DNA molecule in a naturally-occurring genome is removed or absent. Thus, an isolated nucleic acid includes, without limitation, a DNA molecule that exists as a separate molecule independent of other sequences (e.g., a chemically synthesized nucleic acid, or a cDNA or genomic DNA fragment produced by PCR or restriction endonuclease treatment), as well as recombinant DNA that is incorporated into a vector, an autonomously replicating plasmid, a virus (e.g., a retrovirus, lentivirus, adenovirus, or herpes virus), or into the genomic DNA of a prokaryote or eukaryote. In addition, an isolated nucleic acid can include an engineered nucleic acid such as a recombinant DNA molecule that is part of a hybrid or fusion nucleic acid. A nucleic acid existing among hundreds to millions of other nucleic acids within, for example, a cDNA library or a genomic library, or a gel slice containing a genomic DNA restriction digest, is not to be considered an isolated nucleic acid.

Nucleic acids encoding the proteins, polypeptides, fragments, variants and fusions thereof may be optimized for expression in the expression host of choice. Codons may be substituted with alternative codons encoding the same amino acid to account for differences in codon usage between the mammal from which the nucleic acid sequence is derived and the expression host. In this manner, the nucleic acids may be synthesized using expression host-preferred codons.

Nucleic acids can be in sense or antisense orientation, or can be complementary to a reference sequence encoding a polypeptide or protein of CD38, CD8, or PD-1. Nucleic acids can be DNA, RNA, or nucleic acid analogs. Nucleic acid analogs can be modified at the base moiety, sugar moiety, or phosphate backbone. Such modification can improve, for example, stability, hybridization, or solubility of the nucleic acid. Modifications at the base moiety can include deoxyuridine for deoxythymidine, and 5-methyl-2'-deoxycytidine or 5-bromo-2'-deoxycytidine for deoxycytidine. Modifications of the sugar moiety can include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six membered, morpholino ring, or peptide nucleic acids, in which the deoxyphosphate backbone is replaced by a pseudopeptide backbone and the four bases are retained. See, for example, Summerton and Weller (1997) Antisense Nucleic Acid Drug Dev. 7:187-195; and Hyrup et al. (1996) Bioorgan. Med. Chem. 4:5-23. In addition, the deoxyphosphate backbone can be replaced with, for example, a phosphorothioate or phosphorodithioate backbone, a phosphoroamidite, or an alkyl phosphotriester backbone.

Nucleic acids encoding polypeptides can be administered to subjects in need thereof. Nucleic delivery involves introduction of "foreign" nucleic acids into a cell and ultimately, into a live animal. Compositions and methods for delivering nucleic acids to a subject are known in the art (see Understanding Gene Therapy, Lemoine, N. R., ed., BIOS Scientific Publishers, Oxford, 2008).

4. Vectors and Host Cells

Vectors encoding the proteins, polypeptides, fragments, variants and fusions thereof are also provided. Nucleic acids, such as those described above, can be inserted into vectors for expression in cells. As used herein, a "vector" is a replicon, such as a plasmid, phage, virus or cosmid, into which another DNA segment may be inserted so as to bring about the replication of the inserted segment. Vectors can be expression vectors. An "expression vector" is a vector that includes one or more expression control sequences, and an "expression control sequence" is a DNA sequence that controls and regulates the transcription and/or translation of another DNA sequence.

Nucleic acids in vectors can be operably linked to one or more expression control sequences. As used herein, "operably linked" means incorporated into a genetic construct so that expression control sequences effectively control expression of a coding sequence of interest. Examples of expression control sequences include promoters, enhancers, and transcription terminating regions. A promoter is an expression control sequence composed of a region of a DNA molecule, typically within 100 nucleotides upstream of the point at which transcription starts (generally near the initiation site for RNA polymerase II). To bring a coding sequence under the control of a promoter, it is necessary to position the translation initiation site of the translational reading frame of the polypeptide between one and about fifty nucleotides downstream of the promoter. Enhancers provide expression specificity in terms of time, location, and level. Unlike promoters, enhancers can function when located at various distances from the transcription site. An enhancer also can be located downstream from the transcription initiation site. A coding sequence is "operably linked" and "under the control" of expression control sequences in a cell when RNA polymerase is able to transcribe the coding sequence into mRNA, which then can be translated into the protein encoded by the coding sequence.

Suitable expression vectors include, without limitation, plasmids and viral vectors derived from, for example, bacteriophage, baculoviruses, tobacco mosaic virus, herpes viruses, cytomegalo virus, retroviruses, vaccinia viruses, adenoviruses, and adeno-associated viruses. Numerous vectors and expression systems are commercially available from such corporations as Novagen (Madison, WI), Clontech (Palo Alto, CA), Stratagene (La Jolla, CA), and Invitrogen Life Technologies (Carlsbad, CA).

An expression vector can include a tag sequence. Tag sequences, are typically expressed as a fusion with the encoded polypeptide. Such tags can be inserted anywhere within the polypeptide including at either the carboxyl or amino terminus. Examples of useful tags include, but are not limited to, green fluorescent protein (GFP), glutathione S-transferase (GST), polyhistidine, c-myc, hemagglutinin, Flag™ tag (Kodak, New Haven, CT), maltose E binding protein and protein A. In one embodiment, a nucleic acid molecule encoding one of the disclosed polypeptides is present in a vector containing nucleic acids that encode one or more domains of an Ig heavy chain constant region, for example, having an amino acid sequence corresponding to the hinge, CH2 and CH3 regions of a human immunoglobulin Cγl chain.

Vectors containing nucleic acids to be expressed can be transferred into host cells. The term "host cell" is intended to include prokaryotic and eukaryotic cells into which a recombinant expression vector can be introduced. As used herein, "transformed" and "transfected" encompass the introduction of a nucleic acid molecule (e.g., a vector) into a cell by one of a number of techniques. Although not limited to a particular technique, a number of these techniques are well established within the art. Prokaryotic cells can be transformed with nucleic acids by, for example, electroporation or calcium chloride mediated transformation. Nucleic acids can be transfected into mammalian cells by techniques including, for example, calcium phosphate co-precipitation, DEAE-dextran-mediated transfection, lipofection, electroporation, or microinjection. Host cells (e.g., a prokaryotic cell or a eukaryotic cell such as a CHO cell) can be used to, for example, produce the proteins, polypeptides, fragments, variants and fusions thereof described herein.

The vectors described can be used to express the proteins, polypeptides, fragments, variants and fusions thereof in cells. An exemplary vector includes, but is not limited to, an adenoviral vector. One approach includes nucleic acid transfer into primary cells in culture followed by autologous transplantation of the ex vivo transformed cells into the host, either systemically or into a particular organ or tissue. Ex vivo methods can include, for example, the steps of harvesting cells from a subject, culturing the cells, transducing them with an expression vector, and maintaining the cells under conditions suitable for expression of the encoded polypeptides. These methods are known in the art of molecular biology. The transduction step can be accomplished by any standard means used for ex vivo gene therapy, including, for example, calcium phosphate, lipofection, electroporation, viral infection, and biolistic gene transfer. Alternatively, liposomes or polymeric microparticles can be used. Cells that have been successfully transduced then can be selected, for example, for expression of the coding sequence or of a drug resistance gene. The cells then can be lethally irradiated (if desired) and injected or implanted into the subject. In one embodiment, expression vectors containing nucleic acids encoding fusion proteins are transfected into cells that are administered to a subject in need thereof.

In vivo nucleic acid therapy can be accomplished by direct transfer of a functionally active DNA into mammalian somatic tissue or organ in vivo. For example, nucleic acids encoding polypeptides disclosed herein can be administered directly to lymphoid tissues.

Alternatively, lymphoid tissue specific targeting can be achieved using lymphoid tissue-specific transcriptional regulatory elements (TREs) such as a B lymphocyte-, T lymphocyte-, or dendritic cell-specific TRE. Lymphoid tissue specific TREs are known in the art.

Nucleic acids may also be administered in vivo by viral means. Nucleic acid molecules encoding fusion proteins may be packaged into retrovirus vectors using packaging cell lines that produce replication-defective retroviruses, as is well-known in the art. Other virus vectors may also be used, including recombinant adenoviruses and vaccinia virus, which can be rendered non-replicating. In addition to naked DNA or RNA, or viral vectors, engineered bacteria may be used as vectors.

Nucleic acids may also be delivered by other carriers, including liposomes, polymeric micro- and nanoparticles and polycations such as asialoglycoprotein/polylysine.

In addition to virus- and carrier-mediated gene transfer in vivo, physical means well-known in the art can be used for direct transfer of DNA, including administration of plasmid DNA and particle-bombardment mediated gene transfer.

5. Small Molecules

In one embodiment, the immunomodulatory agent is a small molecule. Small molecules antagonists of CD38, CD8, and PD-1 are known in the art or can be identified using routine screening methods. CD38 small molecule inhibitors include but are not limited to inhibitors disclosed in WO 2013/002879, U.S. Pat. No. 7,504,489, as well as the natural anthranoid rhein, K-rhein, quercetin, apigenin, leteolinidin, heterocycles derivatives of 4-amino-quinoline, and the polyphenol tannic acid (TA) (Chini et al., *Trends Pharmacol Sci*, 39(4):424-436).

In some embodiments, screening assays can include random screening of large libraries of test compounds. Alternatively, the assays may be used to focus on particular classes of compounds suspected of modulating the level of CD38, CD8, or PD-1. Assays can include determinations of CD38, CD8, and PD-1 mediated signaling activity. Other assays can include determinations of nucleic acid transcription or translation, mRNA levels, mRNA stability, mRNA degradation, transcription rates, and translation rates.

C. Pharmaceutical Compositions

Pharmaceutical compositions including the disclosed immunomodulatory agents are provided. Pharmaceutical compositions containing the antibodies and antigen binding fragments thereof can be for administration by parenteral (intramuscular, intraperitoneal, intravenous (IV) or subcutaneous injection).

In some in vivo approaches, the compositions disclosed herein are administered to a subject in a therapeutically effective amount. As used herein the term "effective amount" or "therapeutically effective amount" means a dosage sufficient to treat, inhibit, or alleviate one or more symptoms of the disorder being treated or to otherwise provide a desired pharmacologic and/or physiologic effect. The precise dosage will vary according to a variety of factors such as subject-dependent variables (e.g., age, immune system health, etc.), the disease, and the treatment being effected.

For the disclosed antibodies and antigen binding fragments thereof, as further studies are conducted, information will emerge regarding appropriate dosage levels for treatment of various conditions in various patients, and the ordinary skilled worker, considering the therapeutic context, age, and general health of the recipient, will be able to ascertain proper dosing. The selected dosage depends upon the desired therapeutic effect, on the route of administration, and on the duration of the treatment desired. For the disclosed antibodies and antigen binding fragments thereof, generally dosage levels of 0.001 to 20 mg/kg of body weight daily are administered to mammals. Generally, for intravenous injection or infusion, dosage may be lower.

In certain embodiments, the antibodies and antigen binding fragments thereof are administered locally, for example by injection directly into a site to be treated. Typically, the injection causes an increased localized concentration of the immunomodulatory agent composition which is greater than that which can be achieved by systemic administration. The immunomodulatory agent compositions can be combined with a matrix as described above to assist in creating an increased localized concentration of the polypeptide compositions by reducing the passive diffusion of the polypeptides out of the site to be treated.

In some embodiments, the compositions containing the disclosed antibodies and antigen binding fragments are administered in an aqueous solution, by parenteral injection. The formulation may also be in the form of a suspension or emulsion. In general, pharmaceutical compositions are provided including effective amounts of an antibody or antigen binding fragment thereof, and optionally include pharmaceutically acceptable diluents, preservatives, solubilizers, emulsifiers, adjuvants and/or carriers. Such compositions optionally include one or more for the following: diluents, sterile water, buffered saline of various buffer content (e.g., Tris-HCl, acetate, phosphate), pH and ionic strength; and additives such as detergents and solubilizing agents (e.g., TWEEN 20 (polysorbate-20), TWEEN 80 (polysorbate-80)), anti-oxidants (e.g., ascorbic acid, sodium metabisulfite), and preservatives (e.g., Thimersol, benzyl alcohol) and bulking substances (e.g., lactose, mannitol). Examples of non-aqueous solvents or vehicles are propylene glycol, polyethylene glycol, vegetable oils, such as olive oil and corn oil, gelatin, and injectable organic esters such as ethyl oleate. The formulations may be lyophilized and redissolved/resuspended immediately before use. The formulation may be sterilized by, for example, filtration through a bacteria retaining filter, by incorporating sterilizing agents into the compositions, by irradiating the compositions, or by heating the compositions.

D. Ex Vivo Methods for CD38 Cell Depletion

CD38 expressing CD8$^+$ T cells can also be depleted using a variety of ex vivo methods. In one embodiment, CD38 expressing CD8$^+$ T cells are depleted using flow cytometry. In such an embodiment, immune cells are collected from the subject, for example in a biological specimen such as blood or from a tissue biopsy. The immune cells are labeled with fluorescent antibodies against CD38, CD8, PD-1, or combinations thereof. CD38$^+$CD8$^+$ T cells, CD38$^+$PD-1$^+$ T cells, CD38$^+$PD-1$^+$CD8$^+$ T cells or combinations thereof can be sorted out of the population of cells by a flow cytometer. The remaining population of cells can be administered back to the subject without the population of CD38$^+$PD-1$^+$CD8$^+$ T cells.

In another embodiment, the CD38 expressing CD8$^+$ T cells are depleted using magnetic sorting. In such an embodiment, immune cells are collected from the subject, for example in a biological specimen such as blood or from a tissue biopsy. The immune cells are labeled with magnetic nanoparticles-conjugated to antibodies against CD38, CD8, PD-1, or combinations thereof. CD38$^+$CD8$^+$ T cells, CD38$^+$PD-1$^+$ T cells, CD38$^+$PD-1$^+$CD8$^+$ T cells or combinations thereof can be sorted out of the population of cells using a magnetic cell sorting device or column. The remaining population of cells can be administered back to the subject without the population of CD38$^+$PD-1$^+$CD8$^+$ T cells.

III. Methods of Manufacture

A. Methods of Making Antibodies

The disclosed antibodies can be generated in cell culture, in phage, or in various animals, including but not limited to cows, rabbits, goats, mice, rats, hamsters, guinea pigs, sheep, dogs, cats, monkeys, chimpanzees, apes. In one embodiment, the various animals can be transgenic animals genetically engineered to produce human or humanized antibodies. Therefore, in one embodiment, the antibody is a mammalian antibody. Phage techniques can be used to isolate an initial antibody or to generate variants with altered specificity or avidity characteristics. Such techniques are routine and well known in the art. In one embodiment, the antibody is produced by recombinant means known in the art. For example, a recombinant antibody can be produced by transfecting a host cell with a vector comprising a DNA sequence encoding the antibody. One or more vectors can be used to transfect the DNA sequence expressing at least one $V_L$ and one $V_H$ region in the host cell. Exemplary descriptions of recombinant means of antibody generation and production include Chiu, M. L. and Gilliland, G. L., "Engineering antibody therapeutics," *Curr Opi Structural Biol*, 38:163-173 (2016); Saeed, A., et al., "Antibody Engineering for Pursuing a Healthier Future," *Frontiers in Microbiology*, 8:496 (2017); Hurrell, J. G. R, *Monoclonal Hybridoma Antibodies* (CRC Press) 2018; *Current Protocols In Immunology* (John Wiley & Sons, most recent edition).

The disclosed antibodies can be modified by recombinant means to increase greater efficacy of the antibody in mediating the desired function. Thus, it is within the scope of the invention that antibodies can be modified by substitutions using recombinant means. Typically, the substitutions will be conservative substitutions. For example, at least one amino acid in the constant region of the antibody can be replaced with a different residue. See, e.g., U.S. Pat. Nos. 5,624,821, 6,194,551, Application No. WO 9958572; and Angal, et al., *Mol. Immunol.* 30:105-08 (1993). The modification in amino acids includes deletions, additions, and substitutions of amino acids. In some cases, such changes are made to reduce undesired activities, e.g., complement-dependent cytotoxicity. Frequently, the antibodies are labeled by joining, either covalently or non-covalently, a substance which provides for a detectable signal. A wide variety of labels and conjugation techniques are known and are reported extensively in both the scientific and patent literature. These antibodies can be screened for binding to proteins, polypeptides. See, e.g., *Antibody Engineering: A Practical Approach* (Oxford University Press, 1996).

For example, suitable antibodies with the desired biologic activities can be identified using in vitro assays including but not limited to: proliferation, migration, adhesion, soft agar growth, angiogenesis, cell-cell communication, apoptosis, transport, signal transduction, and in vivo assays such as the inhibition of tumor growth. The antibodies provided herein can also be useful in diagnostic applications. As capture or non-neutralizing antibodies, they can be screened for the ability to bind to the specific antigen without inhibiting the receptor-binding or biological activity of the antigen. As neutralizing antibodies, the antibodies can be useful in competitive binding assays.

Antibodies that can be used in the disclosed compositions and methods include whole immunoglobulin (i.e., an intact antibody) of any class, fragments thereof, and synthetic proteins containing at least the antigen binding variable domain of an antibody. The variable domains differ in sequence among antibodies and are used in the binding and specificity of each particular antibody for its particular antigen. However, the variability is not usually evenly distributed through the variable domains of antibodies. It is typically concentrated in three segments called complementarity determining regions (CDRs) or hypervariable regions both in the light chain and the heavy chain variable domains. The more highly conserved portions of the variable domains are called the framework (FR). The variable domains of native heavy and light chains each comprise four FR regions, largely adopting a beta-sheet configuration, connected by three CDRs, which form loops connecting, and in some cases forming part of, the beta-sheet structure. The CDRs in each chain are held together in close proximity by the FR regions and, with the CDRs from the other chain, contribute to the formation of the antigen binding site of antibodies.

Also disclosed are fragments of antibodies which have bioactivity. The fragments, whether attached to other sequences or not, include insertions, deletions, substitutions, or other selected modifications of particular regions or specific amino acids residues, provided the activity of the fragment is not significantly altered or impaired compared to the nonmodified antibody or antibody fragment.

Techniques can also be adapted for the production of single-chain antibodies based on the disclosed antibodies and antigen binding fragments thereof. Methods for the production of single-chain antibodies are well known to those of skill in the art. A single chain antibody can be created by fusing together the variable domains of the heavy and light chains using a short peptide linker, thereby reconstituting an antigen binding site on a single molecule. Single-chain antibody variable fragments (scFvs) in which the C-terminus of one variable domain is tethered to the N-terminus of the other variable domain via a 15 to 25 amino acid peptide or linker have been developed without significantly disrupting antigen binding or specificity of the binding. The linker is chosen to permit the heavy chain and light chain to bind together in their proper conformational orientation.

One embodiment provides divalent single-chain variable fragments (di-scFvs) that can be engineered by linking two scFvs. This can be done by producing a single peptide chain with two VH and two VL regions, yielding tandem scFvs. ScFvs can also be designed with linker peptides that are too short for the two variable regions to fold together (about five amino acids), forcing scFvs to dimerize. This type is known as diabodies. Diabodies have been shown to have dissociation constants up to 40-fold lower than corresponding scFvs, meaning that they have a much higher affinity to their target. Still shorter linkers (one or two amino acids) lead to the formation of trimers (triabodies or tribodies). Tetrabodies have also been produced. They exhibit an even higher affinity to their targets than diabodies.

Another embodiment provides a monoclonal antibody obtained from a substantially homogeneous population of antibodies, i.e., the individual antibodies within the population are identical except for possible naturally occurring mutations that may be present in a small subset of the antibody molecules. Monoclonal antibodies include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, as long as they exhibit the desired antagonistic activity.

Monoclonal antibodies can be made using any procedure which produces monoclonal antibodies. In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro.

The disclosed antibodies may also be made by recombinant DNA methods. DNA encoding the disclosed antibodies can be readily isolated and sequenced using conventional procedures (e.g., by using oligonucleotide probes that are capable of binding specifically to genes encoding the heavy and light chains of murine antibodies). Libraries of antibodies or active antibody fragments can also be generated and screened using phage display techniques.

Methods of making antibodies using protein chemistry are also known in the art. One method of producing proteins comprising the antibodies is to link two or more peptides or polypeptides together by protein chemistry techniques. For example, peptides or polypeptides can be chemically synthesized using currently available laboratory equipment using either Fmoc (9-fluorenylmethyloxycarbonyl) or Boc (tert-butyloxycarbonoyl) chemistry. (Applied Biosystems, Inc., Foster City, CA). One skilled in the art can readily appreciate that a peptide or polypeptide corresponding to the antibody, for example, can be synthesized by standard chemical reactions. For example, a peptide or polypeptide can be synthesized and not cleaved from its synthesis resin whereas the other fragment of an antibody can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form an antibody, or fragment thereof. Alternatively, the peptide or polypeptide is independently synthesized in vivo as described above. Once isolated, these independent peptides or polypeptides may be linked to form an antibody or antigen binding fragment thereof via similar peptide condensation reactions.

For example, enzymatic ligation of cloned or synthetic peptide segments allow relatively short peptide fragments to be joined to produce larger peptide fragments, polypeptides or whole protein domains. Alternatively, native chemical ligation of synthetic peptides can be utilized to synthetically construct large peptides or polypeptides from shorter peptide fragments. This method consists of a two-step chemical reaction. The first step is the chemoselective reaction of an unprotected synthetic peptide-alpha-thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site.

Methods of making bispecific antibodies are known in the arts. (See for example Yang et al., *Int J Mol Sci*, 18:48 (2016), U.S. Pat. Nos. 7,235,641 and 9,315,567) In one embodiment the bispecific antibody is produced from a quadroma cell line. Quadromas are produced by the fusion of two parental hybridoma cell lines, each expressing a different antibody. For example, one parental hybridoma can express CD38 and the other parental hybridoma can express CD8. The resulting quadroma can then produce a bispecific CD38xCD8 antibody.

B. Methods for Producing Isolated Nucleic Acid Molecules

One embodiment provides nucleic acids encoding the disclosed antibodies or antigen binding fragments thereof. The nucleic acids can encode the entire antibody or antigen binding fragments thereof or a light chain, heavy chain, combinations thereof or CDRs thereof.

Isolated nucleic acid molecules can be produced by standard techniques, including, without limitation, common molecular cloning and chemical nucleic acid synthesis techniques. For example, polymerase chain reaction (PCR) techniques can be used to obtain an isolated nucleic acid encoding a variant polypeptide. PCR is a technique in which target nucleic acids are enzymatically amplified. Typically, sequence information from the ends of the region of interest or beyond can be employed to design oligonucleotide primers that are identical in sequence to opposite strands of the template to be amplified. PCR can be used to amplify specific sequences from DNA as well as RNA, including sequences from total genomic DNA or total cellular RNA.

Primers typically are 14 to 40 nucleotides in length, but can range from 10 nucleotides to hundreds of nucleotides in length. General PCR techniques are described, for example in *PCR Primer: A Laboratory Manual*, ed. by Dieffenbach and Dveksler, Cold Spring Harbor Laboratory Press, 1995. When using RNA as a source of template, reverse transcriptase can be used to synthesize a complementary DNA (cDNA) strand. Ligase chain reaction, strand displacement amplification, self-sustained sequence replication or nucleic acid sequence-based amplification also can be used to obtain isolated nucleic acids. See, for example, Lewis (1992) *Genetic Engineering News* 12:1; Guatelli et al. (1990) *Proc. Natl. Acad. Sci. USA* 87:1874-1878; and Weiss (1991) *Science* 254:1292-1293.

Isolated nucleic acids can be chemically synthesized, either as a single nucleic acid molecule or as a series of oligonucleotides (e.g., using phosphoramidite technology for automated DNA synthesis in the 3' to 5' direction). For example, one or more pairs of long oligonucleotides (e.g., >100 nucleotides) can be synthesized that contain the desired sequence, with each pair containing a short segment of complementarity (e.g., about 15 nucleotides) such that a duplex is formed when the oligonucleotide pair is annealed. DNA polymerase can be used to extend the oligonucleotides, resulting in a single, double-stranded nucleic acid molecule per oligonucleotide pair, which then can be ligated into a vector. Isolated nucleic acids can also obtained by mutagenesis. Protein-encoding nucleic acids can be mutated using standard techniques, including oligonucleotide-directed mutagenesis and/or site-directed mutagenesis through PCR. See, *Short Protocols in Molecular Biology*. Chapter 8, Green Publishing Associates and John Wiley & Sons, edited by Ausubel et al, 1992.

VI. Diagnostic Markers

While PD-1 monoclonal antibody therapy is highly successful for some patients, the failure of a large subset of cancer patients to response to PD-1 monoclonal antibody immunotherapy has led to a need to distinguish between responsive and non-responsive patients. One embodiment provides a predictive biomarker to identify patients that will be non-responsive to anti-PD-1/PDL1 therapy and a method of increasing their responsiveness to anti-PD-1/PDL1 therapy. The presence of dysfunctional $CD38^+CD8^+$ T cells, $CD38^+PD-1^+$ T cells, or $CD38^+PD-1^+CD8^+$ T cells in the tumor microenvironment is predictive of failure of anti-PD-1/PD-L1 therapy. In addition, the presence of $CD38^+CD8^+$ T cells, $CD38^+PD-1^+$ T cells, or $CD38^+PD-1^+CD8^+$ T cells in the blood of subjects that have previously received anti-PD-1/PD-L1 therapy is predictive of resistance to anti-PD-1/PD-L1 therapy.

Methods of detecting the presence of specific cells in a heterologous sample are known in the arts. The most common method of detecting immune cell populations is flow cytometry (Aysun, A., et al., *Crit Rev Biotech*, 37:163-176 (2017)). Flow cytometry is a cell analysis technique to make measurements of cells in solution as they pass by the instrument's laser at rates of 10,000 cells per second (or more). The laser detects fluorescently labeled cells in a single-cell suspension. Fluorescence-tagged antibodies can be used to label cells according to protein markers. Cell surface markers can be directly labeled with fluorochrome-conjugated antibodies or cell surface markers can be indirectly labeled using a fluorescent secondary antibody directed against the primary antibody. In one embodiment, the presence of $CD38^+CD8^+$ T cells, $CD38^+PD-1^+$ T cells, or $CD38^+PD-1^+CD8^+$ T cells is detected using a flow cytometer.

Other methods of detecting immune cells include but are not limited to cytometry by time-of-flight, microengraving, and barcoded microchips (Lyons, Y. A., et al., *npj Precision Oncology*, 1:26 (2017)). Cytometry by time-of-flight (CyTOF) uses heavy metal isotopes to label antibodies, and then labeled cells are analyzed by high-throughput spectrometry on a single-cell level. This approach of cell profiling provides more parameters to quantify than traditional flow cytometry, which is limited by overlap between the emission spectra of individual fluorophores. Microengraving is a technique that involves suspension of cells onto an array of microwells, inversion onto a glass slide with capture reagent, an incubation period, and then interrogation of the microarray with a fluorescence scanner. Microengraving is ideal for immune profiling of proteins since it allows for high-throughput identification and quantification of cell lineage and secreted products of lymphocytes, such as cytokines and antigen-specific immunoglobulins. The barcoded microchips assay allows for absolute quantification of both cytosolic and surface proteins of single cells. The microchip system contains microchambers that hold a defined volume or number of cells and houses the barcode, or antibody array for capture, lysis, and detection of various proteins.

In one embodiment, samples are obtained from a subject and analyzed for the presence of $CD38^+CD8^+$ T cells, $CD38^+PD-1^+$ T cells, or $CD38^+PD-1^+CD8^+$ T cells. The presence of $CD38^+CD8^+$ T cells, $CD38^+PD-1^+$ T cells, or $CD38^+PD-1^+CD8^+$ T cells in the sample is indicative of resistance to anti-PD-1/PD-L1 therapy. In one embodiment, the subject is diagnosed as resistant to anti-PD-1/PD-L1 therapy if $CD38^+CD8^+$ T cells, $CD38^+PD-1^+$ T cells, or $CD38^+PD-1^+CD8^+$ T cells are present in the sample. The sample obtained from the subject can be a blood sample or a tumor sample. In one embodiment, the subject that is diagnosed as resistant to anti-PD-1/PD-L1 therapy is administered a different therapeutic. In another embodiment, the subject that is diagnosed as resistant to anti-PD1/PDL1 therapy is administered an anti-CD38/CD8 antibody or anti-PD-1/CD38 bispecific antibody to deplete dysfunctional $CD38^+CD8^+$ T cells, $CD38^+PD-1^+$ T cells, or $CD38^+PD-1^+CD8^+$ T cells and increase the efficacy of the anti-PD-1/PD-L1 therapy.

VII. Kits

Medical kits are also disclosed. The medical kits can include, for example, a dosage supply of one or more of the compositions disclosed herein. The active agent(s) can be supplied alone (e.g., lyophilized), or in a pharmaceutical composition. The active agent(s) can be in a unit dosage, or in a stock that should be diluted prior to administration. In some embodiments, the kit includes a supply of pharmaceutically acceptable carrier. The kit can also include devices for administration of the active agent(s) or composition(s), for example, syringes. The kits can include printed instructions for administering the compound in a use as described above.

Kits designed for the above-described methods are also provided. In one embodiment the kits can include reagents and antibodies for detecting CD38, PD1, and CD8 positive cells in patient samples, the disclosed CD38/CD8 and PD1/CD38 immunomodulatory agents, and an anti-PD1 therapeutic. In another embodiment the kit includes one or more other prophylactic or therapeutic agents useful for the treatment of cancer, in one or more containers.

EXAMPLES

Example 1. PD-1 Blockade Prior to Antigen Priming with Cancer Vaccine Abrogates the Anti-Tumor Immune Effects and Results in Impaired Antigen-Specific CD8+ T-Cell Infiltration into Tumor Materials and Methods
Mice C57BL/6 female mice, 4-6 weeks old, were purchased from The Jackson Laboratory and housed under pathogen-free conditions. For in vitro experiments pMel-1 mice [B6.Cg-Thy1$^a$/Cy Tg(TcraTcrb)8Rest/J] that carry a rearranged TCR transgene (Vβ13) specific for the mouse homolog (pmel-17) of human gp100 (Ji et al, PLoS One, 9:e96650) and OT-1 mice [C57BL/6-Tg(TcraTcrb)1100Mjb/Crl] that have transgenic TCR on CD8' T-cells specific for ovalbumin residues 257-264 in the context of H2Kb were used. All procedures were carried out in accordance with approved Augusta University IACUC animal protocols.
Tumor Cell Line TC-1 cells that were derived by stable transfection of mouse lung epithelial cells with human papillomavirus strain 16 (HPV16) early proteins 6 and 7 (E6 and E7) and activated h-ras oncogene were obtained from Dr. T-C Wu (Johns Hopkins University) (Lin, K. Y., et al., Cancer Res, 56:21-26 (1996)). B16 (melanoma) tumor cell line expressing gp100 was obtained from American Type Culture Collection (Manassas, VA). Cells were grown in RPMI 1640 supplemented with 10% FBS, 2 mM L-glutamine, penicillin (100 U/ml) and streptomycin (100 µg/ml) at 37° C. with 5% $CO_2$ and maintained at a confluence of 70%-80%. The cells were routinely tested for absence of *mycoplasma* by applying PCR. All tests were negative.
Vaccines The CTL epitope from HPV16 E749-57 (9 amino acid (aa) peptide, RAHYNIVTF (SEQ ID NO: 19), 100 µg/mouse) from Celtek Bioscience (Franklin, TN) was used for TC-1 tumor model. For B16 tumor model, gp10025-33 peptide-vaccine was used. The gp100$_{25-33}$ 9-mer peptide (KVPRNQDWL) (SEQ ID NO:20) was purchased from AnaSpec (Fremont, CA) and administered at 100 µg/mouse. Both of the vaccines were used mixed with PADRE (aK-Cha-VAAWTLKAAa, where "a" is D alanine, and "Cha" is 1-cyclohexylalanine)(SEQ ID NO:21), a small 13-mer non-natural pan HLA DR-binding sequence that is a potent T cell epitope (T helper epitope, 20 µg/mouse-Celtek Bioscience, Franklin, TN) and QuilA (adjuvant, 10 µg/mouse-Brenntag, Westbury, NY). Three doses of respective vaccines were administered subcutaneously (s.c.) every seven days (D) in TC-1 or B16 tumor-bearing mice. For therapeutic experiments, mice were vaccinated thrice with an interval of one week between vaccinations while for immune response experiments mice were vaccinated twice.

Various cell types were activated with their respective cognate peptides. The gp100$_{25-33}$ 9-mer peptide (KVPRNQDWL)(SEQ ID NO:20) (ANASPEC Inc.) was used for in vitro activation of magnetically enriched CD8+ T-cells from spleens of pMel-1 mice (Abu, E. R., et al., *Oncoimmunology*, 4(5):e1005448 (2015)) while CD8+ T-cells from OT-1 mice were activated with Ova$_{257-264}$ (SIINFEKL)(SEQ ID NO:22). In some experiments low-affinity variant of Ova$_{257-264}$, termed Ova-V (SIIGFEKL) (SEQ ID NO:23) was used for activation of OT-1 CD8+ T-cells. The purity of the enriched cells was more than 90%.
Antibodies and Reagents Purified anti-mouse anti-PD-1 (RMP1-14 clone, Rat IgG2a) was obtained from MedImmune LLC (Gaithersburg, MD). Live/Dead™ Fixable Near-IR Dead Cell Stain Kit (Cat# L34976) and CellTrace™ Violet Cell Proliferation Kit (Cat# C34557) were obtained from Thermo Fisher Scientific Inc. Appropriately fluorochrome-labeled anti-mouse Abs against CD45, CD3, CD8, Annexin V, CD40L, IFNγ, CD62L, CD44, CD38 and PD-1 were obtained from BD Biosciences for flow cytometric measurements. E7 FITC dextramers were obtained from Immudex. CD8+ enrichment kits (Miltenyi) were used per manufacturer's instructions. All Abs for Western blot analysis and flow cytometry (fluorochrome-labeled), SHP2, p-SHP2 (pY542), Lck, p-Lck (T393), Zap70, p-Zap70 (T319, T352), LAT, p-LAT (Y191), Akt and p-Akt (S473) were purchased from Abcam, Cell Signaling Technology® or BD Biosciences.
Statistical Analysis All statistical parameters (average values, SD, SEM, significant differences between groups) were calculated using GraphPad Prism or Excel as appropriate. Statistical significance between groups was determined by Student's t test or one-way ANOVA with Tukey's multiple comparison post-hoc test (p≤0.05 was considered statistically significant). Survival in various groups was compared using GraphPad Prism using Log-rank (Mantel-Cox) test. SK plots were generated by internally developed software (https://skylineplotter.shinyapps.io/SkyLinePlotter/). Contrary to the survival plot generated using GraphPad Prism, the SK plot gives dynamic simultaneous presentation of tumor volumes and mouse survival at a specific time point.

The receiver operating characteristics (ROC) analysis was used to measure the predictive power of biomarkers using human PBMC and tumor samples. The ROC curve depicts sensitivities and 1-specificities. The area under the ROC curve (AUC) is typically used to measure the predictive power of the biomarker on non-response. It is between 0 and 1. The higher the AUC value is, the better is the predictive power. If we predict the response and non-response by random, the AUC would be 0.50. An AUC of 1.0 represents perfect prediction.

Statistical significance between responding and non-responding patients with respect to the average numbers of CD38+PD-1+CD8+ T-cells in the pre- and post-treatment tumor samples is determined by Student's t test when Gaussian assumption holds, otherwise, the Wilcoxon rank sum test is used.

In the therapeutic experiments, tumors were implanted in C57BL/6 mice by injecting either 7×10$^4$ TC-1 or 0.5×10$^6$ B16 tumor cells/mouse s.c. into the right flank at D0. When tumors measured ~5-6 mm in diameter, mice from appropriate groups (5 mice per group) were injected with vaccine (s.c., total 3 doses, one week apart). Anti-PD-1 was administered intraperitoneally (i.p.) twice weekly throughout the experiment at a dose of 1 mg/kg for TC-1 and 5 mg/kg for B16 tumor models beginning either 3 days before (tPD1 (Pre)) or at the day of vaccination. Tumors were measured every 3-4 days using a digital Vernier caliper and the tumor volume was calculated using the formula: $V=L \times W^2/2$, where V is tumor volume, L is the length of tumor (longer diameter) and W is the width of the tumor (shorter diameter). Mice were monitored for tumor growth and survival. Mice were sacrificed when tumor volume reached 1.5 cm$^3$.

For immune response experiments, TC-1 tumor bearing mice were treated following the same schedule as for the therapeutic experiment above, except only two doses of weekly vaccines were given. Tumor samples were harvested at various time points: D10 i.e., three days after anti-PD-1 treatment; D13 i.e. three days after first vaccination and D20 i.e., three days after second vaccination. Samples were processed using GentleMACS dissociator and the solid tumor homogenization protocol, as suggested by the manufacturer (Miltenyi Biotec, Auburn, CA). Each experiment was repeated at least twice.

Flow Cytometric Analysis of Tumor-Infiltrating Lymphocytes and Apoptosis $1\text{-}2\times10^6$ cells/sample/time point were stained for Live/Dead staining (Invitrogen, ThermoFisher Inc.) followed by fixation and permeabilization. For IFNγ staining BD Cytofix/Cytoperm™ (Cat# 51-2090KZ) and BD Perm/Wash™ (Cat# 51-2091KZ) buffer set was used as per manufacturer's instructions (BD Pharmingen™, San Diego, CA). Data acquisition was performed on FACSCalibur or LSRII (BD Biosciences). Results were analyzed using FlowJo software (TreeStar). Total numbers of $CD3^+$, $CD8^+$, $CD8+E7^+$, Annexin $V^+$, $CD40L^+$, IFNγ+, $CD62L^+$, $CD44^+$, $CD38^+$, and $PD\text{-}1^+$ cells were analyzed within $CD45^+$ hematopoietic cell population and represented in $1\times10^6$ live cells in tumors or on respective populations as shown in respective figures. In addition, expression of CD38 (MFI) was estimated on $PD1^+CD8^+$ T-cell population.

For determination of apoptosis, freshly harvested tumor tissues from variously treated mice were processed into single cell suspensions and stained for CD8, E7CD8 and Annexin V per manufacturer's protocol (BD Biosciences) and FACS acquired.

Results

Sequencing of priming agent like tumor-vaccine, when combined with PD-1 blockade, may have a major impact on therapeutic outcome. Two syngeneic tumor models, TC-1 and B16, were used. Both models have known immune dominant antigens and antigen-specific vaccines available. The CTL epitope from HPV16 E7 peptide is used in vaccine formulation for TC-1 model and gp100 peptide for B16 model. Anti-PD-1 therapy, when initiated simultaneously (FIG. 1A) with vaccine (Vax+αPD1), showed synergy in inhibition of tumor growth in the TC-1 model and increased survival of treated animals while neither vaccine (Vax) nor anti-PD-1 treatment alone affected tumor growth (FIG. 1B-1D). On the other hand, blockade of PD-1 prior to antigenic stimulation, by adding one extra dose of anti-PD-1 (Vax+αPD1 (Pre)) into the same schedule (FIG. 1A), fully abrogated the anti-tumor effects of the combination (FIG. 1B-1D). Similar results were found in the B16 tumor model (FIG. 1E-1G). Hence, these results demonstrate that blocking the PD-1 pathway prior to priming with vaccine abrogates the anti-tumor effects of the concomitant combination treatment.

To understand the reason why PD-1 blockade prior to vaccination leads to complete abrogation of the combination's anti-tumor effect, the T-cell infiltrates in the TME in the same schedule outlined above were profiled. As expected, vaccination resulted in a significant increase in both total $CD8^+$ T-cells as well as E7-specific $CD8^+$ T-cells in the TC-1 model (FIGS. 1H and 1i). The $CD8^+$ T-cells and $E7^+CD8^+$ T-cell infiltration was further increased when anti-PD-1 was given concomitantly with the vaccine. On the other hand, when anti-PD-1 was given prior to the vaccine therapy, the level of total $CD8^+$ T-cells was not changed compared to the vaccine alone group, and was significantly lower compared to the concomitant Vax+αPD1 group. Interestingly, a significant decrease in antigen-specific $CD8^+$ T-cells was observed after pre-treatment with anti-PD-1, resulting in complete elimination of vaccine-induced $E7^+CD8^+$ T-cells (FIG. 1). Anti-PD-1 treatment alone did not show any significant change in the numbers of either $CD8^+$ or antigen-specific $CD8^+$ T-cells compared to untreated control, therefore this group was not included in the subsequent experiments.

The data above demonstrate that PD-1 blockade before antigen priming abrogates the ability of the combination to induce the antigen-specific effector cells and a resultant anti-tumor response. Proper sequencing of vaccine and anti-PD-i is therefore crucial for the success of the combination. Furthermore, both of these tumor models are known to be anti-PD-1 therapy resistant demonstrating that vaccine given with anti-PD-1 enhances the frequency of antigen-specific effector cells in the TME and reverses anti-PD-1 tumor resistance.

Example 2: PD-1 Blockade Prior to Antigen Priming Results in Increased Antigen-Specific $CD8^+$ T-Cell Apoptosis and Prevents Cell Activation in the TME by Inhibition of Downstream T-Cell Signaling Materials and Methods Cell Activation For in vitro activation, magnetically enriched (Miltenyi Biotec) $CD8^+$ T-cells (>95% purity) from pMel-1 mice were cultured in T-cell medium containing RPMI-1640 (Lonza) supplemented with 10% fetal bovine serum (FBS), penicillin (100 U/mL), streptomycin (100 mg/mL), 0.1% β-mercaptoethanol (Life Technologies, Invitrogen), and either IL-2 (100 U/mL) (Peprotech) or anti-PD-1 (MedImmune; clone-RMPI-14; 25 µg/mL) at 37° C./5% $CO_2$. Twenty-four hours later, cells were harvested for Western blot analyses (Ti) or cells were further cultured for 24 h following addition of anti-PD-1 (25 µg/mL) and gp10025-33 peptide (0.2 µM/mL) for 24 h. At the end of incubation, cells were again harvested for Western blot analyses (T2). Finally, cells were cultured for 48 h following the addition of anti-PD-1 (25 µg/mL) and harvested for Western blot analyses (T3). For activation of OT-1 T-cells, magnetically purified (>90%) $CD8^+$ T-cells were incubated either with IL2 (100 U/mL) or αPD-1 (25 µg/mL) for 24 h followed by addition of Ova or Ova-V (1 µg/mL) for an additional 24 h. At the end of incubation, cells were harvested and analyzed by FACS for expression of PD-1, CD38, CD40L and Annexin V.

To check the production of IFNγ by $CD8^+$ T-cells in the TME, freshly acquired tumor samples from variously treated mice were plated at a density of $2\times10^6$ cells/well in a 48 well-plate and incubated in T-cell medium containing 50 ng/ml of PMA (Phorbol 12-myristate 13-acetate (Cat# P1585), 750 ng/ml of ionomycin and 10 µg/ml of brefeldin (Cat# B5936-200UL). Cells were incubated for 4 h/37° C./5% $CO_2$ followed by FACS staining to detect IFNγ and other cell markers.

Western Blot Analysis pMel-1 $CD8^+$ T-cells harvested as above were treated with cell lysis buffer (RIPA buffer+1% phosphatase inhibitor+1% protease inhibitor) for preparing the cell lysates. Protein concentrations in the various cell lysates were determined by Pierce® BCA Protein Assay Kit (ThermoFisher Scientific). 20-30 µg protein was loaded onto Novex™ 4-20% Tris-Glycin Mini Gels (ThermoFisher Scientific) followed by transfer onto nitrocellulose membranes. Membranes were blocked with 3% BSA in Tris-buffer followed by overnight probing of the proteins with Abs directed against mouse total or phosphorylated SHP2, Lck, Zap70, LAT and Akt. Blots were developed with rabbit anti-mouse Horseradish Peroxidase (HRP) labeled secondary Abs. Densitometric analysis of the bands was performed using a software from LI-COR (https://www.licor.com/bio/products/software/image_studio_lite/).

Results

Figure 2D:
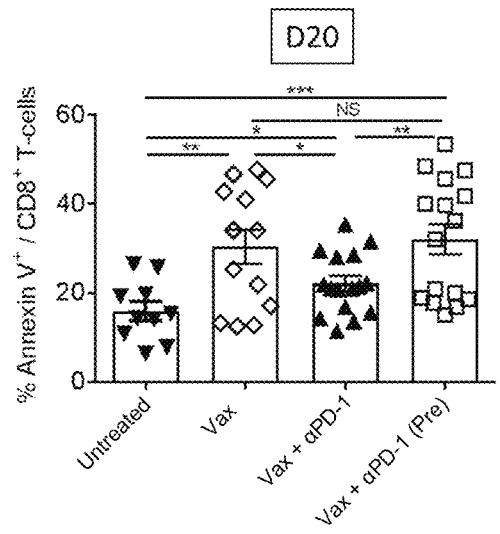
FIGS. 2D and 2E are bar graphs showing percent annexin $V^+$ cells per $CD8^+$ T cells at D20 (FIG. 2D) and Day 13 (FIG. 2E) after tumor injection in untreated, treated with αPD1, treated with Vax, treated with Vax and αPD1, pretreated with αPD1 and Vax.
Figure 2E:
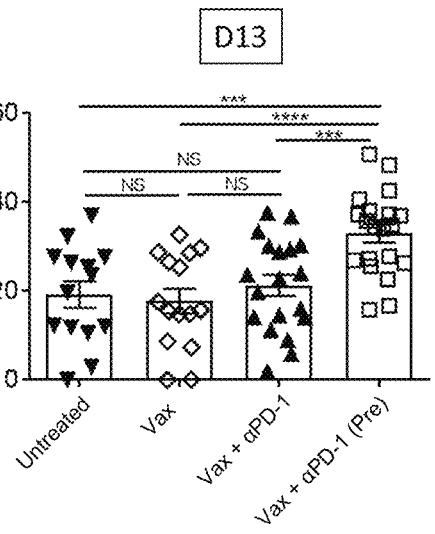
Figure 2F:
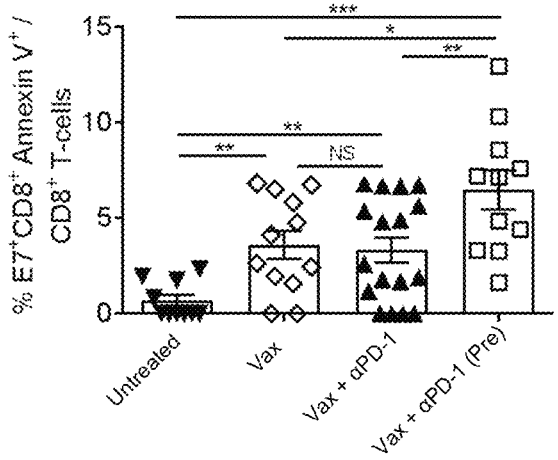
FIGS. 2F and 2G are bar graphs showing percent $E7^+CD8^+$ annexin $V^+$ cells per $CD8^+$ T cells at D20 (FIG. 2F) and Day 13 (FIG. 2G) after tumor injection in untreated, treated with αPD1, treated with Vax, treated with Vax and αPD1, pretreated with αPD1 and Vax.
Figure 2G:
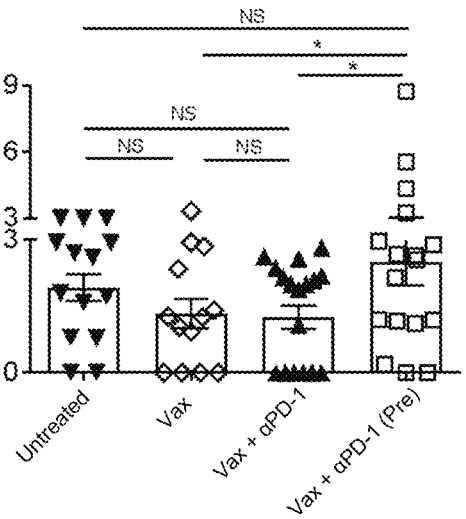

The results described in Example 1 above suggest that blocking anti-PD-1 prior to initiation of vaccine treatment potentially induces immunologic changes early during the course of treatment that affect the outcome of therapy. Therefore, the effect of such treatment on the immune infiltrate 3 days after the priming dose of vaccine given with anti-PD-1 (D13) was analyzed (FIG. 2A). There was no significant change in the tumor-infiltration of total $CD8^+$ T-cells (FIG. 2B). However, while the concomitant administration of anti-PD-1 enhanced the $E7^+CD8^+$ T-cell infiltration as early as 3 days after the first vaccination, adding anti-PD-1 prior to the vaccine led to complete abrogation of this enhancement in the TME (FIG. 2C). In fact, the frequency of $E7^+CD8^+$ T-cells following PD-1 blockade prior to the vaccine was similar to untreated control (FIG. 2C). Therefore, it was determined whether this loss in antigen-specific $CD8^+$ T-cells in the TME is potentially due to an early induction of apoptosis and checked the expression of annexin V in $CD8^+$ T-cells in the TME. A significant increase in the apoptotic cell death of total and antigen-specific $CD8^+$ T-cells was observed when anti-PD-1 was started before vaccine treatment compared to the vaccine or concomitant treatments (FIG. 2D-2G). Notably, antigen-specific $CD8^+$ T-cells continued to undergo apoptosis on D13 and D20 (FIGS. 2F and 2G).

Figure 2H:
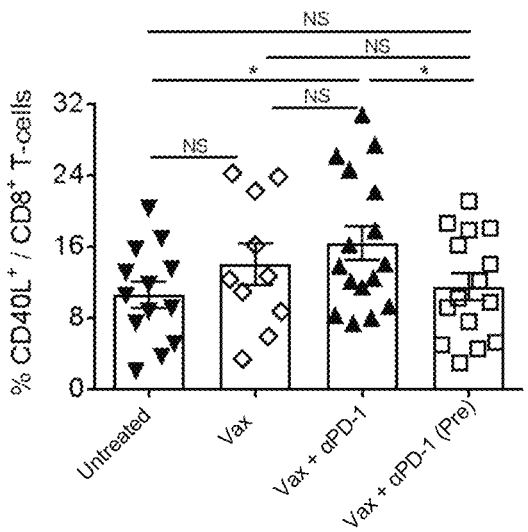
FIGS. 2H and 2I are bar graphs showing percent $CD40L^+$ cells per $CD8^+$ T cells at D20 (FIG. 2H) and Day 13 (FIG. 2I) after tumor injection in untreated, treated with αPD1, treated with Vax, treated with Vax and αPD1, pretreated with αPD1 and Vax.
Figure 2I:
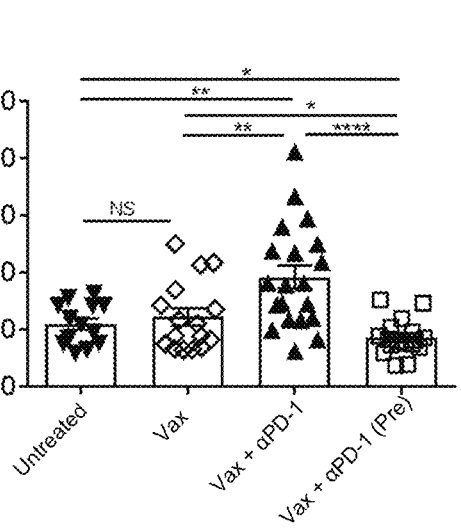
Figures 2J, 2K:
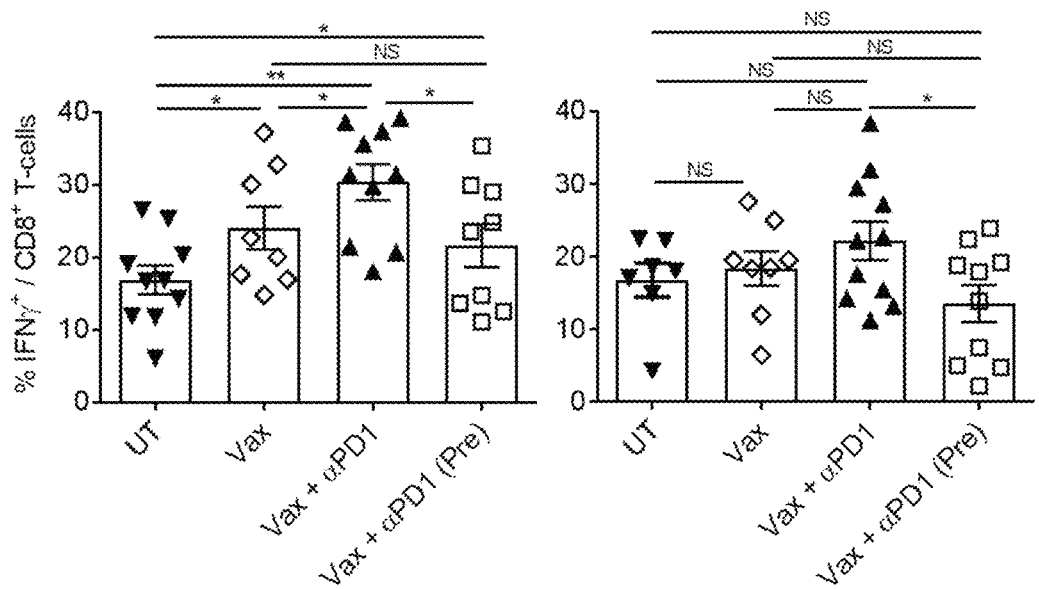
FIGS. 2J and 2K are bar graphs showing percent IFNγ$^+$ cells per $CD8^+$ T cells at D20 (FIG. 2J) and Day 13 (FIG. 2K) after tumor injection in untreated, treated with αPD1, treated with Vax, treated with Vax and αPD1, pretreated with αPD1 and Vax.

One of the possible causes of apoptosis is the induction of activation-induced cell death (AICD) (Shrimali, R K., et al., Cancer Immunol Res, 5:755-766 (2017)). It is known that anti-PD-1 therapy reinvigorates exhausted T-cells (Trautmann, L., et al., Nat Med, 12:1198-1202 (2006); Day, C. L., et al., Nature, 443"350-354 (2006)) and reverses inhibition of weak TCR signals leading to $CD8^+$ T-cell activation (Patsoukis, N., et al., Front Immunol, 8:330 (2017); Latchman, Y., et al., Nat Immunol, 2:261-268 (2001)). Therefore, the expression of CD40L and IFNγ on $CD8^+$ T-cells in the TME of variously treated mice were tested as a marker of cell activation and functional status (Refaeli, Y., et al., J Exp Med, 196:999-1005 (2002); Lohman, B. L., et al., J Virol, 72:7815-7821 (1998); Dondi, E., et al., J Immunol, 173: 3740-3747 (2004)). As expected, compared to vaccine alone, concurrent treatment resulted in a significant increase in the numbers of activated $CD8^+$ T-cells at D13 (3 days after antigen priming) (FIG. 2I). In addition, concomitant vaccine and anti-PD-1 treatment resulted in increased numbers of IFNγ-producing cells compared to vaccine alone at D20 (3 days after antigen boosting) (FIG. 2J). However, as expected, the activation status was comparable between the two groups (FIG. 2H). On the other hand, the numbers of $CD40L^+$, IFNγ-producing effector cells decreased significantly when PD-1 was blocked prior to the priming, compared to its concomitant blockade with the vaccine (FIG. 2H-2K). These results demonstrate that anti-PD-1 given before the vaccine treatment did not induce further activation of T-cells and therefore the observed apoptosis is not due to AICD.

Figure 3A:
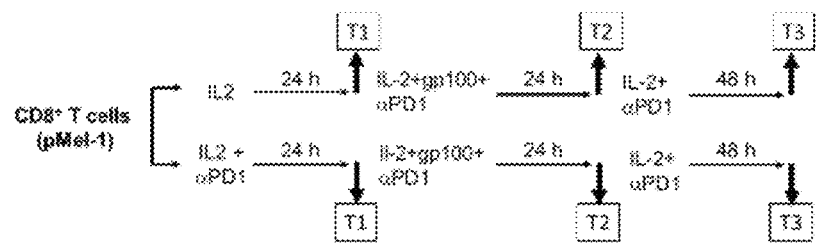
FIG. 3A is a schematic representation of the experimental design of FIG. 3. Briefly, $CD8^+$ T cells were treated with either IL-2 or αPD1 for 24 hours (Ti). Each group was then treated with gp100+/αPD1 for 24 hours (T2) and αPD1 for an additional 24 hours (T3). Cells were harvested at each of the time points.
Figures 3B, 3C, 3D:
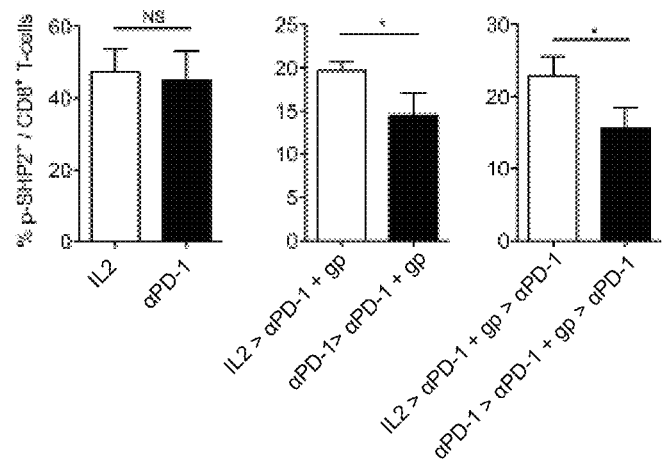
FIGS. 3B-3P are bar graphs showing expression of p-SHP2 (FIGS. 3B-3D), p-Lck (FIGS. 3E-3G), p-Zap70 (FIGS. 3H-3J), p-LAT (FIGS. 3K-3M), and p-Akt (FIGS. 3N-3P) for $CD8^+$ T cells from each of the groups outlined in FIG. 3A.
Figures 3E, 3F, 3G:
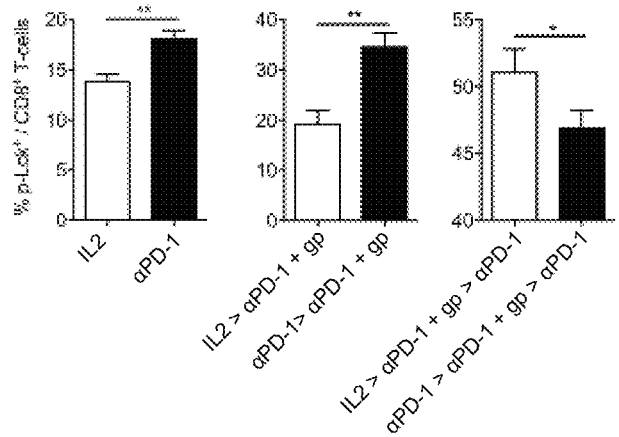
Figures 3H, 3I, 3J:
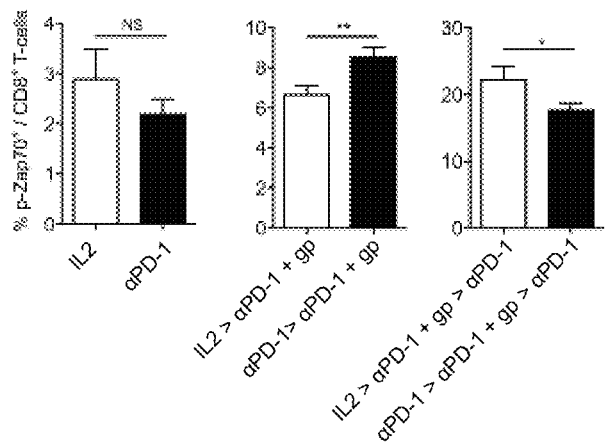
Figures 3K, 3L, 3M:
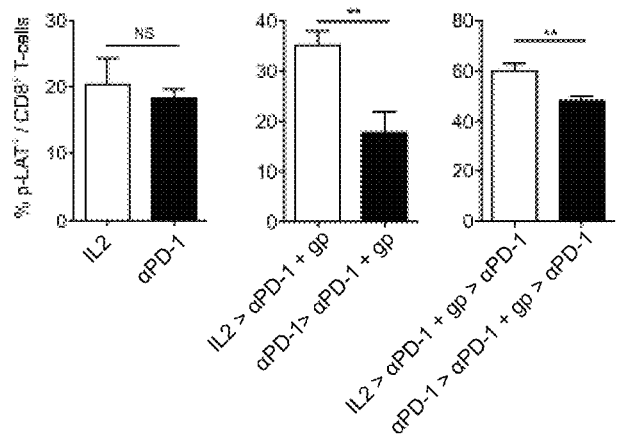
Figures 3N, 3O, 3P:
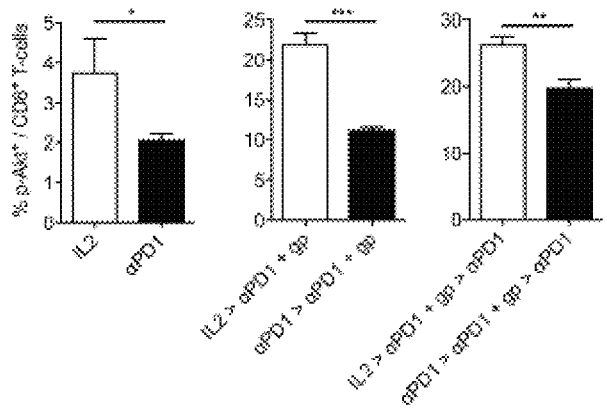

One of the mechanisms of non-AICD mediated cell death is improper cell activation that is due to impaired TCR mediated cell signaling. Hence, to delineate the effect of anti-PD-1 on TCR signaling, $CD8^+$ T-cells were obtained from pMel-1 mice (Overwijk, W. W., et al., J Exp Med, 188:277-286 (1998)) and activated them with cognate gp100 peptide with or without prior anti-PD-1 treatment (FIG. 3A). The activity of the effector kinases (Lck and Zap70), which are required for TCR mediated cell activation and are negatively regulated by PD-1/SHP2 signaling (Wang, H., et al., Cold Spring Harb Perspect Biol, 2:a002279 (2010); Katz, Z. B., et al., Nat Immunol, 18:86-95 (2017); Yokosuka, T., et al., J Exp Med, 209:1201-1217 (2012)), was determined. SHP2 phosphorylation is known to inhibit T-cell activation through inhibition of Lck phosphorylation (Chen, L., et al., Nat Rev Immunol, 13:227-242 (2013)). Further, PD-1 blockade with simultaneous TCR stimulation is known to release the brake on cell activation by inhibiting SHP2 phosphorylation (Boussiotis, V A, N Eng J Med, 375:1767-1778 (2016)). Blockade of PD-1 prior to peptide stimulation led to a significant decrease in phosphorylation of SHP2 (FIG. 3B) while enhancing phosphorylation of Lck and Zap70 in $CD8^+$ T-cells (FIGS. 3E and 3H). Interestingly, despite further decrease in p-SHP2 (FIG. 3C), Lck and Zap70 phosphorylation was significantly decreased with subsequent addition of anti-PD-1 (FIGS. 3F and 3I). Moreover, the kinase activity of Zap70 as determined by the phosphorylation of LAT required for triggering of downstream TCR signaling as well as the phosphorylation of Akt was significantly reduced when cells were treated with anti-PD-1 before peptide stimulation (FIGS. 3K and 3N). In contrast, when anti-PD-1 was given together with peptide stimulation, there was no change in the phosphorylation status of Lck and Zap70 (FIGS. 3G and 3J) and significant increase in phosphorylation of LAT and Akt (FIGS. 3M and 3P). Taken together, these results show that simultaneous treatment with anti-PD-1 and antigen priming induces T-cells that maintain their functional status as evident by upregulated LAT and Akt leading to cell activation and IFNγ production. However, anti-PD-1 given prior to priming drives the T-cells into a non-responsive state where LAT and Akt do not get phosphorylated and hence cells fail to get activated and show effector functions leading to cell death.

Figures 4A, 4B:
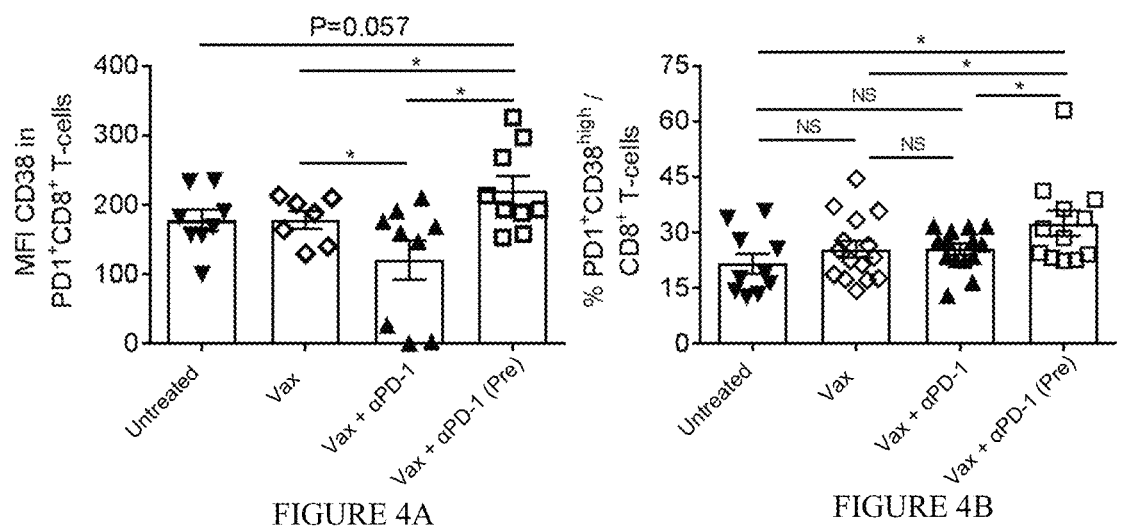
FIG. 4A and FIG. 4C are bar graphs showing the expression of CD38 on $PD1^+CD8^+$ T cells (FIG. 4A) or $PD1^+E7^+CD8^+$ T cells (FIG. 4C).
FIG. 4B is a bar graph showing percent $PD1^+CD38^{high}$ cells per $CD8^+$ T cells.
Figures 4C, 4D:
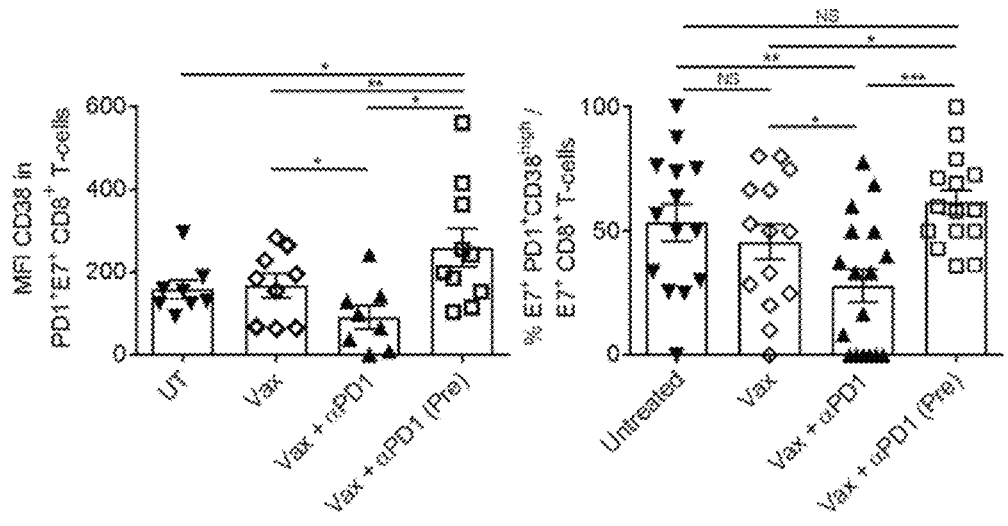
FIG. 4D is a bar graph showing percent $E7^+PD1^+CD38^{high}$ cells per $E7^+CD8^+$ T cells.
Figure 4E:
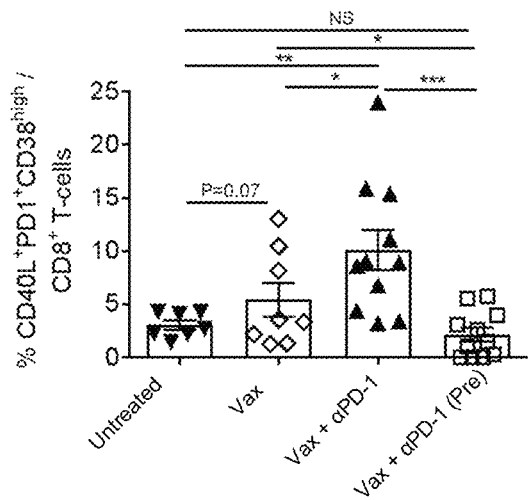
FIG. 4E is a bar graph showing percent $CD40L^+PD1^+CD38^{high}$ cells per $CD8^+$ T cells.
Figure 4F:
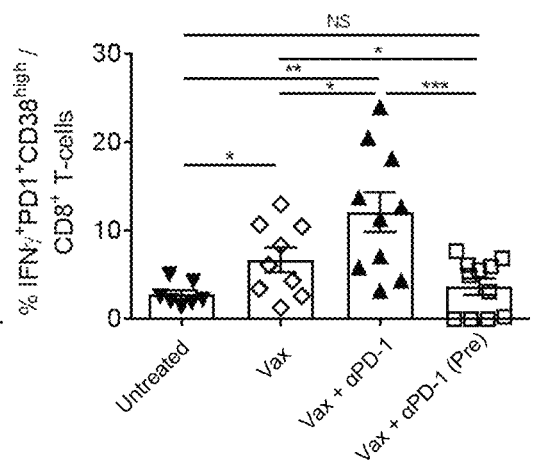
FIG. 4F is a bar graph showing percent IFNγ$^+PD1^+CD38^{high}$ cells per $CD8^+$ T cells.
Figure 4G:
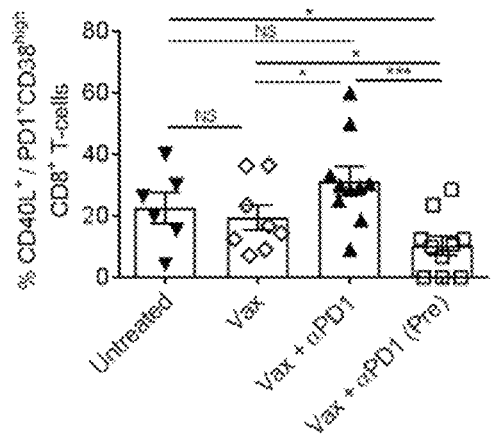
FIG. 4G is a bar graph showing percent $CD40L^+$ cells per $PD1^+CD38^{high}$ $CD8^+$ T cells.
Figure 4H:
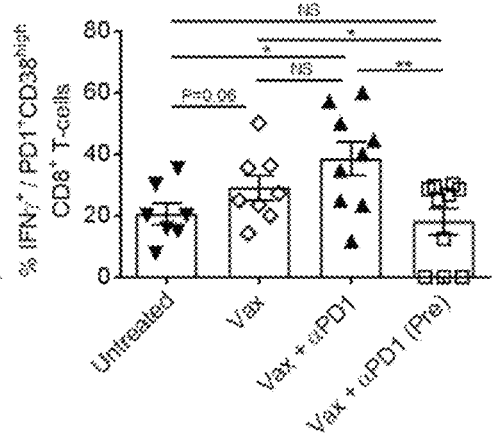
FIG. 4H is a bar graph showing percent IFNγ$^+$ cells per $PD1^+CD38^{high}CD8^+$ T cells.

Example 3: PD-1 Blockade Prior to Antigenic Stimulation Generates Dysfunctional $CD8^+$ T-Cells Materials and Methods
See methods in Example 1 above.
Results $PD1^+CD38^{high}$ $CD8^+$ T-cells have been described as a population of dysfunctional cells that fail to respond to antigenic stimulation and do not elicit effector functions (Philip, M., et al., Nature, 545:452-456 (2017)), similar to the characteristics of cells generated after PD-1 blockade prior to antigen priming as described above. Therefore, the expression of CD38 on $PD1^+CD8^+$ T-cells was determined following concomitant or prior anti-PD-1 treatment with respect to vaccine in TC-1 tumor-bearing mice. Interestingly, anti-PD-1 treatment prior to antigenic priming led to a significant increase in the expression of CD38 (MFI) as well as in the numbers of $PD1^+CD38^{high}$ total and antigen-specific $CD8^+$ T-cells in comparison to vaccine alone group (FIGS. 4A-4D). On the other hand, when anti-PD-1 was given simultaneously with the tumor-specific antigen, $PD1^+CD8^+$(FIG. 4A) as well as antigen-specific $PD1^+CD8^+$(FIG. 4C) T-cells expressed significantly lower levels of CD38 (MFI). Furthermore, this treatment significantly reduced the numbers of antigen-specific $PD1^+CD38^{high}$ $CD8^+$ T-cells compared to vaccine-alone as well as anti-PD-1 pre-treated groups in the TME (FIG. 4D).

Figure 4I:
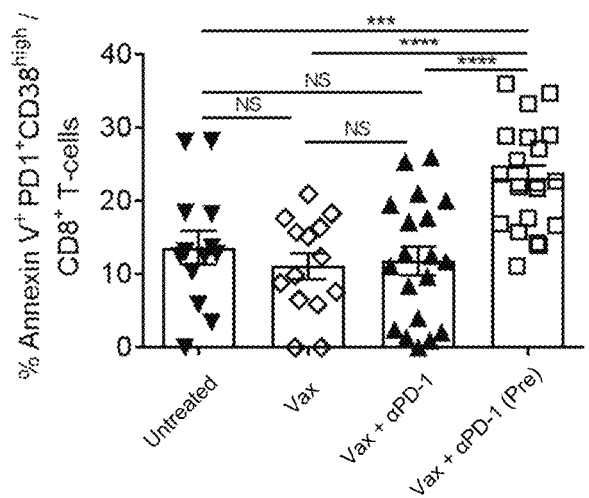
FIG. 4I is a bar graph showing percent annexin $V^+PD1^+CD38^{high}$cells per $CD8^+$ T cells.
Figure 4J:
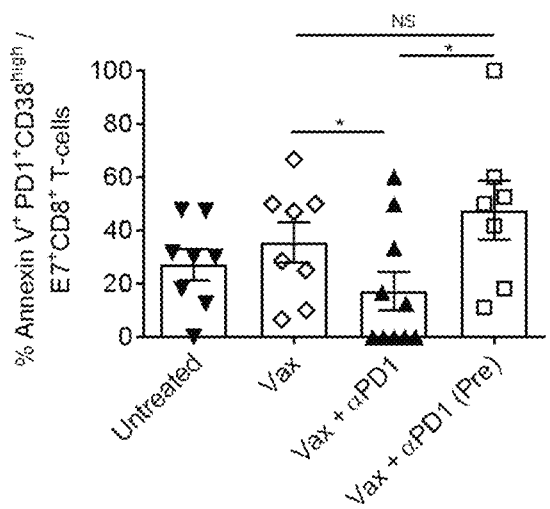
FIG. 4J is a bar graph showing percent annexin $V^+PD1^+CD38^{high}$ cells per $E7^+CD8^+$ T cells.

To check the functionality of these cells generated after various treatments, CD8+ T-cells from treated mice were activated and CD40L expression and IFNγ production were determined. PD1+CD38$^{high}$ cells induced as a result of anti-PD-1 pre-treatment were dysfunctional as these failed to upregulate CD40L and did not produce IFNγ after antigenic re-stimulation (FIGS. 4E-4H). On the contrary, the majority of cells that were generated by simultaneous anti-PD-1 and vaccine treatment had low expression of CD38 on PD1+CD8+ T-cells (PD1+CD381$^w$ T-cells) (FIGS. 4A and 4C) and were highly functional as evident by upregulated CD40L and IFNγ production (FIGS. 4E-4H). Moreover, dysfunctional PD1+CD38$^{high}$ CD8+ T-cells induced after anti-PD-1 when administered prior to vaccine also showed significantly higher apoptosis in both total and antigen-specific CD8+ T-cells (FIGS. 4I and 4J). These data clearly indicate that blocking PD-1 signaling prior to antigenic stimulation drives the antigen-specific CD8+ T-cells into a dysfunctional state early (D13) during the course of antigenic stimulation while they remained functional when PD-1 signaling was blocked concomitant to TCR stimulation.

Figure 4K:
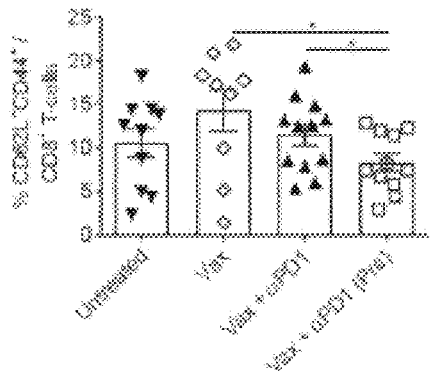
FIG. 4K is a bar graph showing percent $CD62L+CD44^+$ cells per $CD8^+$ T cells.
Figure 4L:
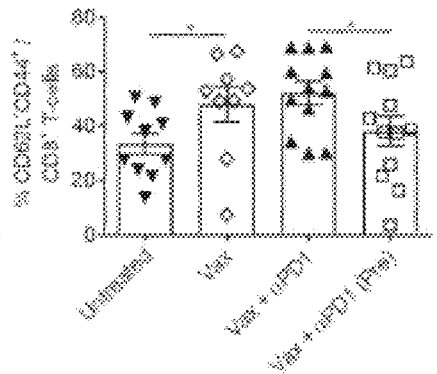
FIG. 4L is a bar graph showing percent CD62L⁻CD44⁺ cells per CD8⁺ T cells. The experimental groups for FIGS. 4A-4L are tumor bearing mice either untreated, treated with αPD1, treated with Vax, treated with Vax and αPD1, pretreated with αPD1 and Vax.

Since CD8+ T-cells did not get activated, which is necessary for memory generation, it is believed that anti-PD-1 treatment prior to antigenic stimulation would result in impaired immune-memory generation. Indeed, it was found that mice that were treated with anti-PD-1 prior to vaccine treatment had significantly lower central (CD62L+CD44+) (FIG. 4K) and effector 10 memory (CD62L-CD44+) (FIG. 4L) T cells than vaccine-alone or concomitant (Vax+αPD1) treatment groups. In conclusion, PD-1 blockade prior to vaccine treatment induces terminal dysfunctionality in antigen-specific CD8+ T-cells that results in reduced memory generation and increased cell death.

Figure 5A:
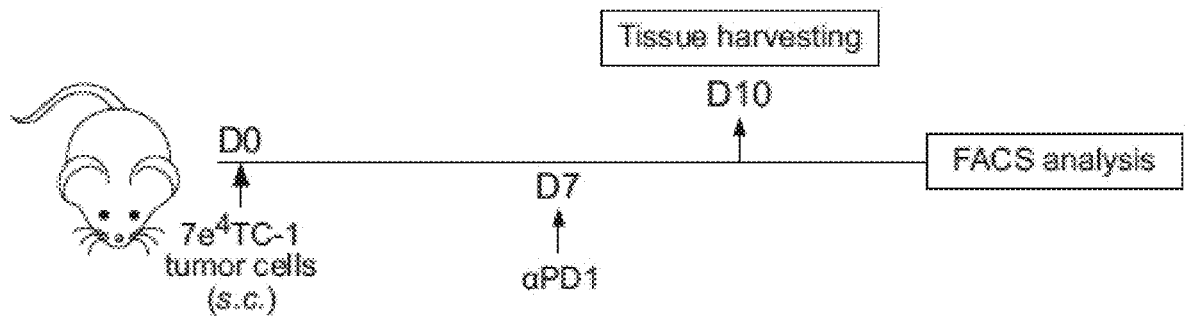
FIG. 5A is a schematic illustration of the experimental design for FIG. 5. Briefly, mice were injected with TC1 tumor cells at Day 0 (D0) and were administered αPD1 at Day 7 (D7).
Figure 5B:
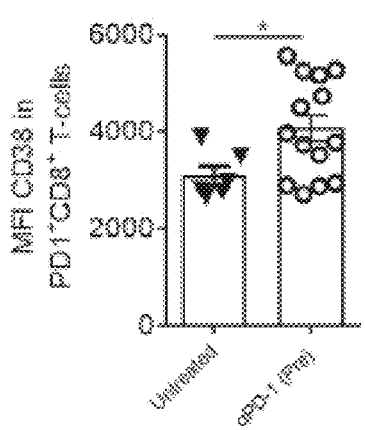
FIG. 5B is a bar graph showing CD38 expression in PD1⁺CD8⁺ T cells.
Figure 5C:
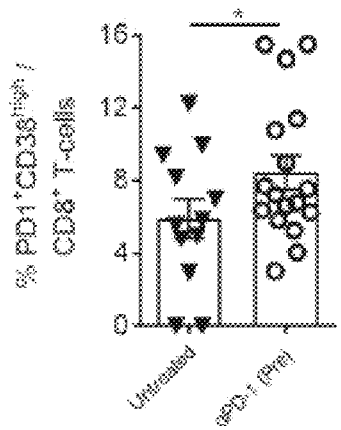
FIG. 5C is a bar graph showing percent PD1⁺CD38$^{high}$ cells per CD8⁺ T cells.
Figure 5D:
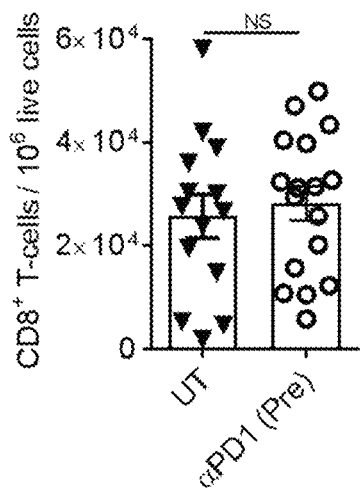
FIG. 5D is a bar graph showing CD8⁺ T cells per 10⁶ live cells.
Figure 5E:
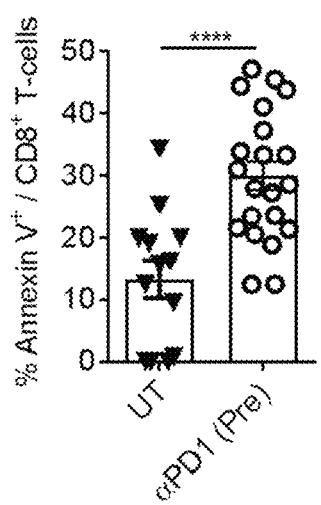
FIG. 5E is a bar graph showing percent annexin V⁺ cells per CD8⁺ T cells.
Figure 5F:
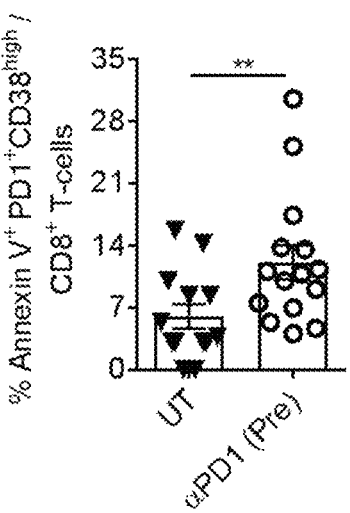
FIG. 5F is a bar graph showing percent annexin V⁺PD1⁺CD38$^{high}$ cells per CD8⁺ T cells. The experimental groups for FIG. 5B-5F are tumor bearing mice either untreated or pretreated with αPD1.

Example 4: PD-1 Blockade on Suboptimally Primed CD8+ T-Cells Induces Dysfunctional PD1+ CD38$^{high}$ CD8+ T-Cells Both In Vivo and In Vitro Materials and Methods
See methods for Example 1 above.
Results
As outlined above, the treatment with anti-PD-1 results in induction of dysfunctional PD1+CD38$^{high}$ T-cells in mice that were treated prior to proper priming. To determine if treatment with anti-PD-1 leads to generation of these dysfunctional cells in the absence of strong antigenic stimulation, TC-1 tumor bearing mice were given a single dose of anti-PD-1, 7 days after tumor injection. Three days after anti-PD1 treatment (Day 10), the phenotype of CD8+ T-cells was analyzed in the TME (FIG. 5A). Administration of a single dose of anti-PD-1 significantly increased the expression of CD38 (MFI) on PD1+CD8+ T-cells resulting in a significant increase in the numbers of PD1+CD38$^{high}$ CD8+ T-cell population in the TME (FIGS. 5B-5C). It was also found that compared to untreated control, PD-1 blockade resulted in 2-3 times increased in annexin V expression in both total and PD1+CD38$^{high}$ CD8+ T-cells at D10, despite the lack of change in the numbers of total CD8+ T-cells in the TME (FIGS. 5D-5F). These results suggest that blocking PD-1/PD-L1 pathway under suboptimal antigenic stimulatory conditions in the TME predisposes CD8+ T-cells towards dysfunctionality and apoptosis-mediated cell death.

Figure 5G:
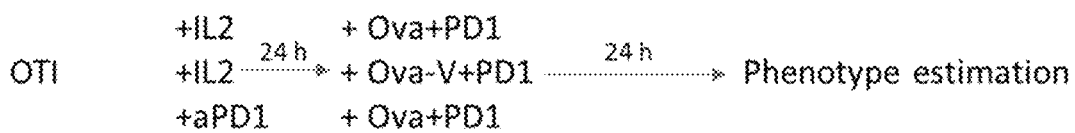
FIG. 5G is a schematic representation of the experimental design for FIGS. 5H-5L. Briefly, OT-I cells were treated with IL2 or αPD1 for 24 hours and were then treated with Ova +PD1 or Ova-V+PD1 for 24 hours. The experimental groups for FIG. 5H-5J are OT-I cells treated with Ova or Ova-V.
Figure 5H:
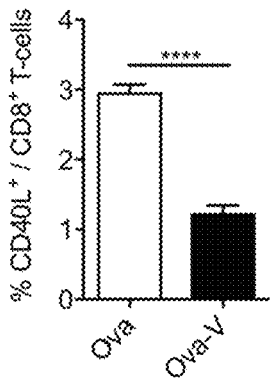
FIG. 5H is a bar graph showing CD40L expression in CD8⁺ T-cells with either Ova treatment or Ova-V treatment.
Figure 5I:
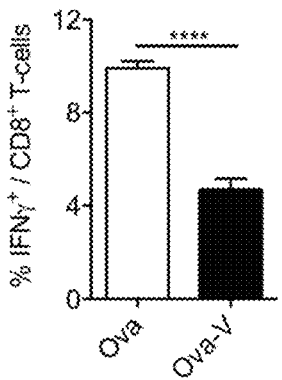
FIG. 5I is a bar graph showing IFNγ expression in CD8⁺ T-cells with either Ova treatment or Ova-V treatment.
Figure 5J:
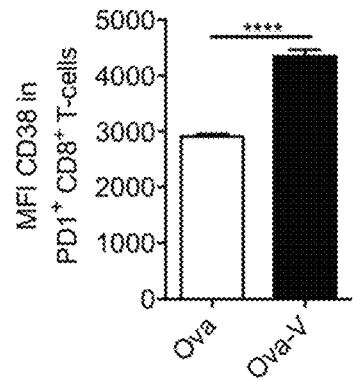
FIG. 5J is a bar graph showing MFI of CD38 in PD1⁺CD8⁺ T cells. The experimental groups for FIGS. 5K-5L are OT-I cells treated with Ova, IL2 treatment followed by Ova+αPD1 treatment, Ova-V treatment, IL2 treatment followed by Ova-V+αPD1 treatment, and αPD1 treatment followed by Ova+αPD1 treatment.
Figure 5K:
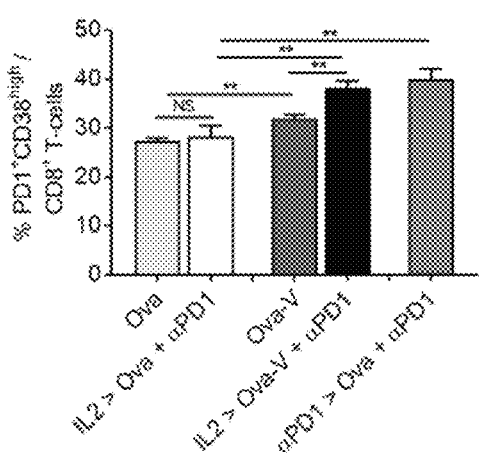
FIG. 5K is a bar graph showing percent PD1⁺CD38$^{high}$ cells per CD8⁺ T-cells.
Figure 5L:
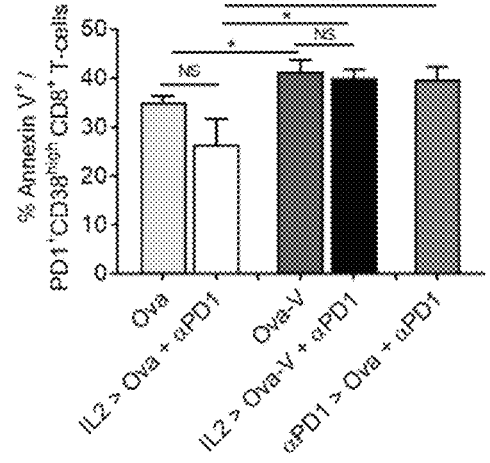
FIG. 5L is a bar graph showing percent annexin V positive PD1⁺CD38$^{high}$ CD8⁺ T cells.

Accordingly, it is thought that anti-PD-1 increases dysfunctional PD1+CD38$^{high}$ CD8+ T-cells when given in the presence of a suboptimal T-cell priming environment. To test this the level of induction of dysfunctional PD1+CD38$^{high}$ cells in CD8+ T-cells from OT-1 mice stimulated either with high-affinity antigen (Ova; optimum priming) or with low-affinity antigen (Ova-V; subpriming) with or without anti-PD-1 treatment were compared (FIG. 5G). As expected, TCR stimulation with low-affinity Ova-V antigen led to a significantly lower level of cell activation as shown by CD40L expression and by IFNγ production than when TCR was engaged with high-affinity antigen, Ova (FIGS. 5H and 5I). Expression of CD38 in PD1+CD8+ T-cells measured by MFI (FIG. 5J), and the numbers of PD1+CD38$^{high}$ CD8+ T-cells (FIG. 5K) induced after Ova-V stimulation were significantly higher compared to Ova stimulation and showed increased apoptosis (FIG. 5L). Furthermore, treatment of Ova-V stimulated CD8+ T-cells with anti-PD-1 resulted in an increase in the numbers of PD1+CD38$^{high}$ cells (FIG. 5K). On the contrary, treatment of Ova-stimulated CD8+ T-cells with anti-PD-1 showed no change in the numbers of PD1+CD38$^{high}$ cells (FIG. 5K). However, blocking PD1 prior to priming with Ova resulted in significant increase in the dysfunctional T cell phenotype (FIG. 5K). As expected, these PD1+CD38$^{high}$ T-cells underwent apoptosis-mediated cell death (FIG. 5L).

These results demonstrate that the suboptimal priming of the CD8+ T-cells induces higher numbers of dysfunctional PD1+ CD38$^{high}$ CD8+ T-cells and their frequency further increases upon anti-PD-1 therapy potentially leading to therapeutic failure.

Example 5: Number of PD1+CD38$^{high}$ CD8+ T-Cells in Tumors Correlates with Anti-PD-1 Therapeutic Response in Patients Materials and Methods
Human Samples and Processing
Tumor Samples:
The expression of CD38 and PD-1 in CD8+ T-cells (FIGS. 5A and 5B) is an unpublished dataset from 48 tumor samples from a cohort of 32 metastatic melanoma patients treated with either anti-PD-1 (n=37) or anti-PD-1/anti-CTLA4 (n=1 1). Patient responses were evaluated using RECIST criteria (Eisenhauer, E. A., et al., *Eur J Cancer*, 45:228-247 (2009)). For this analysis we focused on individual tumor samples and classified them into two categories: responder (regression=R; n=17, including CR/PR samples) and non-responder (progression=NR; n=31, including SD/PD samples) based on radiologic tumor assessments. Fresh tumor biopsies were dissociated using the human tumor dissociation kit (Miltenyi Biotec; 130-095-929), sorted using a BD Fusion instrument into 96 well plates (Eppendorf, 951020401) containing 10 μl of lysis buffer (TCL buffer, Qiagen, 1031576; containing 1% 13-mercaptoethanol) using the anti-human antibodies: FcX (Biolegend, 422302), Zombie violet (Biolegend, 77477), CD45-PE (Biolegend, 304008), CD3-APC (Biolegend, 300412), CD235a-APC/Cy7 (Biolegend, 349116) and HLA-A,B,C-FITC (Biolegend, 311426). Immediately after sorting the plates were stored at −80° C. until processing. Libraries were generated for CD45+ cells using a modified version of the full length Smart-seq2 protocol as recently described (Villani, A. C., et al., *Science*, 356:6335, (2017)), resulting in a median of ~1.4 million paired-end reads and median of 2588 genes detected per cell. Sequencing was performed on a NextSeq 500 sequencer (Illumina). A total of 16,291 CD45+ cells or 6,350 CD8+ T-cells that passed quality control were used for downstream analysis. For each sample, we computed the fraction of CD38+PD-1+ cells out of CD8+ T-cells. A cutoff of log 2(TPM+1)>=2 was used to define a gene as expressed in each single cell.

PBMC Samples:

Human PBMC samples from stage IV melanoma patients at baseline and up to 3 on-treatment visits (collected approximately every 3 weeks) on pembrolizumab therapy from 15 responders and 16 non-responders were from a previously reported clinical trial (NCT01295827) (Huang, A. C., et al., Nature, 545:60-65 (2017)). PBMCs were thawed and stained with a fixable Aqua viability dye (Invitrogen) and a cocktail of antibodies to the following surface markers: CD8-Qdot605 (Invitrogen, 3B5), PD-1-PE (BD, MIH4) and CD38-PerCP-Cy5.5 (Biolegend, HIT2). Control stains were also performed on each sample using isotype control antibodies for PD-1 and CD38 to determine marker positivity. Stained cells were acquired on a BD Biosciences LSRFortessa and analyzed using FlowJo software (FlowJo, LLC).

Results

Figure 6A:
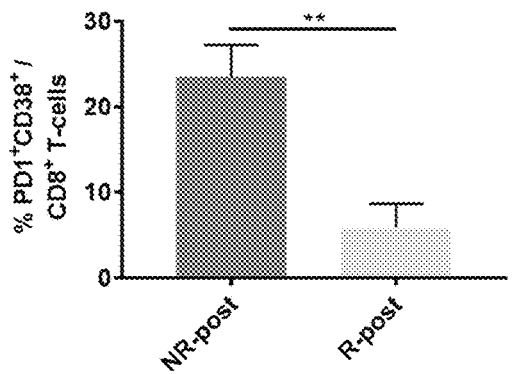
FIG. 6A is a bar graph showing post-treatment average frequency of CD38⁺PD-1⁺CD8⁺ cells in tumor samples from patients that were non-responsive to anti-PD1 therapy (NR-post) and patients that were responsive to anti-PD1 therapy (R-post).
Figure 6B:
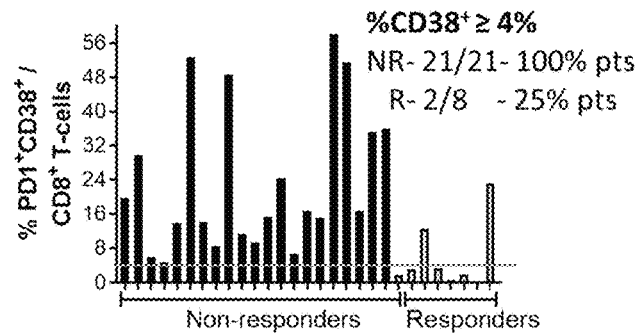
FIG. 6B is a bar graph showing individual frequencies from FIG. 6A. 21 non-responders are shown as black bars and 8 responders are shown as gray bars. The horizontal line depicts the cut off limit where at least 4% or more CD8+ T cells were PD1+CD38+.

The data outlined above show that treatment with anti-PD-1 prior to proper priming leads to an increase in the frequency of dysfunctional PD1+CD38$^{high}$ CD8+ T-cells and failure of therapy. On the other hand, mice that responded were primed simultaneously with anti-PD-1 and showed no increase in PD1+CD38$^{high}$ CD8+ T-cells after therapy. To test whether these cells are also important in predicting response to PD-1 blockade in humans, the levels of CD38+PD1+CD8+ T-cells were evaluated using single cell RNA sequencing, in baseline and post-treatment responding and non-responding metastatic melanoma samples (n=48), from patients (n=32) treated with either anti-PD-1 or anti-PD1CTLA4 antibodies. Analysis of post-therapeutic non-responding tumor samples (n=21), found that the fraction of CD38+PD-1 CD8+ T-cells was significantly higher compared to the responder lesions (n=8) (p≤0.01) (FIG. 6A-6B). Interestingly, it was further observed that 100% of the non-responding patients had at least more than 4% CD38+ cells in PD-1+CD8+ population in the TME compared to only 25% of the responding patients (p≤0.0001) (FIG. 6B), with a positive predictive value (PPV) of 0.913, negative predictive value (NPV) of 1.0, sensitivity and specificity of 1.0 and 0.75 respectively, and AUC of 0.887 (Table 1); indicating a strong potential for CD38+PD-1+CD8+ T-cells fraction in the TME to serve as a biomarker for post-therapeutic outcome.

Figure 6C:
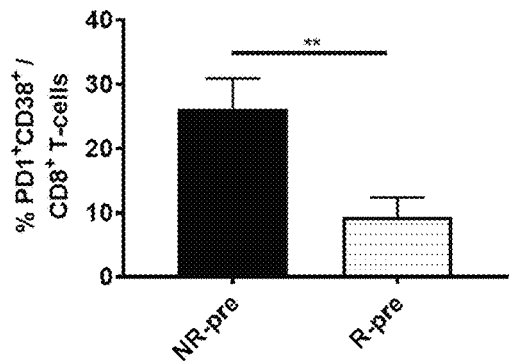
FIG. 6C is a bar graph showing pre-treatment average frequency of CD38⁺PD-1⁺CD8⁺ cells in tumor samples from patients that were non-responsive to anti-PD1 therapy (NR-pre) and patients that were responsive to anti-PD1 therapy (R-pre).
Figure 6D:
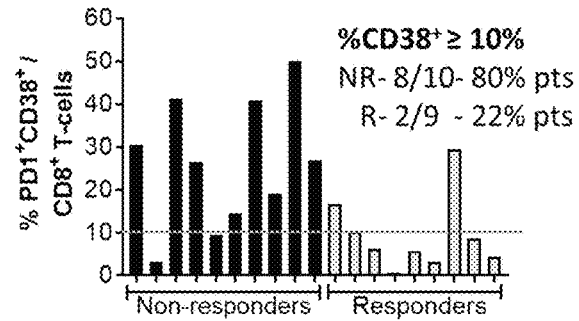
FIG. 6D is a bar graph showing individual frequencies from FIG. 6C. 10 non-responders are shown as black bars and 9 responders are shown as gray bars. The horizontal line depicts the cut off limit where at least 10% or more CD8⁺ T cells were PD1⁺CD38⁺in the tumors.

Based on the above post-therapy patient findings, and since most of the patients have suboptimally primed CD8+ T-cells in the TME prior to therapy (Frey, A B, and Monu, N. Immunol Rev, 222:192-205 (2008)), potentially leading to development of the dysfunctional PD1+CD38$^{high}$ CD8+ T-cells phenotype (FIGS. 5J and 5K), it was determined whether the higher level of these cells also exists prior to anti-PD-1 therapy and can predict outcome. Indeed, the fraction of PD1+CD38+CD8+ T-cells in the tumor samples obtained prior to therapy (n=19) from the non-responders (n=10), was significantly higher compared to responders (n=9; p≤0.01) and found that 25% of PD-1+CD8+ T-cells expressed CD38+in non-responder patients vs. less than 5% in responders (FIG. 6C). Furthermore, it was found that 80% of the non-responding patients had more than 10% CD38+ T-cells in PD1+CD8+ population, compared to only 22% of responding patients (p≤0.023; FIG. 6D). An AUC of 0.833 with a PPV of 0.727 and NPV of 0.75 suggests that CD38+PD-1+CD8+ T-cells fraction in the TME can serve as a potential predictive biomarker of therapeutic response to anti-PD-1 (FIGS. 6C-6D and Table 1).

Despite the fact that the fraction of CD38+PD-1+CD8+ T-cells in tumor biopsies demonstrated that it can be a strong biomarker for both baseline and post-therapeutic detection of treatment outcome, obtaining biopsies either at baseline or post-therapy may be a major impediment. Accordingly, it was determined whether CD38+PD-1 CD8+ T-cells fraction can also be measured in peripheral blood mononuclear cells (PBMCs) and whether the level of these cells can give early indication for post-therapeutic response status. Therefore, the CD38+ fraction of PD-1+CD8+ T-cells in PBMCs obtained post-therapy from responder and non-responder patients at 3 and 9 weeks from another clinical trial of anti-PD-1 therapy in advanced melanoma patients was tested. The CD38+ fraction of PD-1+CD8+ T-cells showed more than 5% decline at 9 weeks when comparing with 3 weeks in 13 out of 14 responding patients (93%) while most of non-responding patients showed stabilization or increase in the CD38+ fraction in PD-1+CD8+ T-cells (7 of 9 patients (78%); in addition to 9 patients, for 2 patients data is shown at 6 weeks since 9 weeks values were not available) (p≤0.001; AUC: 0.864; PPV: 0.9; NPV: 0.867; sensitivity: 0.818 and specificity: 0.929 when comparing CD38+ fraction of PD-1+CD8+ T-cells that showed more than 5% decline at 9 weeks compared with 3 weeks in responders vs. non-responders) (FIGS. 6E-6F and Table 1). This indicates that the CD38+ fraction of PD-1+CD8+ T-cells in PBMCs merits further investigation as an early pharmacodynamic biomarker for anti-PD-1 therapy.

TABLE 1

Predictive power of biomarkers.

| ROC analysis parameters | Tumor samples | | PBMCs |
|---|---|---|---|
| | Post-therapy (cut-off 4%)# | Pre-therapy (cut-off 10%)^ | Post-therapy (cut-off 5%)* |
| AUC | 0.887 | 0.833 | 0.864 |
| Sensitivity | 1.0 | 0.8 | 0.818 |
| Specificity | 0.75 | 0.667 | 0.929 |
| PPP | 0.913 | 0.727 | 0.9 |
| NPV | 1.0 | 0.75 | 0.867 |
| P-value | 0.0001 | 0.023 | 0.001 |

Comparison of responding vs non-responding patients that had more than 4%# or 10%^CD38+cells in PD1+CD8+ population in the TME.
*For human PBMC data, CD38+ fraction of PD1+CD8+T-cells that showed more than 5% decline at 9 weeks when compared with 3 weeks, were compared between responders and non-responders post-therapy.
AUC: Area Under the Receiver Operating Characteristics (ROC) Curve;
PPP: Positive predictive value;
NPV: Negative predictive value.

Taken together, these results demonstrate that presence of pre-existing high fraction of PD-1+CD38+ cells may be a strong predictor of resistance to anti-PD-1 therapy. Furthermore, the dynamics of the PD-1+CD38+ cells during anti-PD-1 therapy may serve as an early predictor of response to anti-PD-1. In addition, generation of these cells may also be a cause of therapeutic failure after anti-PD-1 therapy.

Together based on the findings, a model was proposed (FIGS. 7A and 7B). Under optimum antigen stimulation, TCR engagement results in formation of a microcluster where signaling molecules are localized strategically for cell activation. Simultaneous PD-1 blockade results in increased phosphorylation of Lck and Zap70 due to reduced SHP2 activity. This in turn enhances the activity of LAT and Akt leading to cell activation, proliferation, effector functions and generation of immune memory (FIG. 7A). However, under suboptimal antigen stimulation, the physical distance between TCR and LAT remains high. Therefore, under these conditions, an absence of activated SHP2 leads to accumulation and eventual degradation of phosphorylated Lck and Zap70 since Zap70 may not be able to hop on to LAT. These events may lead to chromatin remodeling and generation of non-reprogrammability inhibiting cell activation and memory generation (FIG. 7B).

Example 6: Blockade of CD38 with PD-1 Blockade Reduces Numbers of PD1$^+$CD38$^{high}$ CD8$^+$ T-Cells Resulting in Reversal of Anti-PD-1 Resistance Materials and Methods C57/BL6 mice were implanted with TC-1 tumor cells ($7\times10^4$) and apart from untreated control, tumor-bearing mice were treated as: (1) Vaccine; (2) Anti-PD-1+vaccine given simultaneously; (3) Anti-PD-1 given prior (D7) to vaccine+anti-PD-1; and (4) Anti-PD-1+anti-CD38 at D7 followed by vaccine+anti-PD-1. For therapeutic experiments, mice were monitored for tumor growth and survival. For immunological experiments, three days after anti-PD-1+anti-CD38 treatment (D10), or three days after 1$^{st}$ vaccination (D13), mice were euthanized and tumor tissues were harvested for analysis of immune compartment in the TME. Tumor tissues were homogenized using GentleMACS dissociator and the solid tumor homogenization protocol, as suggested by the manufacturer (Miltenyi Biotec, Auburn, CA). Suspended tissue was stained appropriately and FACS analyzed to check the numbers of PD1$^+$CD38$^{high}$ cells in total or antigen-specific CD8$^+$ T-cells.

Results

Figure 8A:
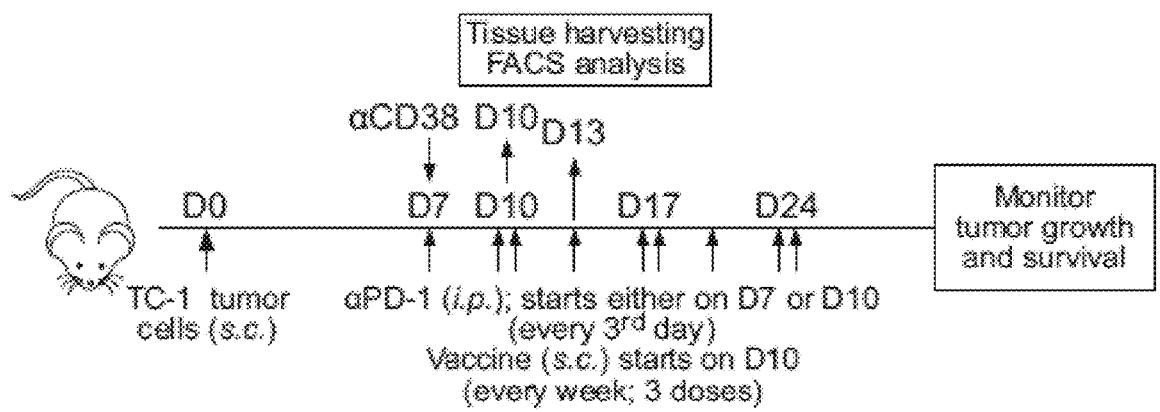
FIG. 8A is a schematic illustration of the experimental design for FIG. 8B-8E. Briefly, mice were injected with TC1 tumor cells at Day 0 (D0) and were administered αCD38 at Day 7 (D7), αPD1 every three days starting at either D7 or Day 10 (D10), and vaccine every week starting at D10.
Figures 8B, 8C, 8D:
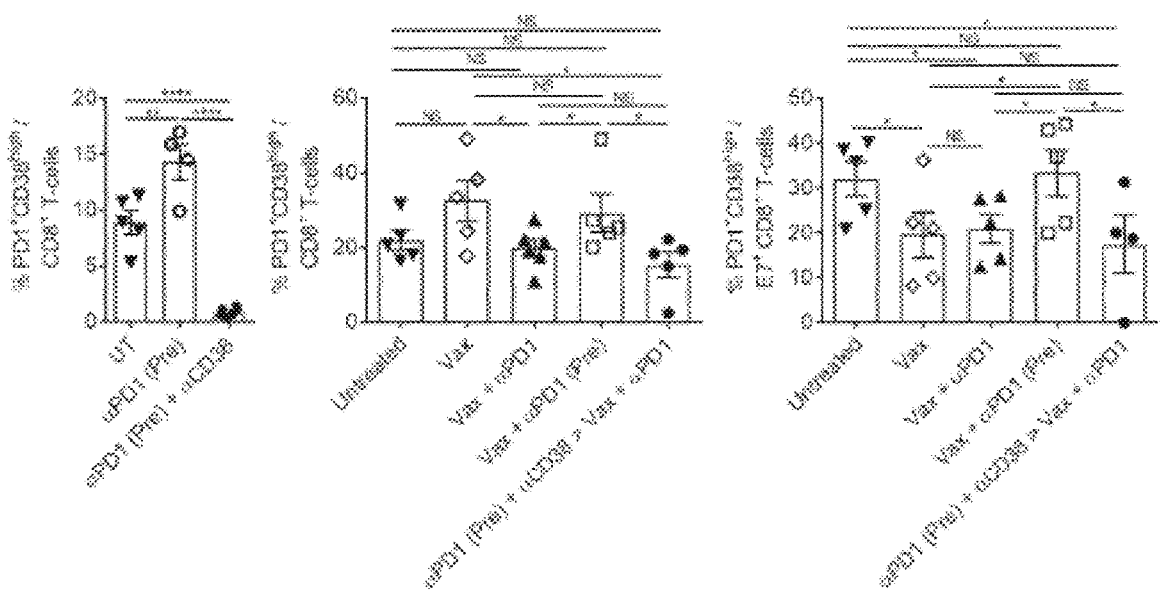
FIG. 8B is a bar graph showing the frequency of PD1⁺CD38$^{high}$ T-cells in total CD8⁺ T-cells at D10 for mice untreated, treated with αPD1, or treated with αPD1+αCD38.
FIG. 8C is a bar graph showing the frequency of PD1⁺CD38$^{high}$ T-cells in total CD8⁺ T-cells at D13 for mice untreated or treated with vaccine (Vax), vaccine+αPD1, vaccine+αPD1 (Pre), or αPD1 (Pre)+αCD38>vaccine+αPD1.
FIG. 8D is a bar graph showing the frequency of PD1⁺CD38$^{high}$ T-cells in antigen-specific CD8⁺ T-cells at D13 for mice untreated or treated with vaccine (Vax), vaccine+αPD1, vaccine+αPD1 (Pre), or αPD1 (Pre)+αCD38>vaccine+αPD1.
Figure 8E:
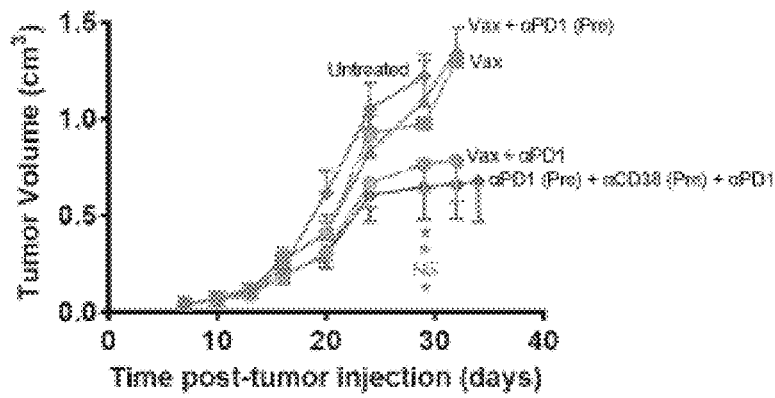
FIGS. 8E-8F are line graphs showing tumor volume (FIG. 8E) and percent survival (FIG. 8F) in TC-1 tumor-bearing mice either untreated or treated with vaccine, vaccine+αPD1, vaccine+αPD1 (pre), or αPD1 (Pre)+αCD38>vaccine+αPD1. Statistical analysis at D29 for tumor volume. $^{NS}$non-significant, *p≤0.05, p≤0.01, *p≤0.001, ****p≤0.0001.
Figure 8F:
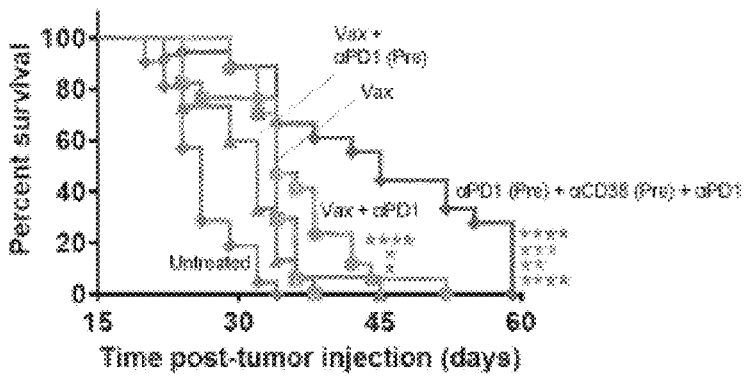

The data show that suboptimal priming induces CD38$^+$ PD-1$^+$CD8$^+$ dysfunctional T-cells while anti-PD-1 increases their numbers (FIG. 5), hence suggesting that the generation of these dysfunctional T-cells may be a mechanism of resistance to anti-PD-1 therapy. In light of these facts, the ability of therapeutic inhibition of CD38$^+$PD-1$^+$CD8$^+$ T-cells to reverse the resistance observed after anti-PD-1 treatment was tested. Anti-CD38 antibody (2.5 mg/kg; i.p.) was administered simultaneously with anti-PD-1 (1 mg/kg) at D7 followed by vaccine and anti-PD-1 in TC-1 tumor-bearing mice (FIG. 8A). Preliminary results showed a significant decrease in the numbers of CD38$^+$PD-1$^+$CD8$^+$ T-cells when anti-CD38 was given with anti-PD-1 (FIG. 8B) and remained low even at D13 (3 days after first vaccination) compared to Vax and Vax+αPD-1 (Pre) groups (FIG. 8C). More significant reduction in the numbers of these cells was found in antigenic-specific T-cells following anti-CD38 treatment (FIG. 8D). Furthermore, prior administration of anti-CD38 with anti-PD-1 completely reversed the resistance to anti-PD-1 therapy and was equally effective to concomitant vaccine+anti-PD-1 treatment (FIG. 8E).

Figure 9A:
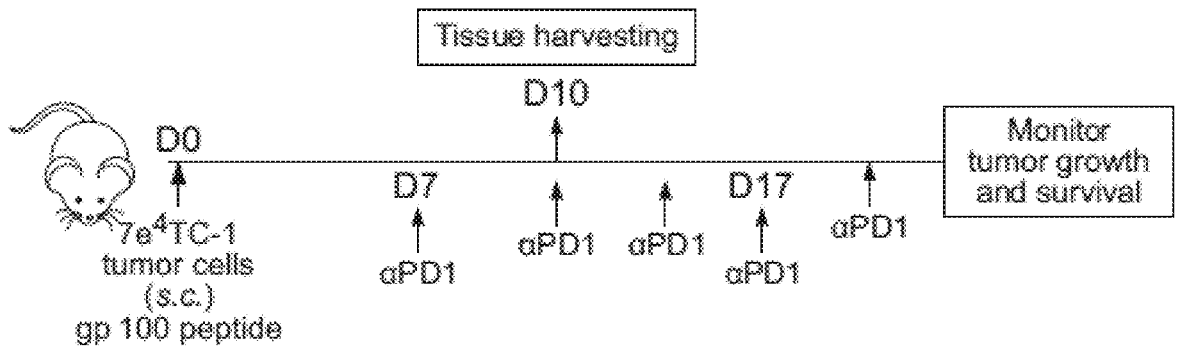
FIG. 9A is a schematic of the schedule of mice treatments.

Example 7: Reversal of Anti-PD-1 Therapy Resistance by CD8$^+$ T-Cell Priming with Irrelevant Antigen Results:

It was found that preventing the suboptimally primed condition by proper CD8; T-cell stimulation at the time of tumor implantation, even with irrelevant antigen, overcomes anti-PD-i resistance. In mice vaccinated with a non-tumor specific peptide (gp100) followed by anti-PD-1 administration (FIG. 9A), tumor growth was significantly reduced with an accompanied increased mouse survival, compared to when anti-PD-1 was inoculated alone (FIGS. 9B-9C). In suboptimally primed TC-1 tumors, anti-PD-1 treatment significantly induced PD1$^+$CD38$^{high}$ T-cells (FIGS. 9D-9E). On the other hand, priming mice with gp100 at the time of tumor inoculation prevented the induction of anti-PD-i-induced dysfunctional cells and also led to increased functionality as shown by enhanced IFNγ production compared to both untreated and anti-PD-1 treated groups (FIGS. 9D-9E).

Example 8: Downregulation of CD38 on PD1$^+$ CD38$^+$CD8$^+$ T-Cells Enhances Cell Activation, Proliferation and Effector Functions Results:

To establish the mechanistic link between CD38 expression and dysfunctionality in CD8$^+$ T-cells, CD38 was knocked down (KD) on PD1$^+$CD38$^+$ T-cells (FIG. 10A). Upon CD38KD (FIG. 10B-10D), these cells regained their ability to proliferate, activate and express effector molecules (FIG. 10E-10G). Therefore, it appears that while expression level of PD-1 determines tumor reactivity (Thommen et al, 2018, Nat Med; Blackburn et al, PNAS 2018), expression of CD38 determines functionality of PD-1 expressing CD8$^+$ T-cells. Thus, these data clearly show that expression of CD38 on PD1$^+$CD8$^+$ T-cells is not a mere marker of cell dysfunctionality but serves a mechanistic role in rendering these CD8$^+$ T-cells dysfunctional.

Example 9: CD38 Depletion Enhances the Anti-Tumor Response of Adoptive T-Cell Therapy (ACT)

Results:

To determine if the PD1$^+$CD38$^+$CD8$^+$ T-cells that were induced after anti-PD-1 treatment of suboptimally primed cells were the reason for poor outcome after anti-PD-1 therapy, and to check if depletion of CD38 can enhance the anti-tumor responses, ACT experiment was performed in Rag$^{-/-}$ mice. Total activated pMel CD8$^+$ T-cell cultures or PD1$^+$CD38$^+$ depleted CD8$^+$ T-cell cultures were transferred into B 16 tumor-bearing Rag$^{-/-}$ mice at day 7 post-tumor implantation (FIG. 11A). Depletion of PD1$^+$CD38$^+$ T-cells enhanced the anti-tumor therapeutic effects of activated CD8$^+$ T-cells (FIGS. 11B-11C), thus confirming that presence of PD1$^+$CD38$^+$ T-cells worsened the anti-tumor effects of activated effector cells and that their depletion enhances the anti-tumor effects of ACT.

Example 10: Anti-CD38 Treatment May Reverse Anti-PID-1 Therapy Resistance

Figure 12A:
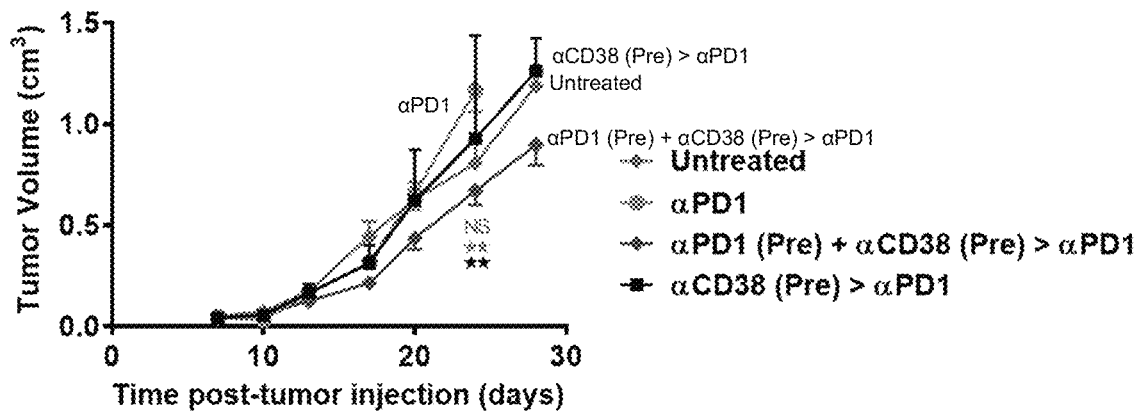
FIGS. 12A-12B are line graphs showing tumor growth (FIG. 12A) and survival (FIG. 12B) in TC-1 tumor bearing mice either untreated or treated with a-PD1, a-PD1 (Pre)+αCD38 (Pre)>αPD1, or αCD38 (Pre)>αPD1 (n=5-8/group; data is representative of two independent experiments). Error bars, SEM. $^{NS}$non-significant, *p≤0.05, p≤0.01, *p≤0.001.
Figure 12B:
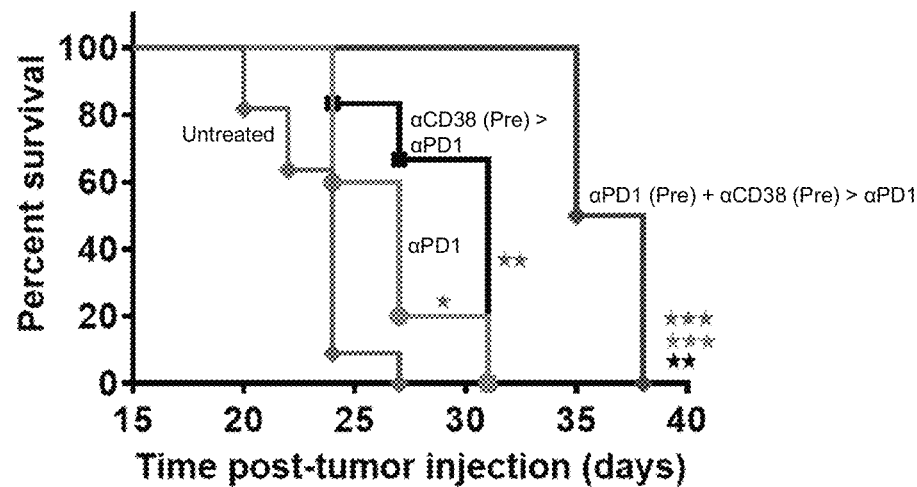

Results:

Anti-PD-1 treatment in suboptimally primed conditions generates PD1$^+$CD38$^+$ dysfunctional cells and expression of CD38 on these cells is detrimental for their functionality. Therefore, it was determined if treatment with anti-CD38 could reverse the resistance to anti-PD1 therapy. Anti-CD38 administration together with anti-PD-1 overcomes anti-PD-1 resistance in TC-1 tumor-bearing mice (FIGS. 12A-12B).

While in the foregoing specification this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

All references cited herein are incorporated by reference in their entirety. The present invention may be embodied in other specific forms without departing from the spirit or essential attributes thereof and, accordingly, reference should be made to the appended claims, rather than to the foregoing specification, as indicating the scope of the invention.

We claim:

1. A method of reducing tumor burden in a subject in need thereof comprising:
   (a) determining the percent of total PD1+CD8+ T cells expressing CD38 in a tumor tissue sample obtained from a subject having had a PD-1/PD-L1 checkpoint inhibitor therapy,
   (b) administering to the subject a composition comprising an effective amount of a compound that promotes or enhances the depletion of CD8$^+$CD8$^+$ T cells, CD8$^+$PD-1$^+$ T cells, or both, or decreases the activity of CD38 on T cells in the subject if more than 4% of the total PD1+CD8+ T cells express CD38,
   (c) administering to the subject a cancer vaccine in an amount effective to prime T cells, and
   (d) administering to the subject, simultaneously with (b) and/or (c), the same or a different PD-1/PD-L1 checkpoint inhibitor therapy in an amount effective to reduce tumor burden.

2. The method of claim 1, wherein the composition comprising an effective amount of a compound that promotes or enhances the depletion of CD38$^+$CD8$^+$ T cells, CD38$^+$PD-1$^+$ T cells, or both, or decreases the activity of CD38 on T cells in the subject is anti-CD38 antibody.

3. The method of claim 1, wherein the composition comprising an effective amount of a compound that promotes or enhances the depletion of CD38$^+$CD8$^+$ T cells, CD38$^+$PD-1$^+$ T cells, or both, or decreases the activity of CD38 on T cells in the subject is a bispecific anti-CD38/anti-CD8 antibody.

4. The method of claim 1, wherein the composition comprising an effective amount of a compound that promotes or enhances the depletion of CD38$^+$CD8$^+$ T cells, CD38$^+$PD-1$^+$ T cells, or both, or decreases the activity of CD38 on T cells in the subject's tumor microenvironment is a bispecific anti-CD38/anti-PD-1 antibody.

5. The method of claim 1, wherein the composition comprising an effective amount of a compound that promotes or enhances the depletion of CD38$^+$CD8$^+$ T cells, CD38$^+$PD-1$^+$ T cells, or both, or decreases the activity of CD38 on T cells in the subject is a CD38 small molecule inhibitor.

6. The method of claim 1, wherein the PD-1/PD-L1 checkpoint inhibitor therapy comprises an anti-PD-1 antibody, an anti-PD-L1 antibody, or both.

7. The method of claim 1, wherein the PD-1/PD-L1 checkpoint inhibitor therapy is selected from the group consisting of pembrolizumab, nivolumab, atezolizumab, avelumab, durvalumab, or a combination thereof.

8. A method of increasing the efficacy of a PD-1/PD-L1 checkpoint inhibitor therapy in a subject in need thereof comprising:

(a) determining the percent of CD38+ cells out of total PD1+CD8+ T cells in a tumor tissue sample obtained from the subject prior to the PD-1/PD-L1 checkpoint inhibitor therapy, (b) administering to the subject a pharmaceutical composition comprising an effective amount of a compound that promotes or enhances the depletion of $CD38^+$ $CD8^+$ T cells, $CD38^+PD-1^+$ T cells, or both, or decreases the activity of CD38 on T cells in the subject, if the subject has 5% or more CD38+ cells out of total PD1+CD8+ T cells in the tumor tissue, and (c) subsequently and/or concurrently with (b) administering to the subject the PD-1/PD-L1 checkpoint inhibitor therapy in an amount effective to reduce tumor burden.

9. The method of claim 8, wherein the compound that promotes or enhances the depletion of CD38+ T cells is a bispecific anti-CD38/anti-CD8 antibody, a bispecific anti-CD38/anti-PD-1 antibody, or a monoclonal anti-CD38 antibody.

10. The method of claim 8, wherein the PD-1/PD-L1 checkpoint inhibitor therapy comprises an anti-PD-1 antibody, an anti-PD-L1 antibody, or both.

11. A method of detecting and treating resistance to a PD-1/PD-L1 checkpoint inhibitor therapy in a subject in need thereof, the method comprising:

(a) determining the percent of CD38+ cells out of total PD1+CD8+ T cells in the peripheral blood mononuclear cells (PBMCs) obtained from a subject at an early and a late time-points after the start of the PD-1/PD-L1 checkpoint inhibitor therapy, (b) diagnosing the subject as resistant to the PD-1/PD-L1 checkpoint inhibitor therapy if the percent of the total PD1+CD8+ T cells expressing CD38+ from the PMBC is stabilized or increased at the later time-point compared to that of the earlier time-point, or the decline in the percent of CD38+ cells out of total PD1+CD8+ T cells in PBMCs from the earlier time point is 5% or less compared to that of the later time-point, (c) if the subject is diagnosed as resistant to the PD-1/PD-L1 checkpoint inhibitor therapy administering to the subject a composition comprising an effective amount of a compound that promotes or enhances the depletion of $CD38^+CD8^+$ T cells, $CD38^+PD-1^+$ T cells, or both; or decreases the activity of CD38 on T cells in the subject, and (d) concurrently and/or subsequently administering the PD-1/PD-L1 checkpoint inhibitor therapy to the subject.

12. The method of claim 11, wherein the early time point is about 3 weeks to about 6 weeks after the start of the PD-1/PD-L1 checkpoint inhibitor therapy, and wherein the late time point is about 6 weeks to about 9 weeks after the start of the PD-1/PD-L1 checkpoint inhibitor therapy.

13. The method of claim 11, further comprising administering to the subject a second active agent that is selected from the group consisting of anti-CTLA4 therapy, chemotherapeutic agents, cytokines, chemokines, vaccines, and radiation therapy.

14. The method of claim 11, wherein determining the percent of CD38+cells of total PD1+CD8+ T cells in the PBMC comprises the method of flow cytometry.

15. The method of claim 8, wherein more than 10% of total PD1+CD8+ T cells from the tumor tissue express CD38+.

16. The method of claim 8, wherein more than 25% of total PD1+CD8+ T cells from the tumor tissue express CD38+.

17. The method of claim 8, wherein the PD-1/PD-L1 checkpoint inhibitor therapy comprises an anti-PD-1 antibody, an anti-PD-L1 antibody, or both.

18. The method of claim 8, further comprising administering to the subject a cancer vaccine simultaneously with the PD-1/PD-L1 checkpoint inhibitor therapy in an amount effective to reduce tumor burden.

19. The method of claim 8, wherein the tumor tissue is one obtained from tumor biopsy.

20. The method of claim 11, wherein the compound that promotes or enhances the depletion of CD38+ T cells is a bispecific anti-CD38/anti-CD8 antibody, a bispecific anti-CD38/anti-PD-1 antibody, or a monoclonal anti-CD38 antibody.

21. The method of claim 1, wherein (b) is repeated until the total percent of PD1+CD8+ T cells expressing CD38 in the tumor is reduced, optionally to 4% or less.

22. The method of claim 8, wherein (c) is repeated until the total percent of PD1+CD8+ T cells expressing CD38 in the tumor is reduced, optionally to less than 5%.

23. The method of claim 11, wherein (c) is repeated until the decline in the percent of CD38+ cells out of total PD1+CD8+ T cells in PBMCs from the earlier time point is reduced, optionally to more than 5% compared to that of the later time-point.

* * * * *

SEQUENCE LISTING

<160> NUMBER OF SEQ ID NOS: 23

<210> SEQ ID NO 1
<211> LENGTH: 300
<212> TYPE: PRT
<213> ORGANISM: Homo sapiens

<400> SEQUENCE: 1

Met Ala Asn Cys Glu Phe Ser Pro Val Ser Gly Asp Lys Pro Cys Cys
1               5                   10                  15

Arg Leu Ser Arg Arg Ala Gln Leu Cys Leu Gly Val Ser Ile Leu Val
            20                  25                  30

Leu Ile Leu Val Val Val Leu Ala Val Val Pro Arg Trp Arg Gln
        35                  40                  45

Gln Trp Ser Gly Pro Gly Thr Thr Lys Arg Phe Pro Glu Thr Val Leu
50                  55                  60

Ala Arg Cys Val Lys Tyr Thr Glu Ile His Pro Glu Met Arg His Val
65                  70                  75                  80

Asp Cys Gln Ser Val Trp Asp Ala Phe Lys Gly Ala Phe Ile Ser Lys
                85                  90                  95

His Pro Cys Asn Ile Thr Glu Glu Asp Tyr Gln Pro Leu Met Lys Leu
            100                 105                 110

Gly Thr Gln Thr Val Pro Cys Asn Lys Ile Leu Leu Trp Ser Arg Ile
        115                 120                 125

Lys Asp Leu Ala His Gln Phe Thr Gln Val Gln Arg Asp Met Phe Thr
130                 135                 140

Leu Glu Asp Thr Leu Leu Gly Tyr Leu Ala Asp Asp Leu Thr Trp Cys
145                 150                 155                 160

Gly Glu Phe Asn Thr Ser Lys Ile Asn Tyr Gln Ser Cys Pro Asp Trp
                165                 170                 175

Arg Lys Asp Cys Ser Asn Asn Pro Val Ser Val Phe Trp Lys Thr Val
            180                 185                 190

Ser Arg Arg Phe Ala Glu Ala Ala Cys Asp Val Val His Val Met Leu
        195                 200                 205

Asn Gly Ser Arg Ser Lys Ile Phe Asp Lys Asn Ser Thr Phe Gly Ser
210                 215                 220

Val Glu Val His Asn Leu Gln Pro Glu Lys Val Gln Thr Leu Glu Ala
225                 230                 235                 240

Trp Val Ile His Gly Gly Arg Glu Asp Ser Arg Asp Leu Cys Gln Asp
                245                 250                 255

Pro Thr Ile Lys Glu Leu Glu Ser Ile Ile Ser Lys Arg Asn Ile Gln
            260                 265                 270

Phe Ser Cys Lys Asn Ile Tyr Arg Pro Asp Lys Phe Leu Gln Cys Val
        275                 280                 285

Lys Asn Pro Glu Asp Ser Ser Cys Thr Ser Glu Ile
            290                 295                 300

<210> SEQ ID NO 2
<211> LENGTH: 258
<212> TYPE: PRT
<213> ORGANISM: Homo sapiens

<400> SEQUENCE: 2

Val Pro Arg Trp Arg Gln Gln Trp Ser Gly Pro Gly Thr Thr Lys Arg
1               5                   10                  15

Phe Pro Glu Thr Val Leu Ala Arg Cys Val Lys Tyr Thr Glu Ile His

```
                  20                  25                  30
Pro Glu Met Arg His Val Asp Cys Gln Ser Val Trp Asp Ala Phe Lys
            35                  40                  45

Gly Ala Phe Ile Ser Lys His Pro Cys Asn Ile Thr Glu Glu Asp Tyr
        50                  55                  60

Gln Pro Leu Met Lys Leu Gly Thr Gln Thr Val Pro Cys Asn Lys Ile
65                  70                  75                  80

Leu Leu Trp Ser Arg Ile Lys Asp Leu Ala His Gln Phe Thr Gln Val
                85                  90                  95

Gln Arg Asp Met Phe Thr Leu Glu Asp Thr Leu Leu Gly Tyr Leu Ala
            100                 105                 110

Asp Asp Leu Thr Trp Cys Gly Glu Phe Asn Thr Ser Lys Ile Asn Tyr
        115                 120                 125

Gln Ser Cys Pro Asp Trp Arg Lys Asp Cys Ser Asn Asn Pro Val Ser
        130                 135                 140

Val Phe Trp Lys Thr Val Ser Arg Arg Phe Ala Glu Ala Ala Cys Asp
145                 150                 155                 160

Val Val His Val Met Leu Asn Gly Ser Arg Ser Lys Ile Phe Asp Lys
                165                 170                 175

Asn Ser Thr Phe Gly Ser Val Glu Val His Asn Leu Gln Pro Glu Lys
            180                 185                 190

Val Gln Thr Leu Glu Ala Trp Val Ile His Gly Gly Arg Glu Asp Ser
        195                 200                 205

Arg Asp Leu Cys Gln Asp Pro Thr Ile Lys Glu Leu Glu Ser Ile Ile
    210                 215                 220

Ser Lys Arg Asn Ile Gln Phe Ser Cys Lys Asn Ile Tyr Arg Pro Asp
225                 230                 235                 240

Lys Phe Leu Gln Cys Val Lys Asn Pro Glu Asp Ser Ser Cys Thr Ser
                245                 250                 255

Glu Ile

<210> SEQ ID NO 3
<211> LENGTH: 122
<212> TYPE: PRT
<213> ORGANISM: Homo sapiens

<400> SEQUENCE: 3

Met Ala Asn Cys Glu Phe Ser Pro Val Ser Gly Asp Lys Pro Cys Cys
1               5                   10                  15

Arg Leu Ser Arg Arg Ala Gln Leu Cys Leu Gly Val Ser Ile Leu Val
            20                  25                  30

Leu Ile Leu Val Val Val Leu Ala Val Val Val Pro Arg Trp Arg Gln
        35                  40                  45

Gln Trp Ser Gly Pro Gly Thr Thr Lys Arg Phe Pro Glu Thr Val Leu
    50                  55                  60

Ala Arg Cys Val Lys Tyr Thr Glu Ile His Pro Glu Met Arg His Val
65                  70                  75                  80

Asp Cys Gln Ser Val Trp Asp Ala Phe Lys Gly Ala Phe Ile Ser Lys
                85                  90                  95

His Pro Cys Asn Ile Thr Glu Glu Asp Tyr Gln Pro Leu Met Lys Leu
            100                 105                 110

Gly Thr Gln Thr Val Pro Cys Asn Lys Lys
        115                 120
```

-continued

```
<210> SEQ ID NO 4
<211> LENGTH: 738
<212> TYPE: PRT
<213> ORGANISM: Homo sapiens

<400> SEQUENCE: 4

Met Gln Pro Arg Trp Ala Gln Gly Ala Thr Met Trp Leu Gly Val Leu
1               5                   10                  15

Leu Thr Leu Leu Leu Cys Ser Ser Leu Glu Gly Gln Glu Asn Ser Phe
            20                  25                  30

Thr Ile Asn Ser Val Asp Met Lys Ser Leu Pro Asp Trp Thr Val Gln
        35                  40                  45

Asn Gly Lys Asn Leu Thr Leu Gln Cys Phe Ala Asp Val Ser Thr Thr
    50                  55                  60

Ser His Val Lys Pro Gln His Gln Met Leu Phe Tyr Lys Asp Asp Val
65                  70                  75                  80

Leu Phe Tyr Asn Ile Ser Ser Met Lys Ser Thr Glu Ser Tyr Phe Ile
                85                  90                  95

Pro Glu Val Arg Ile Tyr Asp Ser Gly Thr Tyr Lys Cys Thr Val Ile
            100                 105                 110

Val Asn Asn Lys Glu Lys Thr Thr Ala Glu Tyr Gln Val Leu Val Glu
        115                 120                 125

Gly Val Pro Ser Pro Arg Val Thr Leu Asp Lys Lys Glu Ala Ile Gln
    130                 135                 140

Gly Gly Ile Val Arg Val Asn Cys Ser Val Pro Glu Glu Lys Ala Pro
145                 150                 155                 160

Ile His Phe Thr Ile Glu Lys Leu Glu Leu Asn Glu Lys Met Val Lys
                165                 170                 175

Leu Lys Arg Glu Lys Asn Ser Arg Asp Gln Asn Phe Val Ile Leu Glu
            180                 185                 190

Phe Pro Val Glu Glu Gln Asp Arg Val Leu Ser Phe Arg Cys Gln Ala
        195                 200                 205

Arg Ile Ile Ser Gly Ile His Met Gln Thr Ser Glu Ser Thr Lys Ser
    210                 215                 220

Glu Leu Val Thr Val Thr Glu Ser Phe Ser Thr Pro Lys Phe His Ile
225                 230                 235                 240

Ser Pro Thr Gly Met Ile Met Glu Gly Ala Gln Leu His Ile Lys Cys
                245                 250                 255

Thr Ile Gln Val Thr His Leu Ala Gln Glu Phe Pro Glu Ile Ile Ile
            260                 265                 270

Gln Lys Asp Lys Ala Ile Val Ala His Asn Arg His Gly Asn Lys Ala
        275                 280                 285

Val Tyr Ser Val Met Ala Met Val Glu His Ser Gly Asn Tyr Thr Cys
    290                 295                 300

Lys Val Glu Ser Ser Arg Ile Ser Lys Val Ser Ser Ile Val Val Asn
305                 310                 315                 320

Ile Thr Glu Leu Phe Ser Lys Pro Glu Leu Glu Ser Ser Phe Thr His
                325                 330                 335

Leu Asp Gln Gly Glu Arg Leu Asn Leu Ser Cys Ser Ile Pro Gly Ala
            340                 345                 350

Pro Pro Ala Asn Phe Thr Ile Gln Lys Glu Asp Thr Ile Val Ser Gln
        355                 360                 365

Thr Gln Asp Phe Thr Lys Ile Ala Ser Lys Ser Asp Ser Gly Thr Tyr
    370                 375                 380
```

```
Ile Cys Thr Ala Gly Ile Asp Lys Val Val Lys Ser Asn Thr Val
385                 390                 395                 400

Gln Ile Val Val Cys Glu Met Leu Ser Gln Pro Arg Ile Ser Tyr Asp
            405                 410                 415

Ala Gln Phe Glu Val Ile Lys Gly Gln Thr Ile Glu Val Arg Cys Glu
            420                 425                 430

Ser Ile Ser Gly Thr Leu Pro Ile Ser Tyr Gln Leu Leu Lys Thr Ser
            435                 440                 445

Lys Val Leu Glu Asn Ser Thr Lys Asn Ser Asn Asp Pro Ala Val Phe
450                 455                 460

Lys Asp Asn Pro Thr Glu Asp Val Glu Tyr Gln Cys Val Ala Asp Asn
465                 470                 475                 480

Cys His Ser His Ala Lys Met Leu Ser Glu Val Leu Arg Val Lys Val
            485                 490                 495

Ile Ala Pro Val Asp Glu Val Gln Ile Ser Ile Leu Ser Ser Lys Val
            500                 505                 510

Val Glu Ser Gly Glu Asp Ile Val Leu Gln Cys Ala Val Asn Glu Gly
            515                 520                 525

Ser Gly Pro Ile Thr Tyr Lys Phe Tyr Arg Glu Lys Glu Gly Lys Pro
            530                 535                 540

Phe Tyr Gln Met Thr Ser Asn Ala Thr Gln Ala Phe Trp Thr Lys Gln
545                 550                 555                 560

Lys Ala Ser Lys Glu Gln Gly Glu Tyr Tyr Cys Thr Ala Phe Asn
                565                 570                 575

Arg Ala Asn His Ala Ser Ser Val Pro Arg Ser Lys Ile Leu Thr Val
            580                 585                 590

Arg Val Ile Leu Ala Pro Trp Lys Lys Gly Leu Ile Ala Val Val Ile
            595                 600                 605

Ile Gly Val Ile Ile Ala Leu Leu Ile Ile Ala Ala Lys Cys Tyr Phe
610                 615                 620

Leu Arg Lys Ala Lys Ala Lys Gln Met Pro Val Glu Met Ser Arg Pro
625                 630                 635                 640

Ala Val Pro Leu Leu Asn Ser Asn Asn Glu Lys Met Ser Asp Pro Asn
            645                 650                 655

Met Glu Ala Asn Ser His Tyr Gly His Asn Asp Asp Val Arg Asn His
            660                 665                 670

Ala Met Lys Pro Ile Asn Asp Asn Lys Glu Pro Leu Asn Ser Asp Val
            675                 680                 685

Gln Tyr Thr Glu Val Gln Val Ser Ser Ala Glu Ser His Lys Asp Leu
            690                 695                 700

Gly Lys Lys Asp Thr Glu Thr Val Tyr Ser Glu Val Arg Lys Ala Val
705                 710                 715                 720

Pro Asp Ala Val Glu Ser Arg Tyr Ser Arg Thr Glu Gly Ser Leu Asp
                725                 730                 735

Gly Thr

<210> SEQ ID NO 5
<211> LENGTH: 235
<212> TYPE: PRT
<213> ORGANISM: Homo sapiens

<400> SEQUENCE: 5

Met Ala Leu Pro Val Thr Ala Leu Leu Leu Pro Leu Ala Leu Leu Leu
1               5                   10                  15
```

His Ala Ala Arg Pro Ser Gln Phe Arg Val Ser Pro Leu Asp Arg Thr
            20                  25                  30

Trp Asn Leu Gly Glu Thr Val Glu Leu Lys Cys Gln Val Leu Leu Ser
        35                  40                  45

Asn Pro Thr Ser Gly Cys Ser Trp Leu Phe Gln Pro Arg Gly Ala Ala
    50                  55                  60

Ala Ser Pro Thr Phe Leu Leu Tyr Leu Ser Gln Asn Lys Pro Lys Ala
65                  70                  75                  80

Ala Glu Gly Leu Asp Thr Gln Arg Phe Ser Gly Lys Arg Leu Gly Asp
                85                  90                  95

Thr Phe Val Leu Thr Leu Ser Asp Phe Arg Arg Glu Asn Glu Gly Tyr
            100                 105                 110

Tyr Phe Cys Ser Ala Leu Ser Asn Ser Ile Met Tyr Phe Ser His Phe
        115                 120                 125

Val Pro Val Phe Leu Pro Ala Lys Pro Thr Thr Thr Pro Ala Pro Arg
    130                 135                 140

Pro Pro Thr Pro Ala Pro Thr Ile Ala Ser Gln Pro Leu Ser Leu Arg
145                 150                 155                 160

Pro Glu Ala Cys Arg Pro Ala Ala Gly Gly Ala Val His Thr Arg Gly
                165                 170                 175

Leu Asp Phe Ala Cys Asp Ile Tyr Ile Trp Ala Pro Leu Ala Gly Thr
            180                 185                 190

Cys Gly Val Leu Leu Leu Ser Leu Val Ile Thr Leu Tyr Cys Asn His
        195                 200                 205

Arg Asn Arg Arg Arg Val Cys Lys Cys Pro Arg Pro Val Val Lys Ser
    210                 215                 220

Gly Asp Lys Pro Ser Leu Ser Ala Arg Tyr Val
225                 230                 235

<210> SEQ ID NO 6
<211> LENGTH: 161
<212> TYPE: PRT
<213> ORGANISM: Homo sapiens

<400> SEQUENCE: 6

Ser Gln Phe Arg Val Ser Pro Leu Asp Arg Thr Trp Asn Leu Gly Glu
1               5                   10                  15

Thr Val Glu Leu Lys Cys Gln Val Leu Leu Ser Asn Pro Thr Ser Gly
            20                  25                  30

Cys Ser Trp Leu Phe Gln Pro Arg Gly Ala Ala Ala Ser Pro Thr Phe
        35                  40                  45

Leu Leu Tyr Leu Ser Gln Asn Lys Pro Lys Ala Ala Glu Gly Leu Asp
    50                  55                  60

Thr Gln Arg Phe Ser Gly Lys Arg Leu Gly Asp Thr Phe Val Leu Thr
65                  70                  75                  80

Leu Ser Asp Phe Arg Arg Glu Asn Glu Gly Tyr Tyr Phe Cys Ser Ala
                85                  90                  95

Leu Ser Asn Ser Ile Met Tyr Phe Ser His Phe Val Pro Val Phe Leu
            100                 105                 110

Pro Ala Lys Pro Thr Thr Thr Pro Ala Pro Arg Pro Pro Thr Pro Ala
        115                 120                 125

Pro Thr Ile Ala Ser Gln Pro Leu Ser Leu Arg Pro Glu Ala Cys Arg
    130                 135                 140

Pro Ala Ala Gly Gly Ala Val His Thr Arg Gly Leu Asp Phe Ala Cys
145                 150                 155                 160

Asp

<210> SEQ ID NO 7
<211> LENGTH: 198
<212> TYPE: PRT
<213> ORGANISM: Homo sapiens

<400> SEQUENCE: 7

Met Ala Leu Pro Val Thr Ala Leu Leu Pro Leu Ala Leu Leu Leu
1               5                   10                  15

His Ala Ala Arg Pro Ser Gln Phe Arg Val Ser Pro Leu Asp Arg Thr
            20                  25                  30

Trp Asn Leu Gly Glu Thr Val Glu Leu Lys Cys Gln Val Leu Leu Ser
            35                  40                  45

Asn Pro Thr Ser Gly Cys Ser Trp Leu Phe Gln Pro Arg Gly Ala Ala
50                  55                  60

Ala Ser Pro Thr Phe Leu Leu Tyr Leu Ser Gln Asn Lys Pro Lys Ala
65                  70                  75                  80

Ala Glu Gly Leu Asp Thr Gln Arg Phe Ser Gly Lys Arg Leu Gly Asp
                85                  90                  95

Thr Phe Val Leu Thr Leu Ser Asp Phe Arg Arg Glu Asn Glu Gly Tyr
            100                 105                 110

Tyr Phe Cys Ser Ala Leu Ser Asn Ser Ile Met Tyr Phe Ser His Phe
        115                 120                 125

Val Pro Val Phe Leu Pro Ala Lys Pro Thr Thr Thr Pro Ala Pro Arg
    130                 135                 140

Pro Pro Thr Pro Ala Pro Thr Ile Ala Ser Gln Pro Leu Ser Leu Arg
145                 150                 155                 160

Pro Glu Ala Cys Arg Pro Ala Ala Gly Gly Ala Gly Asn Arg Arg Arg
                165                 170                 175

Val Cys Lys Cys Pro Arg Pro Val Val Lys Ser Gly Asp Lys Pro Ser
            180                 185                 190

Leu Ser Ala Arg Tyr Val
        195

<210> SEQ ID NO 8
<211> LENGTH: 276
<212> TYPE: PRT
<213> ORGANISM: Homo sapiens

<400> SEQUENCE: 8

Met Arg Asn Gln Ala Pro Gly Arg Pro Lys Gly Ala Thr Phe Pro Pro
1               5                   10                  15

Arg Arg Pro Thr Gly Ser Arg Ala Pro Pro Leu Ala Pro Glu Leu Arg
            20                  25                  30

Ala Lys Gln Arg Pro Gly Glu Arg Val Met Ala Leu Pro Val Thr Ala
            35                  40                  45

Leu Leu Leu Pro Leu Ala Leu Leu Leu His Ala Ala Arg Pro Ser Gln
50                  55                  60

Phe Arg Val Ser Pro Leu Asp Arg Thr Trp Asn Leu Gly Glu Thr Val
65                  70                  75                  80

Glu Leu Lys Cys Gln Val Leu Leu Ser Asn Pro Thr Ser Gly Cys Ser
                85                  90                  95

Trp Leu Phe Gln Pro Arg Gly Ala Ala Ala Ser Pro Thr Phe Leu Leu
            100                 105                 110

```
Tyr Leu Ser Gln Asn Lys Pro Lys Ala Ala Glu Gly Leu Asp Thr Gln
            115                 120                 125

Arg Phe Ser Gly Lys Arg Leu Gly Asp Thr Phe Val Leu Thr Leu Ser
        130                 135                 140

Asp Phe Arg Arg Glu Asn Glu Gly Tyr Tyr Phe Cys Ser Ala Leu Ser
145                 150                 155                 160

Asn Ser Ile Met Tyr Phe Ser His Phe Val Pro Val Phe Leu Pro Ala
                165                 170                 175

Lys Pro Thr Thr Thr Pro Ala Pro Arg Pro Pro Thr Pro Ala Pro Thr
            180                 185                 190

Ile Ala Ser Gln Pro Leu Ser Leu Arg Pro Glu Ala Cys Arg Pro Ala
        195                 200                 205

Ala Gly Gly Ala Val His Thr Arg Gly Leu Asp Phe Ala Cys Asp Ile
    210                 215                 220

Tyr Ile Trp Ala Pro Leu Ala Gly Thr Cys Gly Val Leu Leu Leu Ser
225                 230                 235                 240

Leu Val Ile Thr Leu Tyr Cys Asn His Arg Asn Arg Arg Arg Val Cys
                245                 250                 255

Lys Cys Pro Arg Pro Val Val Lys Ser Gly Asp Lys Pro Ser Leu Ser
            260                 265                 270

Ala Arg Tyr Val
    275

<210> SEQ ID NO 9
<211> LENGTH: 210
<212> TYPE: PRT
<213> ORGANISM: Homo sapiens

<400> SEQUENCE: 9

Met Arg Pro Arg Leu Trp Leu Leu Leu Ala Ala Gln Leu Thr Val Leu
1               5                   10                  15

His Gly Asn Ser Val Leu Gln Gln Thr Pro Ala Tyr Ile Lys Val Gln
            20                  25                  30

Thr Asn Lys Met Val Met Leu Ser Cys Glu Ala Lys Ile Ser Leu Ser
        35                  40                  45

Asn Met Arg Ile Tyr Trp Leu Arg Gln Arg Gln Ala Pro Ser Ser Asp
    50                  55                  60

Ser His His Glu Phe Leu Ala Leu Trp Asp Ser Ala Lys Gly Thr Ile
65                  70                  75                  80

His Gly Glu Glu Val Glu Gln Glu Lys Ile Ala Val Phe Arg Asp Ala
                85                  90                  95

Ser Arg Phe Ile Leu Asn Leu Thr Ser Val Lys Pro Glu Asp Ser Gly
            100                 105                 110

Ile Tyr Phe Cys Met Ile Val Gly Ser Pro Glu Leu Thr Phe Gly Lys
        115                 120                 125

Gly Thr Gln Leu Ser Val Val Asp Phe Leu Pro Thr Thr Ala Gln Pro
    130                 135                 140

Thr Lys Lys Ser Thr Leu Lys Lys Arg Val Cys Arg Leu Pro Arg Pro
145                 150                 155                 160

Glu Thr Gln Lys Gly Pro Leu Cys Ser Pro Ile Thr Leu Gly Leu Leu
                165                 170                 175

Val Ala Gly Val Leu Val Leu Leu Val Ser Leu Gly Val Ala Ile His
            180                 185                 190

Leu Cys Cys Arg Arg Arg Arg Ala Arg Leu Arg Phe Met Lys Gln Phe
        195                 200                 205
```

Tyr Lys
    210

<210> SEQ ID NO 10
<211> LENGTH: 149
<212> TYPE: PRT
<213> ORGANISM: Homo sapiens

<400> SEQUENCE: 10

Leu Gln Gln Thr Pro Ala Tyr Ile Lys Val Gln Thr Asn Lys Met Val
1               5                   10                  15

Met Leu Ser Cys Glu Ala Lys Ile Ser Leu Ser Asn Met Arg Ile Tyr
            20                  25                  30

Trp Leu Arg Gln Arg Gln Ala Pro Ser Ser Asp Ser His His Glu Phe
        35                  40                  45

Leu Ala Leu Trp Asp Ser Ala Lys Gly Thr Ile His Gly Glu Val
    50                  55                  60

Glu Gln Glu Lys Ile Ala Val Phe Arg Asp Ala Ser Arg Phe Ile Leu
65                  70                  75                  80

Asn Leu Thr Ser Val Lys Pro Glu Asp Ser Gly Ile Tyr Phe Cys Met
                85                  90                  95

Ile Val Gly Ser Pro Glu Leu Thr Phe Gly Lys Gly Thr Gln Leu Ser
            100                 105                 110

Val Val Asp Phe Leu Pro Thr Thr Ala Gln Pro Thr Lys Lys Ser Thr
        115                 120                 125

Leu Lys Lys Arg Val Cys Arg Leu Pro Arg Pro Glu Thr Gln Lys Gly
    130                 135                 140

Pro Leu Cys Ser Pro
145

<210> SEQ ID NO 11
<211> LENGTH: 221
<212> TYPE: PRT
<213> ORGANISM: Homo sapiens

<400> SEQUENCE: 11

Met Arg Pro Arg Leu Trp Leu Leu Leu Ala Ala Gln Leu Thr Val Leu
1               5                   10                  15

His Gly Asn Ser Val Leu Gln Gln Thr Pro Ala Tyr Ile Lys Val Gln
            20                  25                  30

Thr Asn Lys Met Val Met Leu Ser Cys Glu Ala Lys Ile Ser Leu Ser
        35                  40                  45

Asn Met Arg Ile Tyr Trp Leu Arg Gln Arg Gln Ala Pro Ser Ser Asp
    50                  55                  60

Ser His His Glu Phe Leu Ala Leu Trp Asp Ser Ala Lys Gly Thr Ile
65                  70                  75                  80

His Gly Glu Glu Val Glu Gln Glu Lys Ile Ala Val Phe Arg Asp Ala
                85                  90                  95

Ser Arg Phe Ile Leu Asn Leu Thr Ser Val Lys Pro Glu Asp Ser Gly
            100                 105                 110

Ile Tyr Phe Cys Met Ile Val Gly Ser Pro Glu Leu Thr Phe Gly Lys
        115                 120                 125

Gly Thr Gln Leu Ser Val Val Asp Phe Leu Pro Thr Thr Ala Gln Pro
    130                 135                 140

Thr Lys Lys Ser Thr Leu Lys Lys Arg Val Cys Arg Leu Pro Arg Pro
145                 150                 155                 160

Glu Thr Gln Lys Gly Pro Leu Cys Ser Pro Ile Thr Leu Gly Leu Leu
165                 170                 175

Val Ala Gly Val Leu Val Leu Val Ser Leu Gly Val Ala Ile His
        180                 185                 190

Leu Cys Cys Arg Arg Arg Arg Ala Arg Leu Arg Phe Met Lys Gln Leu
        195                 200                 205

Arg Leu His Pro Leu Glu Lys Cys Ser Arg Met Asp Tyr
210                 215                 220

<210> SEQ ID NO 12
<211> LENGTH: 213
<212> TYPE: PRT
<213> ORGANISM: Homo sapiens

<400> SEQUENCE: 12

Met Arg Pro Arg Leu Trp Leu Leu Leu Ala Ala Gln Leu Thr Val Leu
1               5                   10                  15

His Gly Asn Ser Val Leu Gln Gln Thr Pro Ala Tyr Ile Lys Val Gln
            20                  25                  30

Thr Asn Lys Met Val Met Leu Ser Cys Glu Ala Lys Ile Ser Leu Ser
        35                  40                  45

Asn Met Arg Ile Tyr Trp Leu Arg Gln Arg Gln Ala Pro Ser Ser Asp
    50                  55                  60

Ser His His Glu Phe Leu Ala Leu Trp Asp Ser Ala Lys Gly Thr Ile
65                  70                  75                  80

His Gly Glu Glu Val Glu Gln Glu Lys Ile Ala Val Phe Arg Asp Ala
                85                  90                  95

Ser Arg Phe Ile Leu Asn Leu Thr Ser Val Lys Pro Glu Asp Ser Gly
            100                 105                 110

Ile Tyr Phe Cys Met Ile Val Gly Ser Pro Glu Leu Thr Phe Gly Lys
        115                 120                 125

Gly Thr Gln Leu Ser Val Val Asp Phe Leu Pro Thr Thr Ala Gln Pro
    130                 135                 140

Thr Lys Lys Ser Thr Leu Lys Lys Arg Val Cys Arg Leu Pro Arg Pro
145                 150                 155                 160

Glu Thr Gln Lys Gly Arg Arg Arg Ala Arg Leu Arg Phe Met Lys
                165                 170                 175

Gln Pro Gln Gly Glu Gly Ile Ser Gly Thr Phe Val Pro Gln Cys Leu
            180                 185                 190

His Gly Tyr Tyr Ser Asn Thr Thr Ser Gln Lys Leu Leu Asn Pro
        195                 200                 205

Trp Ile Leu Lys Thr
    210

<210> SEQ ID NO 13
<211> LENGTH: 246
<212> TYPE: PRT
<213> ORGANISM: Homo sapiens

<400> SEQUENCE: 13

Met Arg Pro Arg Leu Trp Leu Leu Leu Ala Ala Gln Leu Thr Val Leu
1               5                   10                  15

His Gly Asn Ser Val Leu Gln Gln Thr Pro Ala Tyr Ile Lys Val Gln
            20                  25                  30

Thr Asn Lys Met Val Met Leu Ser Cys Glu Ala Lys Ile Ser Leu Ser
        35                  40                  45

```
Asn Met Arg Ile Tyr Trp Leu Arg Gln Arg Gln Ala Pro Ser Ser Asp
 50                  55                  60

Ser His His Glu Phe Leu Ala Leu Trp Asp Ser Ala Lys Gly Thr Ile
 65                  70                  75                  80

His Gly Glu Glu Val Glu Gln Glu Lys Ile Ala Val Phe Arg Asp Ala
                 85                  90                  95

Ser Arg Phe Ile Leu Asn Leu Thr Ser Val Lys Pro Glu Asp Ser Gly
                100                 105                 110

Ile Tyr Phe Cys Met Ile Val Gly Ser Pro Glu Leu Thr Phe Gly Lys
                115                 120                 125

Gly Thr Gln Leu Ser Val Val Asp Phe Leu Pro Thr Thr Ala Gln Pro
130                 135                 140

Thr Lys Lys Ser Thr Leu Lys Lys Arg Val Cys Arg Leu Pro Arg Pro
145                 150                 155                 160

Glu Thr Gln Lys Gly Pro Leu Cys Ser Pro Ile Thr Leu Gly Leu Leu
                165                 170                 175

Val Ala Gly Val Leu Val Leu Leu Val Ser Leu Gly Val Ala Ile His
                180                 185                 190

Leu Cys Cys Arg Arg Arg Arg Ala Arg Leu Arg Phe Met Lys Gln Lys
                195                 200                 205

Phe Asn Ile Val Cys Leu Lys Ile Ser Gly Phe Thr Thr Cys Cys Cys
210                 215                 220

Phe Gln Ile Leu Gln Ile Ser Arg Glu Tyr Gly Phe Gly Val Leu Leu
225                 230                 235                 240

Gln Lys Asp Ile Gly Gln
                245

<210> SEQ ID NO 14
<211> LENGTH: 243
<212> TYPE: PRT
<213> ORGANISM: Homo sapiens

<400> SEQUENCE: 14

Met Arg Pro Arg Leu Trp Leu Leu Leu Ala Ala Gln Leu Thr Val Leu
 1                   5                  10                  15

His Gly Asn Ser Val Leu Gln Gln Thr Pro Ala Tyr Ile Lys Val Gln
                 20                  25                  30

Thr Asn Lys Met Val Met Leu Ser Cys Glu Ala Lys Ile Ser Leu Ser
                 35                  40                  45

Asn Met Arg Ile Tyr Trp Leu Arg Gln Arg Gln Ala Pro Ser Ser Asp
 50                  55                  60

Ser His His Glu Phe Leu Ala Leu Trp Asp Ser Ala Lys Gly Thr Ile
 65                  70                  75                  80

His Gly Glu Glu Val Glu Gln Glu Lys Ile Ala Val Phe Arg Asp Ala
                 85                  90                  95

Ser Arg Phe Ile Leu Asn Leu Thr Ser Val Lys Pro Glu Asp Ser Gly
                100                 105                 110

Ile Tyr Phe Cys Met Ile Val Gly Ser Pro Glu Leu Thr Phe Gly Lys
                115                 120                 125

Gly Thr Gln Leu Ser Val Val Asp Phe Leu Pro Thr Thr Ala Gln Pro
130                 135                 140

Thr Lys Lys Ser Thr Leu Lys Lys Arg Val Cys Arg Leu Pro Arg Pro
145                 150                 155                 160

Glu Thr Gln Lys Gly Pro Leu Cys Ser Pro Ile Thr Leu Gly Leu Leu
```

```
                165                 170                 175
Val Ala Gly Val Leu Val Leu Val Ser Leu Gly Val Ala Ile His
            180                 185                 190
Leu Cys Cys Arg Arg Arg Ala Arg Leu Arg Phe Met Lys Gln Pro
            195                 200                 205
Gln Gly Glu Gly Ile Ser Gly Thr Phe Val Pro Gln Cys Leu His Gly
            210                 215                 220
Tyr Tyr Ser Asn Thr Thr Thr Ser Gln Lys Leu Leu Asn Pro Trp Ile
225                 230                 235                 240
Leu Lys Thr

<210> SEQ ID NO 15
<211> LENGTH: 180
<212> TYPE: PRT
<213> ORGANISM: Homo sapiens

<400> SEQUENCE: 15

Met Arg Pro Arg Leu Trp Leu Leu Leu Ala Ala Gln Leu Thr Val Leu
1               5                   10                  15
His Gly Asn Ser Val Leu Gln Gln Thr Pro Ala Tyr Ile Lys Val Gln
            20                  25                  30
Thr Asn Lys Met Val Met Leu Ser Cys Glu Ala Lys Ile Ser Leu Ser
        35                  40                  45
Asn Met Arg Ile Tyr Trp Leu Arg Gln Arg Gln Ala Pro Ser Ser Asp
    50                  55                  60
Ser His His Glu Phe Leu Ala Leu Trp Asp Ser Ala Lys Gly Thr Ile
65                  70                  75                  80
His Gly Glu Glu Val Glu Gln Glu Lys Ile Ala Val Phe Arg Asp Ala
                85                  90                  95
Ser Arg Phe Ile Leu Asn Leu Thr Ser Val Lys Pro Glu Asp Ser Gly
            100                 105                 110
Ile Tyr Phe Cys Met Ile Val Gly Ser Pro Glu Leu Thr Phe Gly Lys
        115                 120                 125
Gly Thr Gln Leu Ser Val Val Asp Phe Leu Pro Thr Thr Ala Gln Pro
    130                 135                 140
Thr Lys Lys Ser Thr Leu Lys Lys Arg Val Cys Arg Leu Pro Arg Pro
145                 150                 155                 160
Glu Thr Gln Lys Gly Arg Arg Arg Ala Arg Leu Arg Phe Met Lys
                165                 170                 175
Gln Phe Tyr Lys
            180

<210> SEQ ID NO 16
<211> LENGTH: 206
<212> TYPE: PRT
<213> ORGANISM: Homo sapiens

<400> SEQUENCE: 16

Met Arg Pro Arg Leu Trp Leu Leu Leu Ala Ala Gln Leu Thr Val Leu
1               5                   10                  15
His Gly Asn Ser Val Leu Gln Gln Thr Pro Ala Tyr Ile Lys Val Gln
            20                  25                  30
Thr Asn Lys Met Val Met Leu Ser Cys Glu Ala Lys Ile Ser Leu Ser
        35                  40                  45
Asn Met Arg Ile Tyr Trp Leu Arg Gln Arg Gln Ala Pro Ser Ser Asp
    50                  55                  60
```

```
Ser His His Glu Phe Leu Ala Leu Trp Asp Ser Ala Lys Gly Thr Ile
 65                  70                  75                  80

His Gly Glu Glu Val Glu Gln Glu Lys Ile Ala Val Phe Arg Asp Ala
                 85                  90                  95

Ser Arg Phe Ile Leu Asn Leu Thr Ser Val Lys Pro Glu Asp Ser Gly
            100                 105                 110

Ile Tyr Phe Cys Met Ile Val Gly Ser Pro Glu Leu Thr Phe Gly Lys
        115                 120                 125

Gly Thr Gln Leu Ser Val Val Asp Phe Leu Pro Thr Thr Ala Gln Pro
130                 135                 140

Thr Lys Lys Ser Thr Leu Lys Lys Arg Val Cys Arg Leu Pro Arg Pro
145                 150                 155                 160

Glu Thr Gln Lys Asp Phe Thr Asn Lys Gln Arg Ile Gly Phe Trp Cys
                165                 170                 175

Pro Ala Thr Lys Arg His Arg Ser Val Met Ser Thr Met Trp Lys Asn
            180                 185                 190

Glu Arg Arg Asp Thr Phe Asn Pro Gly Glu Phe Asn Gly Cys
        195                 200                 205

<210> SEQ ID NO 17
<211> LENGTH: 198
<212> TYPE: PRT
<213> ORGANISM: Homo sapiens

<400> SEQUENCE: 17

Met Arg Pro Arg Leu Trp Leu Leu Leu Ala Ala Gln Leu Thr Val Leu
 1               5                  10                  15

His Gly Asn Ser Val Leu Gln Gln Thr Pro Ala Tyr Ile Lys Val Gln
                20                  25                  30

Thr Asn Lys Met Val Met Leu Ser Cys Glu Ala Lys Ile Ser Leu Ser
            35                  40                  45

Asn Met Arg Ile Tyr Trp Leu Arg Gln Arg Gln Ala Pro Ser Ser Asp
 50                  55                  60

Ser His His Glu Phe Leu Ala Leu Trp Asp Ser Ala Lys Gly Thr Ile
 65                  70                  75                  80

His Gly Glu Glu Val Glu Gln Glu Lys Ile Ala Val Phe Arg Asp Ala
                 85                  90                  95

Ser Arg Phe Ile Leu Asn Leu Thr Ser Val Lys Pro Glu Asp Ser Gly
            100                 105                 110

Ile Tyr Phe Cys Met Ile Val Gly Ser Pro Glu Leu Thr Phe Gly Lys
        115                 120                 125

Gly Thr Gln Leu Ser Val Val Asp Phe Leu Pro Thr Thr Ala Gln Pro
130                 135                 140

Thr Lys Lys Ser Thr Leu Lys Lys Arg Val Cys Arg Leu Pro Arg Pro
145                 150                 155                 160

Glu Thr Gln Lys Gly Leu Lys Gly Lys Val Tyr Gln Glu Pro Leu Ser
                165                 170                 175

Pro Asn Ala Cys Met Asp Thr Thr Ala Ile Leu Gln Pro His Arg Ser
            180                 185                 190

Cys Leu Thr His Gly Ser
        195

<210> SEQ ID NO 18
<211> LENGTH: 288
<212> TYPE: PRT
```

-continued

<213> ORGANISM: Homo sapiens

<400> SEQUENCE: 18

```
Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
        195                 200                 205

Leu Lys Glu Asp Pro Ser Ala Val Pro Val Phe Ser Val Asp Tyr Gly
    210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
        275                 280                 285
```

<210> SEQ ID NO 19
<211> LENGTH: 9
<212> TYPE: PRT
<213> ORGANISM: Human papillomavirus type 16

<400> SEQUENCE: 19

```
Arg Ala His Tyr Asn Ile Val Thr Phe
1               5
```

<210> SEQ ID NO 20
<211> LENGTH: 9
<212> TYPE: PRT
<213> ORGANISM: Homo sapiens

<400> SEQUENCE: 20

```
Lys Val Pro Arg Asn Gln Asp Trp Leu
1               5
```

```
<210> SEQ ID NO 21
<211> LENGTH: 13
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: X is D alanine
<220> FEATURE:
<221> NAME/KEY: MISC_FEATURE
<222> LOCATION: (3)..(3)
<223> OTHER INFORMATION: X is 1-cyclohexylalanine
<220> FEATURE:
<221> NAME/KEY: MISC_FEATURE
<222> LOCATION: (13)..(13)
<223> OTHER INFORMATION: X is D-alanine

<400> SEQUENCE: 21

Xaa Lys Xaa Val Ala Ala Trp Thr Leu Lys Ala Ala Xaa
1               5                   10

<210> SEQ ID NO 22
<211> LENGTH: 8
<212> TYPE: PRT
<213> ORGANISM: Gallus gallus

<400> SEQUENCE: 22

Ser Ile Ile Asn Phe Glu Lys Leu
1               5

<210> SEQ ID NO 23
<211> LENGTH: 8
<212> TYPE: PRT
<213> ORGANISM: Gallus gallus

<400> SEQUENCE: 23

Ser Ile Ile Gly Phe Glu Lys Leu
1               5
```